US006929939B2

(12) United States Patent
Estell et al.

(10) Patent No.: US 6,929,939 B2
(45) Date of Patent: *Aug. 16, 2005

(54) PROTEINS PRODUCING AN ALTERED IMMUNOGENIC RESPONSE AND METHODS OF MAKING AND USING THE SAME

(75) Inventors: David A. Estell, San Mateo, CA (US); Grant C. Ganshaw, Tracy, CA (US); Fiona A. Harding, Santa Clara, CA (US); Edmund A. Larenas, Moss Beach, CA (US); Ayrookaran J. Poulose, Belmont, CA (US); Elizabeth E. Sikorski, Fairfield, OH (US); Elliott P. Russell, Egham (GB)

(73) Assignees: Genencor International, Inc., Palo Alto, CA (US); The Procter & Gamble Company, Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 10/104,693

(22) Filed: Mar. 22, 2002

(65) Prior Publication Data

US 2003/0118605 A1 Jun. 26, 2003

Related U.S. Application Data

(60) Provisional application No. 60/278,459, filed on Mar. 23, 2001.

(51) Int. Cl.[7] .......................... C12N 9/52; C12N 9/54; C12N 9/56; A61K 38/48; A61K 7/28
(52) U.S. Cl. .................. 435/220; 435/221; 435/222; 435/252.3; 435/252.31; 435/320.1; 424/94.64; 424/401; 510/119; 510/130; 536/23.2
(58) Field of Search ................... 435/220, 221, 435/222, 252.3, 252.31, 320.1, 69.1, 471; 424/94.64, 401; 510/119, 130; 536/23.2

(56) References Cited

U.S. PATENT DOCUMENTS

| 3,755,560 | A | 8/1973 | Dickert et al. |
| 3,929,678 | A | 12/1975 | Laughlin et al. |
| 4,076,663 | A | 2/1978 | Masuda et al. |
| 4,152,416 | A | 5/1979 | Spitzer et al. |

(Continued)

FOREIGN PATENT DOCUMENTS

| EP | 0 134 267 B1 | 8/1989 |
| EP | 0 130 756 B1 | 2/1991 |

(Continued)

OTHER PUBLICATIONS

Achstetter, Tilman et al., "New Proteolytic Enzymes in Yeast," Archives of Biochemistry and Biophysics, 207(2): 445–454, 1981.

(Continued)

*Primary Examiner*—Ponnathapura Achutamurthy
*Assistant Examiner*—William W. Moore
(74) *Attorney, Agent, or Firm*—Genencor International, Inc.

(57) ABSTRACT

The present invention relates to novel protein variants that exhibit reduced allergenicity when compared to the parental proteins. Also included are DNA molecules that encode the novel variants, host cells comprising the DNA and methods of making proteins less allergenic.

17 Claims, 23 Drawing Sheets

U.S. PATENT DOCUMENTS

| | | | |
|---|---|---|---|
| 4,261,868 A | 4/1981 | Hora et al. | |
| 4,387,089 A | 6/1983 | De Polo | |
| 4,404,128 A | 9/1983 | Anderson | |
| 4,421,769 A | 12/1983 | Dixon et al. | |
| 4,533,359 A | 8/1985 | Kondo et al. | |
| 4,663,157 A | 5/1987 | Brock | |
| 4,760,025 A | 7/1988 | Estell et al. | |
| 4,914,031 A * | 4/1990 | Zukowski et al. | 435/222 |
| 4,937,370 A | 6/1990 | Sabatelli | |
| 4,990,452 A * | 2/1991 | Bryan et al. | 435/222 |
| 4,999,186 A | 3/1991 | Sabatelli et al. | |
| 5,011,681 A | 4/1991 | Ciotti et al. | |
| 5,073,371 A | 12/1991 | Turner et al. | |
| 5,073,372 A | 12/1991 | Turner et al. | |
| 5,087,372 A | 2/1992 | Toyomoto et al. | |
| 5,116,741 A * | 5/1992 | Bryan et al. | 435/87 |
| 5,185,258 A | 2/1993 | Caldwell et al. | |
| 5,204,015 A | 4/1993 | Caldwell et al. | |
| 5,264,366 A | 11/1993 | Ferrari et al. | |
| RE34,606 E | 5/1994 | Estell et al. | |
| 5,397,705 A * | 3/1995 | Zukowski et al. | 435/222 |
| 5,441,882 A | 8/1995 | Estell et al. | |
| 5,487,884 A | 1/1996 | Bissett et al. | |
| 5,665,587 A * | 9/1997 | Aaslyng et al. | 435/221 |
| 5,677,272 A * | 10/1997 | Ghosh et al. | 510/306 |
| 5,827,508 A | 10/1998 | Tanner et al. | |
| 5,935,556 A | 8/1999 | Tanner et al. | |
| 5,968,485 A | 10/1999 | Robinson | |
| 5,972,316 A | 10/1999 | Robinson | |
| 6,312,936 B1 * | 11/2001 | Poulose et al. | 435/219 |
| 6,428,799 B1 * | 8/2002 | Cen et al. | 424/402 |
| 6,586,221 B2 * | 7/2003 | Graycar et al. | 435/219 |
| 6,586,223 B1 * | 7/2003 | Sikorski et al. | 435/220 |
| 6,596,525 B1 * | 7/2003 | Estell et al. | 435/219 |

FOREIGN PATENT DOCUMENTS

| | | |
|---|---|---|
| EP | 0 251 446 B1 | 12/1994 |
| EP | 0 680 745 B1 | 11/2002 |
| WO | WO 89/06279 | 7/1989 |
| WO | WO 92/10755 | 6/1992 |
| WO | WO 94/10191 | 5/1994 |
| WO | WO 95/23780 | 9/1995 |
| WO | WO 95/34280 | 12/1995 |
| WO | WO 96/03964 | 2/1996 |
| WO | WO 96/16636 | 6/1996 |
| WO | WO 96/17929 | 6/1996 |
| WO | WO 96/40791 | 12/1996 |
| WO | WO 97/30148 | 8/1997 |
| WO | WO 98/22085 | 5/1998 |
| WO | WO 99/49056 | 9/1999 |
| WO | WO 99/53078 | 10/1999 |
| WO | WO 00/06110 | 2/2000 |
| WO | WO 00/24372 | 5/2000 |
| WO | WO 01/057578 A3 | 2/2001 |
| WO | WO 02/040997 | 5/2002 |

OTHER PUBLICATIONS

Altschul, Stephen F. et al., "Basic Local Alignment Search Tool," J. Mol. Biol., 215: 403–410, 1990.

Ausubel et al. (eds.) Current Protocols, a joint venture between Greene Publishing Assoc. Inc. and John Wiley & Sons Inc. (1997 supplement).

Benton, W. David et al., "Screening λgt Recombinant Clones by Hybridization to Single Plaques in situ," Science, 196: 180–182, 1977.

CTFA International Cosmetic Ingredient Dictionary and Handbook, 6$^{th}$ ed., pp. 1026–1028 & 1103, 1995.

Giver, Lori et al., "Directed evolution of a thermostable esterase," Proc. Natl. Acad. Sci. USA, 95: 12809–12813, 1998.

DelMar, E.G. et al., "A Sensitive New Substrate For Chymotrypsin," Analytical Biochemistry, 99: 316–320, 1979.

Federal Register, 43, No. 166, pp. 38206–38269. Aug. 25, 1978.

Grunstein, Michael et al., "Colony hybridization: A method for the isolation of cloned DNAs that contain a specific gene," Proc. Natl. Acad. Sci. USA, 72(10): 3961–3965, 1975.

Grusby, Michael J. et al., Mice lacking major histocompatibility complex class I and class II molecules, Proc Nat Acad. USA, 90 :3913–3917, 1993.

Harayama, Shigeaki, "Artificial evolution by DNA shuffling," Trends Biotechnol., 16 :76–81, 1998.

Henikoff, Steven et al., "Amino acid substitution matrices from protein blocks," Proc. Natl. Acad. Sci. USA, 89: 10915–10919, 1992.

Herman, Ann E. et al., "Determination of Glutamic Acid Decarboxylase 65 Peptides Presented by the Type I Diabetes–Associated HLA–DQ8 Class II Molecule Identifies an Immunogenic Peptide Motif," J. Immunol., 163 :6275–6282, 1999.

Karlin, Samuel et al., "Applications and statistics for multiple high–scoring segments in molecular sequences," Proc. Natl. Acad. Sci. USA, 90: 5873–5877, 1993.

Kuchner, Olga et al., "Directed evolution of enzyme catalysts," Trends Biotechnol., 15 :523–530, 1997.

Lin, Zhanglin et al., "Functional Expression of Horseradish Peroxidase in E. coli by Directed Evolution," Biotechnol. Prog., 15 :467–471, 1999.

McCutcheon's Detergents and Emulsifiers, N. American Edition, 1986.

Moore, Jeffrey C. et al., "Strategies for the in vitro Evolution of Protein Function: Enzyme Evolution by Random Recombination of Improved Sequences," J. Mol. Biol., 272: 336–347, 1997.

Needleman, Saul B. et al., "A General Method Applicable to the Search for Similarities in the Amino Acid Sequence of Two Proteins," J. Mol Biol., 48 :443–453, 1970.

Noll, Walter, Chemistry and Technology Silicones, New York Academic Press, 1968.

Patentin User Manual (GenBank, Mountain View CA), p. 101, 1990.

Patten, Philip A. et al., "Applications of DNA shuffling to pharmaceuticals and vaccines," Current Opinion in Biotechnol., 8:724–733, 1997.

PCR Primer, a Laboratory Manual, Cold Spring Harbor Press, Plainview, NY, 1995.

Pearson, William R. et al., "Improved tools for biological sequence comparison," Proc. Natl. Acad. Sci. USA, 85:2444–2448, 1988.

Research Disclosure 21634, Apr., 1982.

Sagarin, E., Cosmetics, Science & Technology, 2$^{nd}$ ed., vol. 1, pp. 189 et seq., 1972.

Sagarin, E., Cosmetics, Science & Technology, 2$^{nd}$ ed., vol. 1, pp. 32–43, 1972.

Sambrook et al., Molecular Cloning—A Laboratory Manual. 2$^{nd}$ ed., vol. 1–3, Cold Springs Harbor Publishing, 1989.

Sayre, Robert M., "Physical Sunscreens," J. Soc. Cosmet. Chem., 41(2):103–109, 1990.

Smith, Temple F. et al., "Comparison of Biosequences," Adv. Appl. Math. 2:482–489, 1981.

Sønderstrup, Grete et al., "HLA class II transgenic mice: models of the human CD4+T–cell Immune response," Immunol. Rev., 172:335–343, 1999.

Stemmer, Willem P.C., "DNA shuffling by random fragmentation and reassembly: in vitro recombination for molecular evolution," Proc. Natl. Acad. Sci., USA 91:10747–10751, 1994.

Stickler, M.M. et al., "CD4+T–cell Epitope Determination Using Unexposed Human Donor Peripheral Blood Mononuclear Cells," J. of Immunotherapy, 23(6):654–660, 2000.

Sun, Fengzhu, "Modeling DNA Shuffling," J. of Computational Biol., 6(1):77–90, 1999.

Taneja, Veena et al., "HLA class II transgenic mice as models of human diseases," Immunol. Rev., 169:67–79, 1999.

Taurog, Joel D. et al., "Inflammatory disease in HLA–B27 transgenic rats," Immunol. Rev., 169:209–223, 1999.

Wenninger, John A. et al., ed. CTFA *International Cosmetic Ingredient Dictionary and Handbook,* 7th ed., vol., 2, p 1672, 1997.

Zhao, Huimin et al., "Molecular evolution by staggered extension process (StEP) in vitro recombination," Nature Biotechnology, 16:258–261, 1998.

* cited by examiner

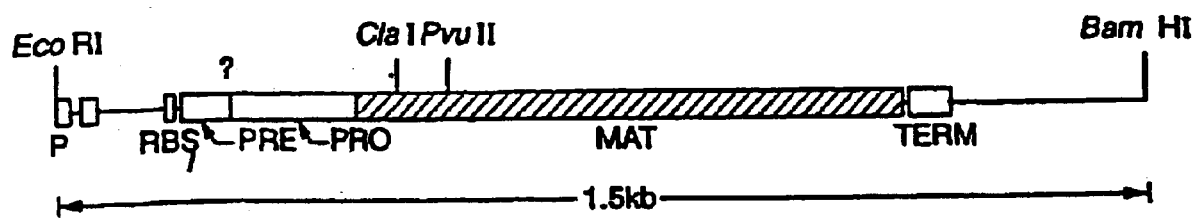
FIG._1A

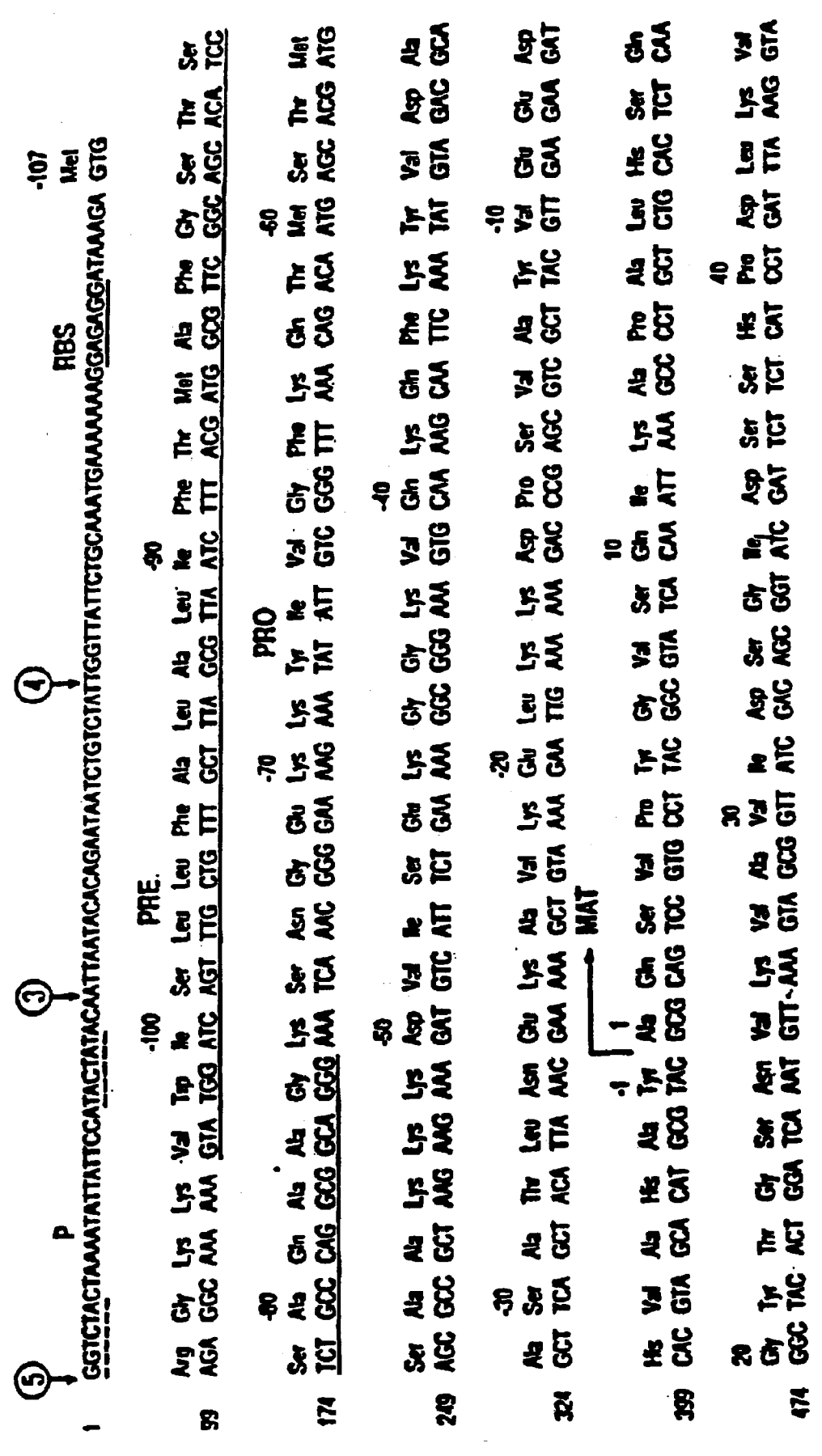

```
                                    250   Gln
          Gln  Val  Arg  Ser  Ser  Leu  Glu  Asn  Thr  Thr  Thr  Lys  Leu  Gly  Asp  Ser  Phe  Tyr  Tyr  Gly  Lys  Gly  Leu  Ile  Asn
     1149 CAA  GTC  CGC  AGC  AGT  TTA  GAA  AAC  ACC  ACT  ACA  AAA  CTT  GGT  GAT  TCT  TTC  TAC  TAT  GGA  AAA  GGG  CTG  ATC  AAC 270                            275                                TERM
          Val  Gln  Ala  Ala  Ala  Val  Gln  Ala  Ala  Gln  OC
     1224 GTA CAG GCA GCT GCA GTT CAG GCT CAG TAA AACATAAAAACCGGCCCTTGGGCCCCGCGGTTTTTATTTCTTCCTCCGCATGTTCAATCGGCTCC

1316 ATAATCGACGGATGGCTCCCTCTGAAAATTTAACGAGAAACGGCCAAGTCCTGAAACGTCTCAATCGGCCG

1416 CTTCCCGGTTTCCGGTCAGCTCAATGCGGGAGACGGGCATTCGTAATCGGATC
```

CONSERVED RESIDUES IN SUBTILISINS FROM BACILLUS AMYLOLIQUEFACIENS

COMPARISON OF SUBTILISIN SEQUENCES FROM:
B.amyloliquefaciens
B.subtilis
B.licheniformis
B.lentus

```
                  10                  20                  30
01   AQSVPYGVSQIKAPALHSQGYTGSNVKVAVIDSGIDSSHP
     AQSVPYGISQIKAPALHSQGYTGSNVKVAVIDSGIDSSHP
     AQTVPYGIPLIKADKVQAQGFKGANVKVAVLDTGIQASHP
     AQSVPWGISRVQAPAAHNRGLTGSGVKVAVLDTGIST*HP 50                  60                  70
41   DLKVAGGASHVPSETNPFQDNSHGTHVAGTVAALNNSIG
     DLNVRGGASFVPSETNPYQDGSSHGTHVAGTIAALNNSIG
     DLNVVGGASFVAGEAYN*TDGNGHGTHVAGTVAALDNTTG
     DLNIRGGASFVPGEPSTQDGNGHGTHVAGTIAALNNSIG 90                 100                 110
81   VLGVAPSASLYAVKVLGADGSGQYSWIINGIEWAIANNMD
     VLGVSPSASLYAVKVLDSTGSGQYSWIINGIEHVAISNMD
     VLGVAPSVSLYAVKVLNSSGSGTYSGIVSGIEWATTNGMD
     VLGVAPSAELYAVKVLGASGSGSVSSIAQGLEWAGNNGMH 130                 140                 150
121  VINMSLGGPSGSAALKAAVDKAVASGVVVVAAAGNEGTSG
     VINMSLGGPTGSTALKTVVDKAVSSGIVVAAAAGNEGSSG
     VINMSLGGASGSTAMKQAVDNAYARGVVVVAAAGNSGAG
     VANLSLGSPSPSATLEQAVNSATSRGVLVVAASGNSGAG
```

FIG.—3A

```
161              170       180       190
SSS TVG TPG KTP PSV IAV GAV DSS NQR ASF SSV GPE LDV KA
STT TVG TPG IPA KYP STI IAV GAV NSS NQR ASF SAG SEL DVK A
STN TIG YPA KID SYI AVG AVD SNN RAS FSF SAG AEL EVK A
S.. ... HSY PAR YAN AMA VGA TDQ NNR ASF SQT GAG LDI VA 201              210       220       230
PGV SIQ STL PGN KYG AIN GTS MAS PHV AGA ALI LSK HPN
PGV SIQ STL PGG TYG AIN GTS MAT PHY AGA AAL ILS KHP T
PGA GYP TBY TPT HYN ATL NGT SMA SPH VAG AAA LIL SKH PN
PGV NVQ BTY PGB TYA BLN GTS MAT PHV AGA ALV KQK NPS 241              250       260       270
WTN TQV RSS LEN TTK LGD SFY TGK GLI NVQ AAA Q
WTN HAQ VRD RLS TAT TIL GNS FYT GKG LIN VQA AAA Q
LSA BQV RNR LBB TAT TLG SSF YTG KGL INV BAA AAQ
WSN VQI RNH LKN TAT BLG STN LYG BGL VNA BAA TR
```

| | |
|---|---:|
| Ala Gln Ser Val Pro Tyr Gly Val Ser Gln Ile Lys Ala Pro Ala | 15 |
| Leu His Ser Gln Gly Tyr Thr Gly Ser Asn Val Lys Val Ala Val | 30 |
| Ile Asp Ser Gly Ile Asp Ser Ser His Pro Asp Leu Lys Val Ala | 45 |
| Gly Gly Ala Ser Met Val Pro Ser Glu Thr Asn Pro Phe Gln Asp | 60 |
| Asn Asn Ser His Gly Thr His Val Ala Gly Thr Val Ala Ala Leu | 75 |
| Asn Asn Ser Ile Gly Val Leu Gly Val Ala Pro Ser Ala Ser Leu | 90 |
| Try Ala Val Lys Val Leu Gly Ala Asp Gly Ser Gly Gln Tyr Ser | 105 |
| Trp Ile Ile Asn Gly Ile Glu Trp Ala Ile Ala Asn Asn Met Asp | 120 |
| Val Ile Asn Met Ser Leu Gly Gly Pro Ser Gly Ser Ala Ala Leu | 135 |
| Lys Ala Ala Val Asp Lys Ala Val Ala Ser Gly Val Val Val Val | 150 |
| Ala Ala Ala Gly Asn Glu Gly Thr Ser Gly Ser Ser Ser Thr Val | 165 |
| Gly Tyr Pro Gly Lys Tyr Pro Ser Val Ile Ala Val Gly Ala Val | 180 |
| Asp Ser Ser Asn Gln Arg Ala Ser Phe Ser Ser Val Gly Pro Glu | 195 |
| Leu Asp Val Met Ala Pro Gly Val Ser Ile Gln Ser Thr Leu Pro | 210 |
| Gly Asn Lys Tyr Gly Ala Leu Asn Gly Thr Ser Met Ala Ser Pro | 225 |
| His Val Ala Gly Ala Ala Ala Leu Ile Leu Ser Lys His Pro Asn | 240 |
| Trp Thr Asn Thr Gln Val Arg Ser Ser Leu Glu Asn Thr Thr Thr | 255 |
| Lys Leu Gly Asp Ser Phe Tyr Tyr Gly Lys Gly Leu Ile Asn Val | 270 |
| Gln Ala Ala Ala Gln | 275 |

FIG. 6

AGIEWAIANNMDVIN

NAIEWAIANNMDVIN

NGAEWAIANNMDVIN

NGIAWAIANNMDVIN

NGIEAAIANNMDVIN

NGIEWAIANNMDVIN

NGIEWAAANNMDVIN

NGIEWAIANNMDVIN

NGIEWAIAANMDVIN

NGIEWAIANAMDVIN

NGIEWAIANNADVIN

NGIEWAIANNMAVIN

NGIEWAIANNMDAIN

NGIEWAIANNMDVAN

NGIEWAIANNMDVIA

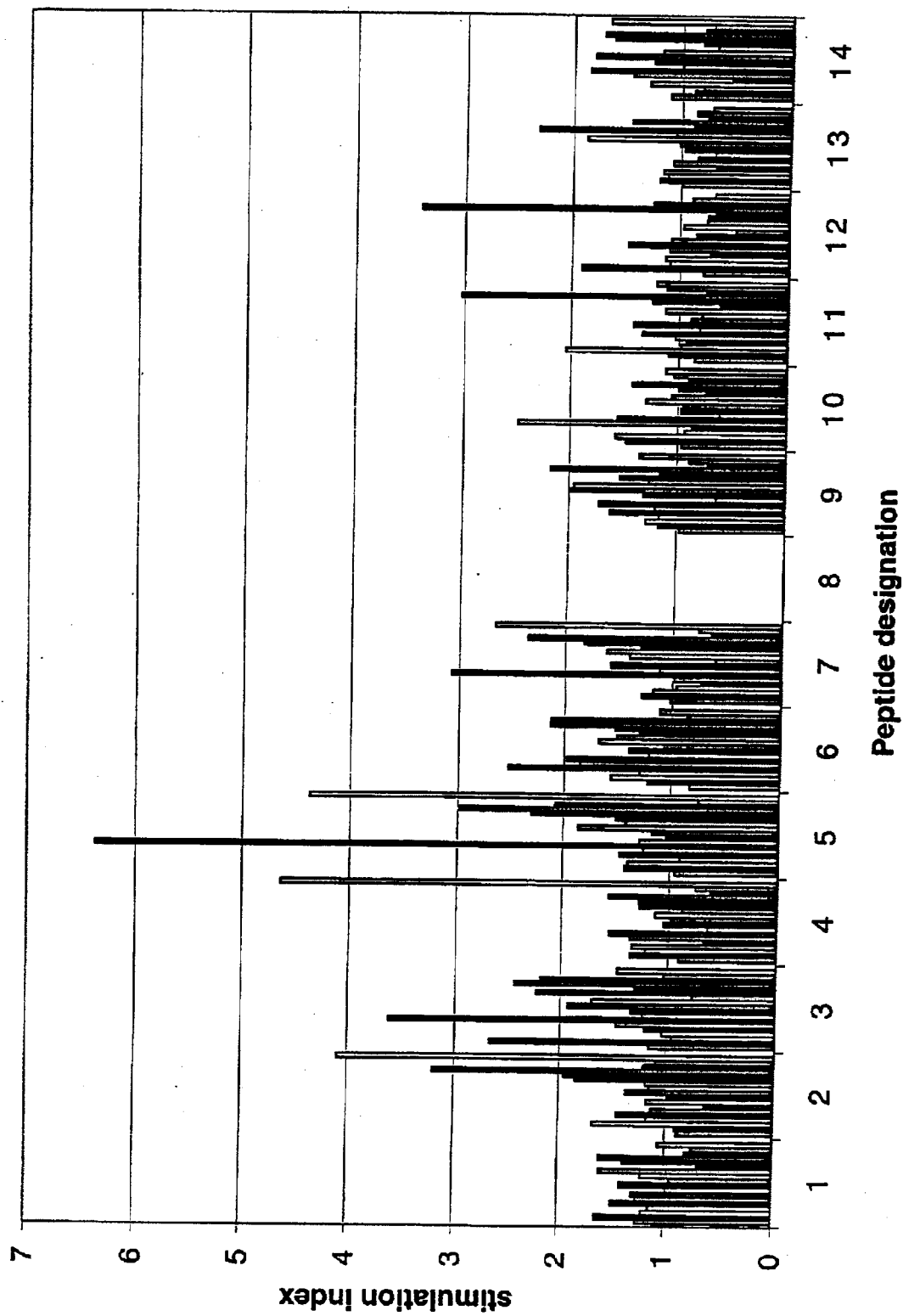

SEQUENCE LISTING

<160> NUMBER OF SEQ ID NOS: 31

<210> SEQ ID NO 1
<211> LENGTH: 1494
<212> TYPE: DNA
<213> ORGANISM: Bacillus amyloiquefaciens

<400> SEQUENCE: 1

```
ggtctactaa aatattattc catactatac aattaataca cagaataatc tgtctattgg      60
ttattctgca aatgaaaaaa aggagaggat aaagagtgag aggcaaaaaa gtatggatca     120
gtttgctgtt tgctttagcg ttaatcttta cgatggcgtt cggcagcaca tcctctgccc     180
aggcggcagg gaaatcaaac ggggaaaaga aatatattgt cgggtttaaa cagacaatga     240
gcacgatgag cgccgctaag aagaaagatg tcatttctga aaaaggcggg aaagtgcaaa     300
agcaattcaa atatgtagac gcagcttcag ctacattaaa cgaaaaagct gtaaaagaat     360
tgaaaaaaga cccgagcgtc gcttacgttg aagaagatca cgtagcacat gcgtacgcgc     420
agtccgtgcc ttacggcgta tcacaaatta aagcccctgc tctgcactct caaggctaca     480
ctggatcaaa tgttaaagta gcggttatcg acagcggtat cgattcttct catcctgatt     540
taaaggtagc aggcggagcc agcatggttc cttctgaaac aaatcctttc caagacaaca     600
actctcacgg aactcacgtt gccggcacag ttgcggctct taataactca atcggtgtat     660
taggcgttgc gccaagcgca tcactttacg ctgtaaaagt tctcggtgct gacggttccg     720
gccaatacag ctggatcatt aacggaatcg agtgggcgat cgcaaacaat atggacgtta     780
ttaacatgag cctcggcgga ccttctggtt ctgctgcttt aaaagcggca gttgataaag     840
ccgttgcatc cggcgtcgta gtcgttgcgg cagccggtaa cgaaggcact tccggcagct     900
```

-continued

```
caagcacagt gggctaccct ggtaaatacc cttctgtcat tgcagtaggc gctgttgaca      960
gcagcaacca aagagcatct ttctcaagcg taggacctga gcttgatgtc atggcacctg     1020
gcgtatctat ccaaagcacg cttcctggaa acaaatacgg ggcgtacaac ggtacgtcaa     1080
tggcatctcc gcacgttgcc ggagcggctg ctttgattct ttctaagcac ccgaactgga     1140
caaacactca gtccgcagc  agtttagaaa acaccactac aaaacttggt gattctttct     1200
actatggaaa agggctgatc aacgtacagg cggcagctca gtaaaacata aaaaaccggc     1260
cttggccccg ccggttttt  attttcttc  ctccgcatgt tcaatccgct ccataatcga     1320
cggatggctc cctctgaaaa ttttaacgag aaacggcggg ttgacccggc tcagtcccgt     1380
aacggccaag tcctgaaacg tctcaatcgc cgcttcccgg tttccggtca gctcaatgcc     1440
gtaacggtcg gcggcgtttt cctgataccg ggagacggca ttcgtaatcg gatc          1494
```

<210> SEQ ID NO 2
<211> LENGTH: 382
<212> TYPE: PRT
<213> ORGANISM: Bacillus amyloiquefaciens

<400> SEQUENCE: 2

```
Met Arg Gly Lys Lys Val Trp Ile Ser Leu Leu Phe Ala Leu Ala Leu
 1               5                  10                  15

Ile Phe Thr Met Ala Phe Gly Ser Thr Ser Ser Ala Gln Ala Ala Gly
            20                  25                  30

Lys Ser Asn Gly Glu Lys Lys Tyr Ile Val Gly Phe Lys Gln Thr Met
        35                  40                  45

Ser Thr Met Ser Ala Ala Lys Lys Lys Asp Val Ile Ser Glu Lys Gly
    50                  55                  60

Gly Lys Val Gln Lys Gln Phe Lys Tyr Val Asp Ala Ala Ser Ala Thr
65                  70                  75                  80

Leu Asn Glu Lys Ala Val Lys Glu Leu Lys Lys Asp Pro Ser Val Ala
                85                  90                  95

Tyr Val Glu Glu Asp His Val Ala His Ala Tyr Ala Gln Ser Val Pro
            100                 105                 110

Tyr Gly Val Ser Gln Ile Lys Ala Pro Ala Leu His Ser Gln Gly Tyr
        115                 120                 125

Thr Gly Ser Asn Val Lys Val Ala Val Ile Asp Ser Gly Ile Asp Ser
    130                 135                 140

Ser His Pro Asp Leu Lys Val Ala Gly Gly Ala Ser Met Val Pro Ser
145                 150                 155                 160

Glu Thr Asn Pro Phe Gln Asp Asn Asn Ser His Gly Thr His Val Ala
                165                 170                 175

Gly Thr Val Ala Ala Leu Asn Asn Ser Ile Gly Val Leu Gly Val Ala
            180                 185                 190

Pro Ser Ala Ser Leu Tyr Ala Val Lys Val Leu Gly Ala Asp Gly Ser
        195                 200                 205

Gly Gln Tyr Ser Trp Ile Ile Asn Gly Ile Glu Trp Ala Ile Ala Asn
    210                 215                 220

Asn Met Asp Val Ile Asn Met Ser Leu Gly Gly Pro Ser Gly Ser Ala
225                 230                 235                 240

Ala Leu Lys Ala Ala Val Asp Lys Ala Val Ala Ser Gly Val Val Val
                245                 250                 255

Val Ala Ala Ala Gly Asn Glu Gly Thr Ser Gly Ser Ser Ser Thr Val
            260                 265                 270
```

```
Gly Tyr Pro Gly Lys Tyr Pro Ser Val Ile Ala Val Gly Ala Val Asp
            275                 280                 285

Ser Ser Asn Gln Arg Ala Ser Phe Ser Ser Val Gly Pro Glu Leu Asp
        290                 295                 300

Val Met Ala Pro Gly Val Ser Ile Gln Ser Thr Leu Pro Gly Asn Lys
305                 310                 315                 320

Tyr Gly Ala Tyr Asn Gly Thr Ser Met Ala Ser Pro His Val Ala Gly
                325                 330                 335

Ala Ala Ala Leu Ile Leu Ser Lys His Pro Asn Trp Thr Asn Thr Gln
                340                 345                 350

Val Arg Ser Ser Leu Glu Asn Thr Thr Thr Lys Leu Gly Asp Ser Phe
            355                 360                 365

Tyr Tyr Gly Lys Gly Leu Ile Asn Val Gln Ala Ala Gln
370                 375                 380

<210> SEQ ID NO 3
<211> LENGTH: 275
<212> TYPE: PRT
<213> ORGANISM: Bacilllus amyloiquefaciens

<400> SEQUENCE: 3

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
                20                  25                  30

Ser Gly Ile Asp Ser Ser His Pro Asp Leu Lys Val Ala Gly Gly Ala
            35                  40                  45

Ser Met Val Pro Ser Glu Thr Asn Pro Phe Gln Asp Asn Asn Ser His
50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
            115                 120                 125

Pro Ser Gly Ser Ala Ala Leu Lys Ala Ala Val Asp Lys Ala Val Ala
130                 135                 140

Ser Gly Val Val Val Ala Ala Ala Gly Asn Glu Gly Thr Ser Gly Ser
145                 150                 155                 160

Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
            195                 200                 205

Leu Pro Gly Asn Lys Tyr Gly Ala Leu Asn Gly Thr Ser Met Ala Ser
        210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270
```

```
Ala Ala Gln
        275

<210> SEQ ID NO 4
<211> LENGTH: 269
<212> TYPE: PRT
<213> ORGANISM: Bacillus lentus

<400> SEQUENCE: 4

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 5
<211> LENGTH: 274
<212> TYPE: PRT
<213> ORGANISM: Bacillus licheniformis

<400> SEQUENCE: 5

Ala Gln Thr Val Pro Tyr Gly Ile Pro Leu Ile Lys Ala Asp Lys Val
1               5                   10                  15

Gln Ala Gln Gly Phe Lys Gly Ala Asn Val Lys Val Ala Val Leu Asp
            20                  25                  30

Thr Gly Ile Gln Ala Ser His Pro Asp Leu Asn Val Val Gly Gly Ala
        35                  40                  45
```

-continued

```
Ser Phe Val Ala Gly Glu Ala Tyr Asn Thr Asp Gly Asn Gly His Gly
     50                  55                  60

Thr His Val Ala Gly Thr Val Ala Ala Leu Asp Asn Thr Thr Gly Val
 65                  70                  75                  80

Leu Gly Val Ala Pro Ser Val Ser Leu Tyr Ala Val Lys Val Leu Asn
                 85                  90                  95

Ser Ser Gly Ser Gly Ser Tyr Ser Gly Ile Val Ser Gly Ile Glu Trp
             100                 105                 110

Ala Thr Thr Asn Gly Met Asp Val Ile Asn Met Ser Leu Gly Gly Ala
             115                 120                 125

Ser Gly Ser Thr Ala Met Lys Gln Ala Val Asp Asn Ala Tyr Ala Arg
     130                 135                 140

Gly Val Val Val Ala Ala Ala Gly Asn Ser Gly Asn Ser Gly Ser
145                 150                 155                 160

Thr Asn Thr Ile Gly Tyr Pro Ala Lys Tyr Asp Ser Val Ile Ala Val
                 165                 170                 175

Gly Ala Val Asp Ser Asn Ser Asn Arg Ala Ser Phe Ser Ser Val Gly
             180                 185                 190

Ala Glu Leu Glu Val Met Ala Pro Gly Ala Gly Val Tyr Ser Thr Tyr
         195                 200                 205

Pro Thr Asn Thr Tyr Ala Thr Leu Asn Gly Thr Ser Met Ala Ser Pro
     210                 215                 220

His Val Ala Gly Ala Ala Ala Leu Ile Leu Ser Lys His Pro Asn Leu
225                 230                 235                 240

Ser Ala Ser Gln Val Arg Asn Arg Leu Ser Ser Thr Ala Thr Tyr Leu
                 245                 250                 255

Gly Ser Ser Phe Tyr Tyr Gly Lys Gly Leu Ile Asn Val Glu Ala Ala
             260                 265                 270

Ala Gln
```

```
<210> SEQ ID NO 6
<211> LENGTH: 4
<212> TYPE: PRT
<213> ORGANISM: Artificial Sequence
<220> FEATURE:
<223> OTHER INFORMATION: succinyl-AAPF-para nitroanilide citation assay

<400> SEQUENCE: 6

Ala Ala Pro Phe
 1

<210> SEQ ID NO 7
<211> LENGTH: 15
<212> TYPE: PRT
<213> ORGANISM: Artificial Sequence
<220> FEATURE:
<223> OTHER INFORMATION: peptide variant based on P1 sequence

<400> SEQUENCE: 7

Gly Thr Val Ala Ala Leu Asn Asn Ser Ile Gly Val Leu Gly Val
 1               5                  10                  15

<210> SEQ ID NO 8
<211> LENGTH: 15
<212> TYPE: PRT
<213> ORGANISM: Artificial Sequence
<220> FEATURE:
<223> OTHER INFORMATION: peptide variant based on P1 sequence
```

-continued

```
<400> SEQUENCE: 8

Gly Thr Val Ala Ala Leu Asn Asn Ser Ala Gly Val Leu Gly Val
 1               5                  10                  15

<210> SEQ ID NO 9
<211> LENGTH: 15
<212> TYPE: PRT
<213> ORGANISM: Artificial Sequence
<220> FEATURE:
<223> OTHER INFORMATION: peptide variant based on P1 sequence

<400> SEQUENCE: 9

Gly Thr Val Ala Ala Leu Asp Asn Ser Ile Gly Val Leu Gly Val
 1               5                  10                  15

<210> SEQ ID NO 10
<211> LENGTH: 15
<212> TYPE: PRT
<213> ORGANISM: Artificial Sequence
<220> FEATURE:
<223> OTHER INFORMATION: peptide variant based on P1 sequence

<400> SEQUENCE: 10

Gly Thr Val Ala Ala Leu Asp Asn Ser Ala Gly Val Leu Gly Val
 1               5                  10                  15

<210> SEQ ID NO 11
<211> LENGTH: 15
<212> TYPE: PRT
<213> ORGANISM: Artificial Sequence
<220> FEATURE:
<223> OTHER INFORMATION: peptide variant based on P1 sequence

<400> SEQUENCE: 11

Gly Thr Val Ala Ala Leu Asn Asn Ser Ile Gly Ala Leu Gly Val
 1               5                  10                  15

<210> SEQ ID NO 12
<211> LENGTH: 15
<212> TYPE: PRT
<213> ORGANISM: Artificial Sequence
<220> FEATURE:
<223> OTHER INFORMATION: peptide variant based on P1 sequence

<400> SEQUENCE: 12

Gly Thr Val Ala Ala Leu Asp Asn Ser Ile Gly Ala Leu Gly Val
 1               5                  10                  15

<210> SEQ ID NO 13
<211> LENGTH: 15
<212> TYPE: PRT
<213> ORGANISM: Artificial Sequence
<220> FEATURE:
<223> OTHER INFORMATION: peptide variant based on P1 sequence

<400> SEQUENCE: 13

Gly Thr Val Ala Ala Leu Asn Asn Ser Thr Gly Val Leu Gly Val
 1               5                  10                  15

<210> SEQ ID NO 14
<211> LENGTH: 15
<212> TYPE: PRT
<213> ORGANISM: Artificial Sequence
<220> FEATURE:
<223> OTHER INFORMATION: peptide variant based on P1 sequence

<400> SEQUENCE: 14
```

```
Gly Thr Val Ala Ala Leu Asp Asn Ser Thr Gly Val Leu Gly Val
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: alanine substituted peptide of P1 region

<400> SEQUENCE: 15

Asn Gly Ile Glu Trp Ala Ile Ala Asn Asn Met Asp Val Ile Asn
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: substituted peptide of P1 region

<400> SEQUENCE: 16

Asn Gly Ile Glu Trp Ala Ile Ala Asn Asn Met Asp Val Ala Asn
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: substituted peptide of P1 region

<400> SEQUENCE: 17

Asn Gly Ile Glu Trp Ala Ile Ala Asn Asn Met Ala Val Ile Asn
1               5                   10                  15

<210> SEQ ID NO 18
<211> LENGTH: 275
<212> TYPE: PRT
<213> ORGANISM: Bacillus subtilis

<400> SEQUENCE: 18

Ala Gln Ser Val Pro Tyr Gly Ile Ser Gln Ile Lys Ala Pro Ala Leu
1               5                   10                  15

His Ser Gln Gly Tyr Thr Gly Ser Asn Val Lys Val Ala Val Ile Asp
                20                  25                  30

Ser Gly Ile Asp Ser Ser His Pro Asp Leu Asn Val Arg Gly Gly Ala
            35                  40                  45

Ser Phe Val Pro Ser Glu Thr Asn Pro Tyr Gln Asp Gly Ser Ser His
        50                  55                  60

Gly Thr His Val Ala Gly Thr Ile Ala Ala Leu Asn Asn Ser Ile Gly
65              70                  75                  80

Val Leu Gly Val Ser Pro Ser Ala Ser Leu Tyr Ala Val Lys Val Leu
                85                  90                  95

Asp Ser Thr Gly Ser Gly Gln Tyr Ser Trp Ile Ile Asn Gly Ile Glu
            100                 105                 110

Trp Ala Ile Ser Asn Asn Met Asp Val Ile Asn Met Ser Leu Gly Gly
        115                 120                 125

Pro Thr Gly Ser Thr Ala Leu Lys Thr Val Val Asp Lys Ala Val Ser
    130                 135                 140

Ser Gly Ile Val Val Ala Ala Ala Ala Gly Asn Glu Gly Ser Ser Gly
```

```
                145                 150                 155                 160
Ser Thr Ser Thr Tyr Gly Tyr Pro Ala Lys Tyr Pro Ser Thr Ile Ala
                165                 170                 175

Val Gly Ala Val Asn Ser Ser Asn Gln Arg Ala Ser Phe Ser Ser Ala
                180                 185                 190

Gly Ser Glu Leu Asp Val Met Ala Pro Gly Val Ser Ile Gln Ser Thr
            195                 200                 205

Leu Pro Gly Gly Thr Tyr Gly Ala Tyr Asn Gly Thr Ser Met Ala Thr
        210                 215                 220

Pro His Val Ala Gly Ala Ala Ala Leu Ile Leu Ser Lys His Pro Thr
225                 230                 235                 240

Trp Thr Asn Ala Gln Val Arg Asp Arg Leu Glu Ser Thr Ala Thr Tyr
                245                 250                 255

Leu Gly Asn Ser Phe Tyr Tyr Gly Lys Gly Leu Ile Asn Val Gln Ala
                260                 265                 270

Ala Ala Gln
        275

<210> SEQ ID NO 19
<211> LENGTH: 15
<212> TYPE: PRT
<213> ORGANISM: Artificial Sequence
<220> FEATURE:
<223> OTHER INFORMATION: P1 peptide variant

<400> SEQUENCE: 19

Ala Gly Ile Glu Trp Ala Ile Ala Asn Asn Met Asp Val Ile Asn
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: P1 peptide variant

<400> SEQUENCE: 20

Asn Ala Ile Glu Trp Ala Ile Ala Asn Asn Met Asp Val Ile Asn
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: P1 peptide variant

<400> SEQUENCE: 21

Asn Gly Ala Glu Trp Ala Ile Ala Asn Asn Met Asp Val Ile Asn
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: P1 peptide variant

<400> SEQUENCE: 22

Asn Gly Ile Ala Trp Ala Ile Ala Asn Asn Met Asp Val Ile Asn
1               5                   10                  15
```

```
<210> SEQ ID NO 23
<211> LENGTH: 15
<212> TYPE: PRT
<213> ORGANISM: Artificial Sequence
<220> FEATURE:
<223> OTHER INFORMATION: P1 peptide variant

<400> SEQUENCE: 23

Asn Gly Ile Glu Ala Ala Ile Ala Asn Asn Met Asp Val Ile Asn
 1               5                  10                  15

<210> SEQ ID NO 24
<211> LENGTH: 15
<212> TYPE: PRT
<213> ORGANISM: Artificial Sequence
<220> FEATURE:
<223> OTHER INFORMATION: P1 peptide variant

<400> SEQUENCE: 24

Asn Gly Ile Glu Trp Ala Ala Ala Asn Asn Met Asp Val Ile Asn
 1               5                  10                  15

<210> SEQ ID NO 25
<211> LENGTH: 15
<212> TYPE: PRT
<213> ORGANISM: Artificial Sequence
<220> FEATURE:
<223> OTHER INFORMATION: P1 peptide variant

<400> SEQUENCE: 25

Asn Gly Ile Glu Trp Ala Ile Ala Asn Asn Met Asp Val Ile Asn
 1               5                  10                  15

<210> SEQ ID NO 26
<211> LENGTH: 15
<212> TYPE: PRT
<213> ORGANISM: Artificial Sequence
<220> FEATURE:
<223> OTHER INFORMATION: P1 peptide variant

<400> SEQUENCE: 26

Asn Gly Ile Glu Trp Ala Ile Ala Ala Asn Met Asp Val Ile Asn
 1               5                  10                  15

<210> SEQ ID NO 27
<211> LENGTH: 15
<212> TYPE: PRT
<213> ORGANISM: Artificial Sequence
<220> FEATURE:
<223> OTHER INFORMATION: P1 peptide variant

<400> SEQUENCE: 27

Asn Gly Ile Glu Trp Ala Ile Ala Asn Ala Met Asp Val Ile Asn
 1               5                  10                  15

<210> SEQ ID NO 28
<211> LENGTH: 15
<212> TYPE: PRT
<213> ORGANISM: Artificial Sequence
<220> FEATURE:
<223> OTHER INFORMATION: P1 peptide variant

<400> SEQUENCE: 28

Asn Gly Ile Glu Trp Ala Ile Ala Asn Asn Ala Asp Val Ile Asn
 1               5                  10                  15

<210> SEQ ID NO 29
```

```
<211> LENGTH: 15
<212> TYPE: PRT
<213> ORGANISM: Artificial Sequence
<220> FEATURE:
<223> OTHER INFORMATION: P1 peptide variant

<400> SEQUENCE: 29

Asn Gly Ile Glu Trp Ala Ile Ala Asn Asn Met Asp Ala Ile Asn
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: P1 peptide variant

<400> SEQUENCE: 30

Asn Gly Ile Glu Trp Ala Ile Ala Asn Asn Met Asp Val Ile Ala
1               5                   10                  15

<210> SEQ ID NO 31
<211> LENGTH: 275
<212> TYPE: PRT
<213> ORGANISM: Artificial Sequence
<220> FEATURE:
<223> OTHER INFORMATION: conserved subtilisin sequences from Bacillus
      amyloliquefaciens and Bacillus lentus
<220> FEATURE:
<221> NAME/KEY: VARIANT
<222> LOCATION: (1)...(275)
<223> OTHER INFORMATION: Xaa = Any Amino Acid or no Amino Acid

<400> SEQUENCE: 31

Ala Gln Ser Val Pro Xaa Gly Xaa Xaa Xaa Xaa Xaa Ala Pro Ala Xaa
1               5                   10                  15

His Xaa Xaa Gly Xaa Thr Gly Ser Xaa Val Lys Val Ala Val Xaa Asp
            20                  25                  30

Xaa Gly Xaa Xaa Xaa Xaa His Pro Asp Leu Xaa Xaa Xaa Gly Gly Ala
        35                  40                  45

Ser Xaa Val Pro Xaa Xaa Xaa Xaa Xaa Gln Asp Xaa Asn Xaa His
50                  55                  60

Gly Thr His Val Ala Gly Thr Xaa Ala Ala Leu Asn Asn Ser Ile Gly
65                  70                  75                  80

Val Leu Gly Val Ala Pro Ser Ala Xaa Leu Tyr Ala Val Lys Val Leu
                85                  90                  95

Gly Ala Xaa Gly Ser Gly Xaa Xaa Ser Xaa Leu Xaa Xaa Gly Xaa Glu
            100                 105                 110

Trp Ala Xaa Asn Xaa Xaa Xaa Xaa Val Xaa Asn Xaa Ser Leu Gly Xaa
            115                 120                 125

Pro Ser Xaa Ser Xaa Xaa Xaa Xaa Ala Xaa Xaa Xaa Xaa Xaa
            130                 135                 140

Xaa Gly Val Xaa Val Val Ala Ala Xaa Gly Asn Xaa Gly Xaa Xaa
145                 150                 155                 160

Xaa Xaa Xaa Xaa Xaa Xaa Tyr Pro Xaa Xaa Tyr Xaa Xaa Xaa Xaa Ala
                165                 170                 175

Val Gly Ala Xaa Asp Xaa Xaa Asn Xaa Xaa Ala Ser Phe Ser Xaa Xaa
            180                 185                 190

Gly Xaa Xaa Leu Asp Xaa Xaa Ala Pro Gly Val Xaa Xaa Gln Ser Thr
        195                 200                 205

Xaa Pro Gly Xaa Xaa Tyr Xaa Xaa Xaa Xaa Asn Gly Thr Ser Met Ala Xaa
```

-continued

```
            210                 215                 220
Pro His Val Ala Gly Ala Ala Leu Xaa Xaa Xaa Lys Xaa Xaa Xaa
225                 230                 235                 240

Trp Xaa Xaa Xaa Gln Xaa Arg Xaa Xaa Leu Xaa Asn Thr Xaa Xaa Xaa
                245                 250                 255

Leu Gly Xaa Xaa Xaa Xaa Tyr Gly Xaa Gly Leu Xaa Asn Xaa Xaa Ala
            260                 265                 270

Ala Xaa Xaa
        275
```

PROTEINS PRODUCING AN ALTERED IMMUNOGENIC RESPONSE AND METHODS OF MAKING AND USING THE SAME

This application claims the benefit of Provisional Application No. 60/278,459, filed Mar. 23, 2001.

BACKGROUND OF THE INVENTION

Proteins used in industrial, pharmaceutical and commercial applications are of increasing prevalence. Individuals exposed to proteins may become sensitized thereto, whereupon subsequent exposure may cause allergic reactions. For example, some proteases may cause hypersensitivity reactions in certain individuals. As a result, despite the usefulness of proteases in industry, e.g., in laundry detergents, cosmetics, textile treatment etc., and the extensive research performed in the field to provide improved proteases which have, for example, more effective stain removal under detergency conditions; the use of proteases in industry has been problematic.

Much work has been done to alleviate these problems. Among the strategies explored to reduce immunogenic potential of protease use have been improved production processes which reduce potential contact by controlling and minimizing workplace concentrations of dust particles or aerosol carrying airborne protease, improved granulation processes which reduce the amount of dust or aerosol actually produced from the protease product, and improved recovery processes to reduce the level of potentially allergenic contaminants in the final product. However, efforts to reduce the allergenicity of protease, per se, have been relatively unsuccessful. Alternatively, efforts have been made to mask epitopes in protease which are recognized by immunoglobulin E (IgE) in hypersensitive individuals (PCT Publication No. WO 92/10755) or to enlarge or change the nature of the antigenic determinants by attaching polymers or peptides/proteins to the problematic protease.

When an adaptive immune response occurs in an exaggerated or inappropriate form, the individual experiencing the reaction is said to be hypersensitive. Hypersensitivity reactions are the result of normally beneficial immune responses acting inappropriately and sometimes cause inflammatory reactions and tissue damage. They can be provoked by many antigens; and the cause of a hypersensitivity reaction will vary from one individual to the next. Hypersensitivity does not normally manifest itself upon first contact with the antigen, but usually appears upon subsequent contact. One form of hypersensitivity occurs when an IgE response is directed against innocuous environmental antigens, such as pollen, dust-mites or animal dander. The resulting release of pharmacological mediators by IgE-sensitized mast cells produces an acute inflammatory reaction with symptoms such as asthma or rhinitis.

Nonetheless, a strategy comprising modifying the IgE sites will not generally be successful in preventing the cause of the initial sensitization reaction. Accordingly, such strategies, while perhaps neutralizing or reducing the severity of the subsequent hypersensitivity reaction, will not reduce the number or persons actually sensitized. For example, when a person is known to be hypersensitive to a certain antigen, the general manner of dealing with such a situation is to isolate the hypersensitive person from the antigen as completely as possible. Indeed, any other course of action could be dangerous to the health of the hypersensitive individual. Thus, while reducing the danger of a specific protein for a hypersensitive individual is important, for industrial purposes it would be far more valuable to reduce or eliminate the capability of the protein to initiate the hypersensitivity reaction in the first place.

T-lymphocytes (T-cells) are key players in the induction and regulation of immune responses and in the execution of immunological effector functions. Specific immunity against infectious agents and tumors is known to be dependent on these cells and they are believed to contribute to the healing of injuries. On the other hand, failure to control these responses can lead to auto aggression. In general, antigen is presented to T-cells in the form of antigen presenting cells which, through a variety of cell surface mechanisms, capture and display antigen or partial antigen in a manner suitable for antigen recognition by the T-cell. Upon recognition of a specific epitope by the receptors on the surface of the T-cells (T-cell receptors), the T-cells begin a series of complex interactions, including proliferation, which result in the production of antibody by B-cells. While T-cells and B-cells are both activated by antigenic epitopes which exist on a given protein or peptide, the actual epitopes recognized by these mononuclear cells are generally not identical. In fact, the epitope which activates a T-cell to initiate the creation of immunologic diversity is quite often not the same epitope which is later recognized by B-cells in the course of the immunologic response. Thus, with respect to hypersensitivity, while the specific antigenic interaction between the T-cell and the antigen is a critical element in the initiation of the immune response to antigenic exposure, the specifics of that interaction, i.e., the epitope recognized, is often not relevant to subsequent development of a full blown allergic reaction mediated by IgE antibody.

PCT Publication No. WO 96/40791 discloses a process for producing polyalkylene oxide-protease conjugates with reduced allergenicity using polyalkylene oxide as a starting material.

PCT Publication No. WO 97/30148 discloses a polypeptide conjugate with reduced allergenicity which comprises one polymeric carrier molecule having two or more polypeptide molecules coupled covalently thereto.

PCT Publication No. WO 96/17929 discloses a process for producing polypeptides with reduced allergenicity comprising the step of conjugating from 1 to 30 polymolecules to a parent polypeptide.

PCT Publication No. WO 92/10755 discloses a method of producing protein variants evoking a reduced immunogenic response in animals. In this application, the proteins of interest, a series of proteases and variants thereof, were used to immunize rats. The sera from the rats was then used to measure the reactivity of the polyclonal antibodies already produced and present in the immunized sera to the protein of interest and variants thereof. From these results, it was possible to determine whether the antibodies in the preparation were comparatively more or less reactive with the protein and its variants, thus permitting an analysis of which changes in the protein are likely to neutralize or reduce the ability of the Ig to bind. From these tests on rats, the conclusion was arrived at that changing any of subtilisin 309 residues corresponding to 127, 128, 129, 130, 131, 151, 136, 151, 152, 153, 154, 161, 162, 163, 167, 168, 169, 170, 171, 172, 173, 174, 175, 176, 186, 193, 194, 195, 196, 197, 247, 251, 261 will result in a change in the immunological potential.

PCT Publication No. WO 94/10191 discloses low allergenic proteins comprising oligomeric forms of the parent monomeric protein, wherein the oligomer has substantially retained its activity.

PCT Publication No. WO 99/49056 discloses a plurality of subtilisin variants having amino acid substitutions in a defined epitope region. However, due to the large number of variants disclosed, one of skill in the art is presented with a problem with respect to identifying an optimal protease product for personal care or other human applications which has lowered immunogenic effect.

PCT Publication No. WO 01/07578 discloses a plurality of subtilisin variants having amino acid substitutions in defined epitope regions. However, due to the large number of variants disclosed, one of skill in the art is presented with a problem with respect to identifying an optimal protease product for personal care or other human applications which has lowered immunogenic effect.

While some studies have provided methods of reducing the allergenicity of certain proteins and identification of epitopes which cause allergic reactions in some individuals, the assays used to identify these epitopes generally involve measurement of IgE and IgG antibody in blood sera previously exposed to the antigen. However, once an Ig reaction has been initiated, sensitization has already occurred. Accordingly, there is a need to identify proteins which produce an enhanced immunologic response, and a need to produce proteins which produce a reduced immunologic response. The present invention meets these and other needs.

SUMMARY OF THE INVENTION

The methods and compositions provided herein are useful in forming hypo-allergenic compositions. As used herein, "hypo-allergenic" means the composition produces a lesser immunogenic response than the same composition with the precursors of the proteins of the present invention. As used herein, "hyper-allergenic" means the composition produces a greater immunogenic response than the same composition with the precursors of the proteins of the present invention.

The compositions of the invention may be embodied in, for example, cleaning compositions, peptide hydrolysis products, cosmetic formulations, compositions for skin, hair and oral care, pharmaceuticals such as blood clot removal products, research products such as enzymes and therapeutics including vaccines.

In one aspect of the invention, a protease of interest is selected and provided herein. The protease of interest is preferably one having a T-cell epitope and is then varied as described below. However, protease of interest may also be selected based on naturally occurring properties and not altered.

In one aspect of the invention provided herein is a variant of a protease of interest comprising a T-cell epitope. The variant differs from the protease of interest by having an altered T-cell epitope such that said variant and said protease of interest produce different (e.g., increased, reduced or eliminated) immunogenic responses in a human.

The protease can be any protease of interest. In one aspect, the protease is a subtilisin protease. In preferred embodiments, the protease of interest and the variant of said protease of interest each comprise at least some of the same activity. For example, if a variant of a protease is provided, said variant will produce an altered immunogenic response, but will retain detectable, and preferably comparable, protease activity and stability.

Wherein a variant of a protease of interest is provided, the T-cell epitope may be altered in a number of ways including amino acid substitutions, deletions, additions and combinations thereof. Preferably, the T-cell epitope is altered by having amino acid substitutions. In one embodiment herein, the amino acid substitutions are made to corresponding amino acids of a homolog of the protease of interest, wherein the homolog does not comprise the same T-cell epitope in the corresponding position as the protease of interest. In one aspect, the terminal portion of the protease of interest comprising at least one T-cell epitope is replaced with a corresponding terminal portion of the homolog of the protease of interest, wherein the replacement produces said different immunogenic response.

In another embodiment provided herein, the nucleic acids encoding the proteases producing the desired immunogenic response are provided. Moreover, the invention includes expression vectors and host cells comprising the nucleic acids provided herein. Once the proteases and variants thereof of the present invention are identified, substantially homologous sequences of or those sequences which hybridize to the proteases and variants can be identified and are provided herein. Homologous is further defined below, and can refer to similarity or identity, with identity being preferred. Preferably, the homologous sequences are amino acid sequences or nucleic acids encoding peptides having the activity of the proteases and variants provided herein.

In yet another aspect of the invention is a protease having an altered immunogenic response. In one embodiment, the protease or variant of interest comprises an epitope determined by the method which comprises (a) obtaining from a single blood source a solution of dendritic cells and a solution of naïve CD4+ and/or CD8+ T-cells; (b) promoting differentiation in said solution of dendritic cells; (c) combining said solution of differentiated dendritic cells and said naïve CD4+ and/or CD8+ T-cells with said protein; and (d) measuring the proliferation of T-cells in said step (c).

The present inventors have discovered that those serine proteases commonly known as subtilisins, including subtilisin BPN', have prominent epitope regions at amino acid positions 70–84, a first epitope region, and 109–123, a second epitope region, corresponding to BPN'. The present inventors have herein genetically redesigned such subtilisin to alter, e.g. alleviate the immunological properties attributed to these epitope regions. In doing so, the present inventors have discovered subtilisins which evoke a decreased immunological response yet maintain their activity as an efficient protease. In addition, the present inventors have discovered subtilisins which evoke such a decreased immunological response and are thermally and pH stable. Accordingly, the present proteases are suitable for use in several types of compositions including, but not limited to, pharmaceutical, laundry, dish, hard surface, skin care, hair care, beauty care, oral care, and contact lens compositions.

The present inventors have discovered that those serine proteases commonly known as subtilisins, including subtilisin BPN', have prominent epitope regions at amino acid positions 70–84, a first epitope region, and 109–123, a second epitope region, corresponding to BPN'. The present inventors have herein genetically redesigned such subtilisin to alter, e.g. alleviate the immunogenic properties attributed to these epitope regions. In doing so, the present inventors have discovered subtilisins which evoke a decreased immunogenic response yet maintain their activity as an efficient protease. In addition, the present inventors have discovered subtilisins which evoke such a decreased immunogenic response and are thermally and pH stable. Accordingly, the present proteases are suitable for use in several types of compositions including, but not limited to, pharmaceutical, laundry, dish, hard surface, skin care, hair care, beauty care, oral care, and contact lens compositions.

In one embodiment, the inventors have discovered variants of a protease of interest, wherein said variant differs from the protease of interest by having an altered T-cell epitope such that the variant and the protease of interest produce different immunogenic responses in a human. The T-cell epitope of interest includes an amino acid residue position substitution selected from the positions consisting of the residues corresponding to 76, 79 and 122 of *Bacillus amyloliquefaciens* subtilisin. In another embodiment, the T-cell of interest includes an amino acid residue position selected from the group consisting of 76 and 122. In another embodiment, the T-cell of interest includes an amino acid residue position substitution at position 122 and at one or both of positions 76 and 79. The immunogenic response produced by the variant, in one embodiment, is less than the immunogenic response produced by the protease of interest. In another embodiment, the immunogenic response produced by the variant is greater than the immunogenic response produced by the protease of interest. Additional substitutions at one or more of the positions 3, 31, 40, 41, 111, 147, 218, 206, and/or 217 can also be incorporated. Additional substitutions at one or more of the positions 216, 181, 101, 215, 216, 217, 247, 46, 154, 128, 182, 107, 250, 254, 258, 50, 47, 48, 182, 183, 185, 248 and/or 262 can also be incorporated. Specific substitution sets incorporating various permutations of the above residues have also been discovered. Specific substitution sets incorporating various permutations of the above residues have also been discovered.

In another embodiment, the inventors have discovered a method for reducing the immunogenic response of a protease comprising obtaining a precursor protease; and obtaining a variant of said precursor protease, the variant having at least one T-cell epitope of the precursor protease wherein the variant exhibits an altered immunogenic response which differs from the immunogenic response of the precursor protease.

In another embodiment, the inventors have discovered a nucleic acid encoding the variant proteases claimed herein, expression vectors, host cells transformed with the expression vectors, cleaning compositions, oral cleaning compositions, pharmaceutical compositions, and skin care compositions (including cosmetically acceptable carriers, skin care actives, humectants, emollients, emulsifiers, polymeric thickening agents and silicone oils).

Other aspects of the invention will be understood by the skilled artisan by the following description.

BRIEF DESCRIPTION OF THE DRAWINGS

FIGS. 1A, B1, B2 and B3 illustrate the DNA (SEQ ID:NO 1) and amino acid (SEQ ID: NO 2) sequence for *Bacillus amyloliquefaciens* subtilisin (BPN') and a partial restriction map of this gene.

FIG. 2 illustrates the conserved amino acid residues (SEQ ID NO: 31) among subtilisins from *Bacillus amyloliquefaciens* (SEQ ID:NO 3) and *Bacillus lentus* (wild-type) (SEQ ID:NO 4).

FIGS. 3A and 3B illustrate an amino acid sequence alignment of subtilisin type proteases from *Bacillus amyloliquefaciens* (BPN') (SEQ ID NO: 3), *Bacillus subtilis* (SEQ ID NO: 18), *Bacillus licheniformis* (SEQ ID:NO 5) and *Bacillus lentus* (SEQ ID NO: 4. The symbol * denotes the absence of specific amino acid residues as compared to subtilisin BPN'.

FIG. 4a illustrates the amino acid sequence of the precursor protease P1 (SEQ ID NO: 3).

FIG. 4b illustrates the per cent responders to the 70–84 BPN' peptide and various variants (n=20).

FIG. 6 illustrates the 13 peptide sequences (SEQ ID NOs: 15–17 and 19–30) having the differing alanine substitutions within the epitope extending from residue 109 to 123 used to determine the altered immunogenic response of human subjects to the subject peptides.

FIG. 7a illustrates the SI of several human subjects as exposed to the peptide sequences of FIG. 6.

FIG. 10 illustrates the hydrolysis of a 5 mg/ml dimethyl casein substrate solution at pH 7.5 as indicated by the change in substrate absorbance by different concentrations of the subtilisin variants (P1-◇-; -□-LAP2; -Δ-LAP3; and -x-LAP4).

FIG. 15 illustrates the change in enzyme half-life over the temperature range of 42–56° C. as a measure of the thermal stability of the various protease variants in 50 mM PIPES (pH 6.5)(P1-◇-; -□-LAP2; -Δ-LAP3; and -x-LAP4).

DETAILED DESCRIPTION OF THE INVENTION

Figure 4B:
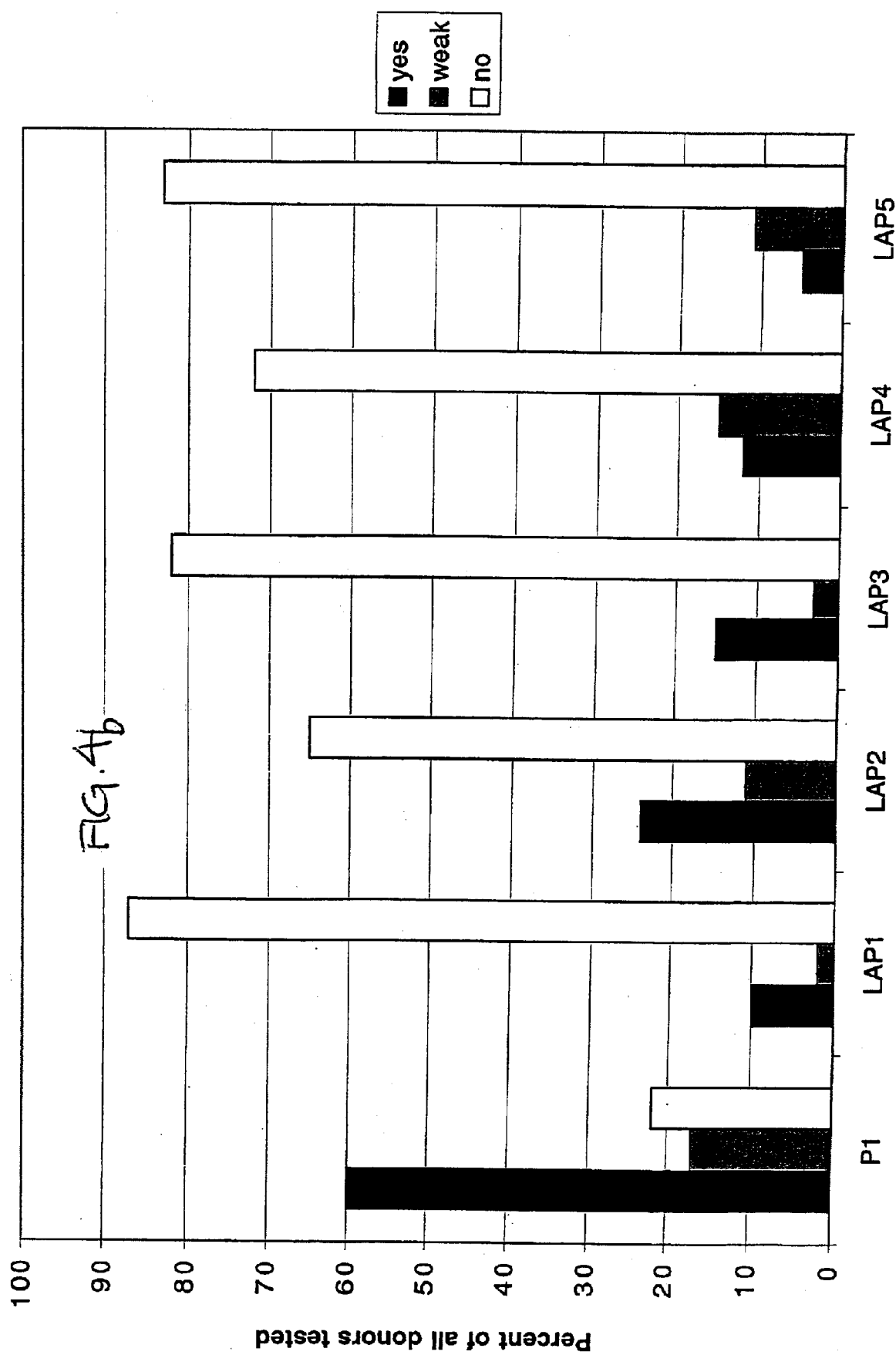
FIG. 4b illustrates the in vitro response to subtilisin protein variant P1 (BPN'-Y217L) in comparison with variants LAP2 (BPN'-Y217L/I79A/I122A), LAP3 (BPN'-Y217L/N76D/I122A) and LAP4 (BPN'-Y217L/N76D/I79A/I122A).

In one aspect of the invention, the objective is to secure a variant protease having altered immunogenic response and allergenic potential as compared to the precursor protease or protease of interest, since decreasing such potential enables safer use of the enzyme. While the instant invention is useful to alter the immunogenic response potential, the mutations specified herein may be utilized in combination with mutations known in the art to effect altered thermal stability and/or altered substrate specificity, modified activity, increased specific activity, altered alkaline stability or altered B-cell epitope as compared to the precursor.

According to the present invention, a protease variant is provided having an altered immunogenic response, the variant comprising a T-cell epitope, wherein the variant of the peptide of interest differs from the precursor peptide or peptide of interest by having an altered T-cell epitope, such that the variant peptide of interest produces different immunogenic responses in a human. It is contemplated by the inventors that an altered immunogenic response includes altered allergenicity, including both increased or decreased immunogenic response. The T-cell epitope may include a substitution of an amino acid selected from those residues within the identified epitope. The variant protease of the present invention, including such reduced immunogenic response substitutions may be characterized by activity comparable to that of the precursor protease, site mutation variants that do not produce an immunogenic response or hybrid protease variants.

Accordingly the present invention also includes a method for altering, e.g., increasing or reducing the immunogenic response of a protease comprising: obtaining a precursor protease; and modifying the precursor protease to obtain a variant or derivative of said precursor protease, the variant having at least one altered T-cell epitope of the precursor protease. In addition, the variant is characterized by exhibiting an altered immunogenic response which differs from the immunogenic response of the precursor protease. As described elsewhere in this application, there are at least two T-cell epitopes in subtilisin proteases, a first one corresponding to residues 70–84 of the *Bacillus amyloliquefaciens*, and a second epitope corresponding to residues 109 to 123 of the *B. amyloliquefaciens*. The method may further include determining the residues which increase or decrease such immunogenic response. These residues can be determined by peptide screening techniques described elsewhere in this application. In one embodiment, the variant protease comprises an amino acid substitution at a group of positions corresponding to the amino acid positions 76, 79 and 122 of *B. amyloliquefaciens*, said substitutions being within at least one of said epitopes. The resulting variant exhibits an altered immunogenic response as compared to that of the precursor protease.

It is understood that the terms protein, polypeptide and peptide are sometimes used herein interchangeably. Wherein a peptide is a portion of protein, the skilled artisan can understand this by the context in which the term is used.

In one embodiment, the peptide having an altered immunogenic response, e.g., increased immunogenic or decrease immunogenic response, is derived from a protease of interest. This protease of interest can be a wild-type, mutated variant, conjugated variant, hybrid variant having amino acid deletions, substitutions or additions in the epitope of interest, which can cause sensitization in an individual or sampling of individuals. The epitope can be identified by an assay which identifies epitopes and non-epitopes as follows: differentiated dendritic cells are combined with naïve human CD4+ and/or CD8+ T-cells and with a peptide of interest. More specifically, a reduced immunogenic response peptide of interest can be provided wherein a T-cell epitope is recognized comprising the steps of: (a) obtaining from a single blood source a solution of dendritic cells and a solution of naïve CD4+ and/or CD8+ T-cells; (b) promoting differentiation in said solution of dendritic cells; (c) combining said solution of differentiated dendritic cells and said naïve CD4+ and/or CD8+ T-cells with a peptide of interest; (d) measuring the proliferation of T-cells in said step (c).

In an embodiment of the invention, a series of peptide oligomers which correspond to all or part of the protease of interest are prepared. For example, a peptide library is produced covering the relevant portion or all of the protein. In one embodiment, the manner of producing the peptides is to introduce overlap into the peptide library, for example, producing a first peptide corresponds to amino acid sequence 1–10 of the subject protein, a second peptide corresponds to amino acid sequence 4–14 of the subject protein, a third peptide corresponds to amino acid sequence 7–17 of the subject protein, a fourth peptide corresponds to amino acid sequence 10–20 of the subject protein etc. until representative peptides corresponding to the entire molecule are created. By analyzing each of the peptides individually in the assay provided herein, it is possible to precisely identify the location of epitopes recognized by T-cells. In the example above, the greater reaction of one specific peptide than its neighbors' will facilitate identification of the epitope anchor region to within three amino acids. After determining the location of these epitopes, it is possible to alter the amino acids within each epitope until the peptide produces a different T-cell response from that of the original protein. Moreover, proteins may be identified herein which have desired low T-cell epitope potency which may be used in their naturally occurring forms.

"Antigen presenting cell" as used herein means a cell of the immune system which present antigen on their surface which is recognizable by receptors on the surface of T-cells. Examples of antigen presenting cells are dendritic cells, interdigitating cells, activated B-cells and macrophages.

"T-cell proliferation" as used herein means the number of T-cells produced during the incubation of T-cells with the antigen presenting cells, with or without antigen.

"Baseline T-cell proliferation" as used herein means T-cell proliferation which is normally seen in an individual in response to exposure to antigen presenting cells in the absence of peptide or protein antigen. For the purposes herein, the baseline T-cell proliferation level was determined on a per sample basis for each individual as the proliferation of T-cells in response to antigen presenting cells in the absence of antigen.

"T-cell epitope" means a feature of a peptide or protein which is recognized by a T-cell receptor in the initiation of an immunologic response to the peptide comprising that antigen. Recognition of a T-cell epitope by a T-cell is generally believed to be via a mechanism wherein T-cells recognize peptide fragments of antigens which are bound to class I or class II major histocompatability (MHC) molecules expressed on antigen-presenting cells (see e.g., Moeller, G. ed., "Antigenic Requirements for Activation of MHC-Restricted Responses," *Immunological Review,* Vol. 98, p. 187 (Copenhagen; Munksgaard) (1987).

"Sample" as used herein comprises mononuclear cells which are naïve, i.e., not sensitized, to the antigen in question.

"Homolog" as used herein means a protein or enzyme which has similar catalytic action, structure and/or use as the protein of interest. For purposes of this invention, a homolog and a protein of interest are not necessarily related evolutionarily, e.g., same functional protein from different species. It is desirable to find a homolog that has a tertiary and/or primary structure similar to the protein of interest as replacement of the epitope in the protein of interest with an analogous segment from the homolog will reduce the disruptiveness of the change. Thus, closely homologous enzymes will provide the most desirable source of epitope substitutions. Alternatively, if possible, it is advantageous to look to human analogs for a given protein. For example, substituting a specific epitope in a bacterial subtilisin with a sequence from a human analog to subtilisin (i.e., human subtilisin) should result in a reduced immunogenic response in the bacterial protein.

An "analogous" sequence may be determined by ensuring that the replacement amino acids show a similar function, the tertiary structure and/or conserved residues to the amino acids in the protein of interest at or near the epitope. Thus, where the epitope region contains, for example, an alpha-helix or a beta-sheet structure, the replacement amino acids should maintain that specific structure.

The epitopes determined or identified can then be modified to alter, e.g., increase or reduce the immunologic potential of the protein of interest. In one embodiment, the epitope to be modified produces a level of T-cell proliferation of greater than three times the baseline T-cell proliferation in a sample. When modified, the epitope produces less than three times the baseline proliferation, preferably less than two times the baseline proliferation and most preferably less than or substantially equal to the baseline proliferation in a sample. In another embodiment, the epitope to be modified produces a level of T-cell proliferation of less than three times the baseline T-cell proliferation in a sample. When modified, the epitope produces greater than three times the baseline proliferation, preferably greater than two times the baseline proliferation and most preferably greater than or substantially equal to the baseline proliferation in a sample.

The epitope can be modified in a variety of ways, for example: (a) the amino acid sequence of the epitope can be substituted with an analogous sequence from a human homolog to the protein of interest; (b) the amino acid sequence of the epitope can be substituted with an analogous sequence from a non-human homolog to the protein of interest, which analogous sequence produces a lesser immunogenic, e.g., allergenic, response due to T-cell epitope recognition than that of the protein of interest; (c) the amino acid sequence of the epitope can be substituted with a sequence which substantially mimics the major tertiary structure attributes of the epitope, but which produces a lesser immunogenic, e.g., allergenic, response due to T-cell epitope recognition than that of the protein of interest; or (d) with any sequence which produces lesser immunogenic, e.g., allergenic, response due to T-cell epitope recognition than that of the protein of interest.

It should be appreciated that one of skill will readily recognize that epitopes can be modified in other ways depending on the desired outcome. For example, if altering an autoimmune response against self-antigens is desired, it is contemplated the amino acid sequence of an epitope will be substituted with amino acids that decrease or cause a shift in an inflammatory or other immune response.

The present invention extends to all proteins against which it is desired to modulate the immunogenic response. One of skill in the art will readily recognize the proteins and peptides of this invention are not necessarily native proteins and peptides. Indeed, in one embodiment of this invention, shuffled genes having an altered immunologic response is contemplated. For descriptions of gene shuffling and expression of such genes see, Stemmer, *Proc. Nat'l Acad. Sci. USA* 91:10747 (1994); Patten, et al., *Current Opinion in Biotechnol.* 8:724 (1997); Kuchner & Arnold, *Trends Biotechnol.* 15:523 (1997); Moore, et al., *J. Mol, Biol.* 272:336 (1997); Zhao, et al., *Nature Biotechnol.* 16:258 (1998); Giver, et al., *Proc. Nat'l Acad. Sci. USA* 95:12809 (1998); Harayama, *Trends Biotechnol.* 16:76 (1998); Lin, et al., *Biotechnol., Prog.* 15:467 (1999); and Sun, *J. Comput. Biol.* 6:77 (1999). Proteins can be altered to modulate the immunologic response to that protein.

Preferably, proteases according to the present invention are isolated or purified. By purification or isolation is meant that the protease is altered from its natural state by virtue of separating the protease from some or all of the naturally occurring constituents with which it is associated in nature. This may be accomplished by art recognized separation techniques such as ion exchange chromatography, affinity chromatography, hydrophobic separation, dialysis, protease treatment, ammonium sulphate precipitation or other protein salt precipitation, centrifugation, size exclusion chromatography, filtration, microfiltration, gel electrophoresis or separation on a gradient to remove whole cells, cell debris, impurities, extraneous proteins, or enzymes undesired in the final composition. It is further possible to then add constituents to the protease containing composition which provide additional benefits, for example, activating agents, anti-inhibition agents, desirable ions, compounds to control pH or other enzymes such as cellulase.

In addition to the above proteins and peptides, the present invention includes proteins or provide variant proteins that exhibit an altered immunogenic response, e.g., an increased or reduced immunogenic response. Proteins, e.g. proteases, exhibit increased immunogenic response when the T-cell response they evoke is greater than that evoked by a parental (precursor) protein. The net result of this higher response is an increase in the antibodies directed against the variant protein. Proteins exhibit a reduced immunogenic response when the T-cell response they evoke is less than that evoked by a parental protein. The net result of this lower response is lack of antibodies directed against the variant protein.

Exemplary assays useful in ascertaining the reduced immunogenic response of the variant proteins include, but are not limited to in vivo assays (HLA-DR3/DQ2 mouse T cell responses, and in vitro assays (human peripheral blood mononuclear cells (PBMC) to Protease 1 (P1 is a BPN'-Y217L protease) and its variants. In vivo assays useful in ascertaining the reduced immunogenic response include, but are not limited to the use of transgenic mice, for example, rats (Taurog et al., Immunol. Rev., 169: 209–223 (1999), rabbits or pigs. A preferred transgenic mice model for testing modified proteins of interest and variants in vivo, determining a reduced immunogenic response, is the HLA-DR3/DQ2 mouse model. This mouse model expresses a haplotype common in the general human population. It expresses HLA-DR3 on B cell and macrophages in the secondary immune organs. It may upregulate HLA-DR expression on activated T cells in a manner analogous to human T cells. It expresses HLA-DQ2 at lower levels than HLA-DR, once again consistent with expression patterns for HLA molecules in humans. The protease epitopes of interest were shown to bind to HLA-DQ2 by cell surface binding analyses.

The inventors are aware of differences between this mouse model and the HLA transgenic mouse models described in the literature. The HLA mice used by the present inventors express HLA-DR and -DQ in a manner analogous to that seen in humans, that is, the expression of HLA-DQ is quite low, and can not be upregulated by LPS-mediated activation of B cells. This is in stark contrast to other transgenic animals that have been selected to express high levels of a single HLA transgene. This mouse has been crossed onto a murine I-Ab-deficient mouse that eliminates the expression of the endogenous I-Aab heterdimer, see Grusby et al., Proc. Natl. Acad. Sci, 90:3913–3917 (1993), which corresponds to human DQ. These mice still express mouse MHC class II I-E beta chain. This molecule can pair with the HLA-DR alpha chain to create a mixed dimer that is likely expressed at high levels on antigen-presenting cells. Other HLA transgenic mice have been reported and could be used in a similar manner to evaluate the potential immune responses to those Class II haplotypes, for example see Herman et al., J. Immunol. 163:6275–6282; Sonderstrup et al., Immunological Reviews 172: 335–343 (1999); Taneja and David, Immunological Reviews 169:67–79 (1999).

In addition to the altering; e.g., increasing or reducing the immunogenic response of an animal, such as a human, of naturally occurring amino acid sequences, this invention encompasses reducing the immunogenic response of a mutated protein, e.g., a protein or protease that has been altered to change the functional activity of the protein. In many instances, the mutation of proteins to e.g., increase activity, increase thermal stability, increase alkaline stability and/or oxidative stability, results in the incorporation of new T-cell epitope in the mutated protein. This invention determined the presence of new T-cell epitopes and determined substitute amino acids that will alter the immunogenic response of the mutated protein.

Although this invention encompasses the above proteins and many others, for the sake of simplicity, the following will describe particularly preferred embodiments of the invention, which involve the modification of protease. Proteases are carbonyl hydrolases which generally act to cleave peptide bonds of proteins or peptides. As used herein, "protease" means a naturally-occurring protease or a recombinant protease. Naturally-occurring proteases include, for example, a-aminoacylpeptide hydrolase, peptidylamino acid hydrolase, acylamino hydrolase, serine carboxypeptidase, metallocarboxypeptidase, thiol proteinase, carboxylproteinase and metalloproteinase. Serine, metallo, thiol and acid proteases are included, as well as endo and exo-proteases.

Figure 1B-2:
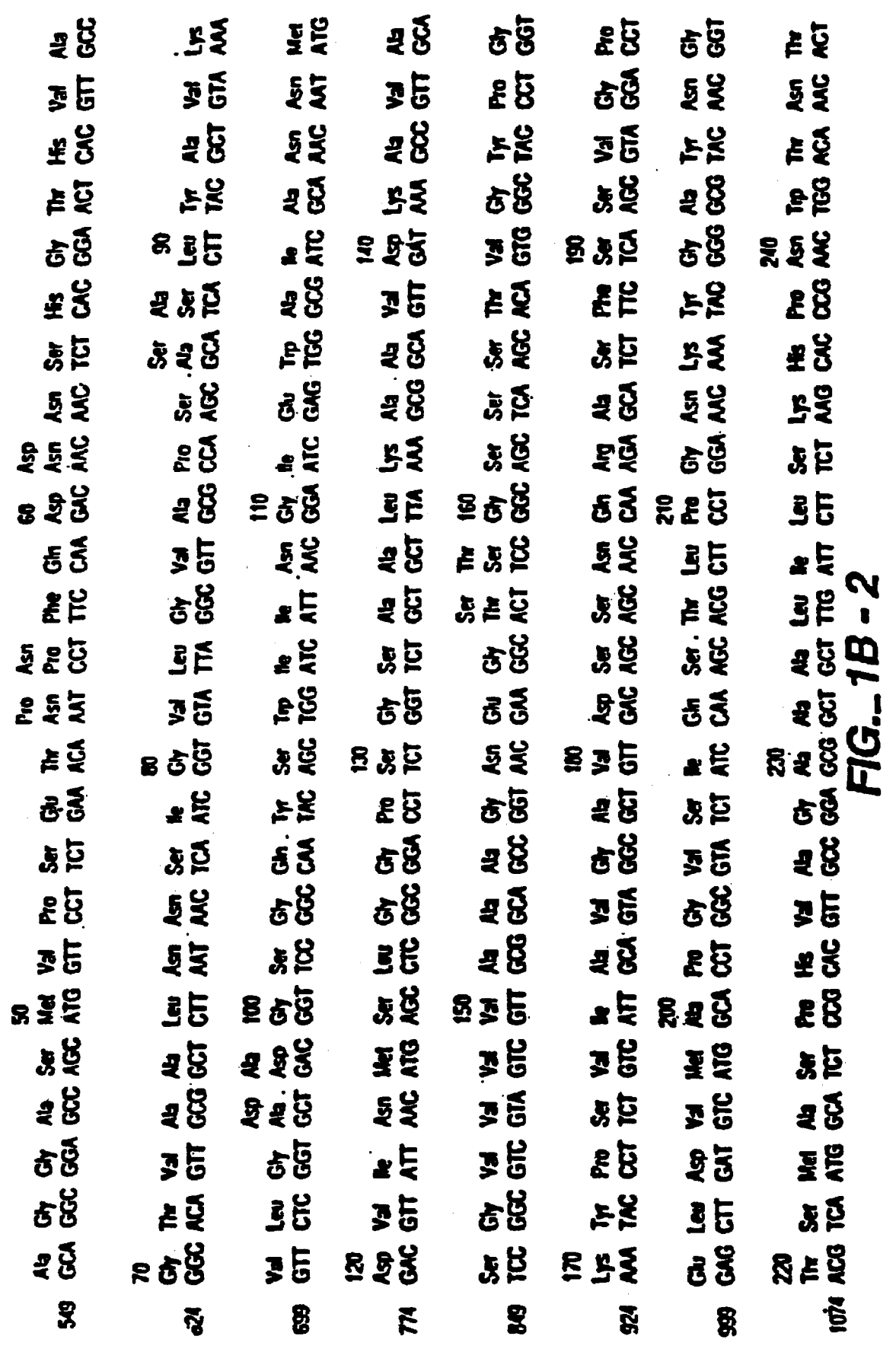

Subtilisins are bacterial or fungal proteases which generally act to cleave peptide bonds of proteins or peptides. As used herein, "subtilisin" means a naturally-occurring subtilisin or a recombinant subtilisin. A series of naturally-occurring subtilisins is known to be produced and often secreted by various microbial species. Amino acid sequences of the members of this series are not entirely homologous. However, the subtilisins in this series exhibit the same or similar type of proteolytic activity. This Glass of serine proteases shares a common amino acid sequence defining a catalytic triad which distinguishes them from the chymotrypsin related class of serine proteases. The subtilisins and chymotrypsin related serine proteases both have a catalytic triad comprising aspartate, histidine and serine. In the subtilisin related proteases the relative order of these amino acids, reading from the amino to carboxy terminus, is aspartate-histidine-serine. In the chymotrypsin related proteases, the relative order, however, is histidine-aspartate-serine. Thus, subtilisin herein refers to a serine protease having the catalytic triad of subtilisin related proteases. Examples include but are not limited to the subtilisins identified in FIG. 3 herein (SEQ ID NOs: 3–5, 18). Generally and for purposes of the present invention, numbering of the amino acids in proteases corresponds to the numbers assigned to the mature *Bacillus amyloliquefaciens* subtilisin sequence presented in FIG. 1 (SEQ ID NO: 2).

"Recombinant," "recombinant subtilisin" or "recombinant protease" refer to a subtilisin or protease in which the DNA sequence encoding the subtilisin or protease is modified to produce a variant (or mutant) DNA sequence which encodes the substitution, deletion or insertion of one or more amino acids in the naturally-occurring amino acid sequence. Suitable methods to produce such modification, and which may be combined with those disclosed herein, include those disclosed in U.S. Pat. No. 4,760,025 (US RE 34,606), U.S. Pat. No. 5,204,015 and U.S. Pat. No. 5,185,258.

"Non-human subtilisins" and the DNA encoding them may be obtained from many procaryotic and eucaryotic organisms. Suitable examples of procaryotic organisms include gram negative organisms such as *E. coli* or *Pseudomonas* and gram positive bacteria such as *Micrococcus* or *Bacillus*. Examples of eucaryotic organisms from which subtilisin and their genes may be obtained include yeast such as *Saccharomyces cerevisiae*, fungi such as *Aspergillus* sp.

"Human subtilisin" means proteins of human origin which have subtilisin type catalytic activity, e.g., the kexin family of human derived proteases. Additionally, derivatives or homologs of proteins provided herein, including those from non-human sources such as mouse or rabbit, which retain the essential activity of the peptide, such as the ability to hydrolyze peptide bonds and exhibits the altered immunogenic response as described elsewhere in this application, etc., have at least 50%, at least 65% and preferably at least 80%, more preferably at least 90%, and sometimes as much as 95, 97 or even 99% homology to the protease of interest. The essential activity of the homolog includes the ability to produce different immunogenic responses in a human. In one embodiment, the protease of interest is shown in the FIG. 4a.

The amino acid position numbers used herein refer to those assigned to the mature *Bacillus amyloliquefaciens* subtilisin sequence presented in FIG. 1 (SEQ ID NO: 2). The invention, however, is not limited to the mutation of this particular subtilisin but extends to precursor proteases containing amino acid residues at positions which are equivalent to the particular identified residues in *Bacillus amyloliquefaciens* subtilisin. For example, where the precursor protease is *Bacillus lentus* subtilisin, substitutions, deletions and/or insertions can be made at the equivalent amino acid residue in *B. lentus* corresponding to those listed above.

A residue (amino acid) of a precursor protease is equivalent to a residue of *Bacillus amyloliquefaciens* subtilisin if it is either homologous (i.e., corresponding in position in either primary or tertiary structure) or analogous to a specific residue or portion of that residue in *Bacillus amyloliquefaciens* subtilisin (i.e., having the same or similar functional capacity to combine, react, or interact chemically). "Corresponding" as used herein generally refers to an analogous position along the peptide.

In order to establish homology to primary structure, the amino acid sequence of a precursor protease is directly compared to the *Bacillus amyloliquefaciens* subtilisin primary sequence and particularly to a set of residues known to be invariant in subtilisins for which the sequence is known. For example, FIG. 2 herein shows the conserved residues as between *B. amyloliquefaciens* subtilisin and *B. lentus* subtilisin (SEQ ID NO: 31). After aligning the conserved residues, allowing for necessary insertions and deletions in order to maintain alignment (i.e., avoiding the elimination of conserved residues through arbitrary deletion and insertion), the residues equivalent to particular amino acids in the primary sequence of *Bacillus amyloliquefaciens* subtilisin are defined. Alignment of conserved residues preferably should conserve 100% of such residues. However, alignment of greater than 75% or as little as 50% of conserved residues is also adequate to define equivalent residues. Conservation of the catalytic triad, Asp32/His64/Ser221 should be maintained.

For example, the amino acid sequence of subtilisin from *Bacillus amyloliquefaciens, Bacillus subtilis, Bacillus licheniformis* (carlsbergensis) and *Bacillus lentus* can be aligned to provide the maximum amount of homology between amino acid sequences. A comparison of these sequences shows that there are a number of conserved residues contained in each sequence. The conserved residues as between BPN' and *B. lentus* are identified in FIG. 2 (SEQ ID NO: 31).

These conserved residues, thus, may be used to define the corresponding equivalent amino acid residues of *Bacillus amyloliquefaciens* subtilisin in other subtilisins such as subtilisin from *Bacillus lentus* (PCT Publication No. WO89/06279 published Jul. 13, 1989), the preferred protease precursor enzyme herein, or the subtilisin referred to as PB92 (EP 0 328 299), which is highly homologous to the preferred *Bacillus lentus* subtilisin. The amino acid sequences of certain of these subtilisins are aligned in FIGS. 3A and 3B with the sequence of *Bacillus amyloliquefaciens* subtilisin to produce the maximum homology of conserved residues. As can be seen, there are a number of deletions in the sequence of *Bacillus lentus* as compared to *Bacillus amyloliquefaciens* subtilisin. Thus, for example, the equivalent amino acid for Val165 in *Bacillus amyloliquefaciens* subtilisin in the other subtilisins is isoleucine for *B. lentus* and *B. licheniformis*.

Thus, for example, the amino acid at position +170 is lysine (K) in both *B. amyloliquefaciens* and *B. licheniformis* subtilisins and arginine (R) in Savinase. In one embodiment of the protease variants of the invention, however, the amino acid equivalent to +170 in *Bacillus amyloliquefaciens* subtilisin is substituted with aspartic acid (D). The abbreviations and one letter codes for all amino acids in the present invention conform to the Patentin User Manual (GenBank, Mountain View, Calif.) 1990, p. 101.

Homologous sequences can also be determined by using a "sequence comparison algorithm." Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

An example of an algorithm that is suitable for determining sequence similarity is the BLAST algorithm, which is described in Altschul, et al., *J. Mol. Biol.* 215:403–410 (1990). Software for performing BLAST analyses is publicly available through the National Center for Biotechnology Information (www.ncbi.nlm.ni.h.gov/). This algorithm involves first identifying high scoring sequence pairs (HSPs) by identifying short words of length W in the query sequence that either match or satisfy some positive-valued threshold score T when aligned with a word of the same length in a database sequence. These initial neighborhood word hits act as starting points to find longer HSPs containing them. The word hits are expanded in both directions along each of the two sequences being compared for as far as the cumulative alignment score can be increased. Extension of the word hits is stopped when: the cumulative alignment score falls off by the quantity X from a maximum achieved value; the cumulative score goes to zero or below; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, *Proc. Natl. Acad. Sci. USA* 89:10915 (1989)) alignments (B) of 50, expectation (2) of 10, M'5, N'-4, and a comparison of both strands.

The BLAST algorithm then performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, an amino acid sequence is considered similar to a protein such as a protease if the smallest sum probability in a comparison of the test amino acid sequence to a protein such as a protease amino acid sequence is less than about 0.1, more preferably less than about 0.01, and most preferably less than about 0.001.

"Equivalent residues" may also be defined by determining homology at the level of tertiary structure for a precursor protein whose tertiary structure has been determined by x-ray crystallography. Equivalent residues are defined as those for which the atomic coordinates of two or more of the main chain atoms of a particular amino acid residue of the precursor protein such as the protease and *Bacillus amyloliquefaciens* subtilisin (N on N, CA on CA, C on C and O on O) are within 0.13 nm and preferably 0.1 nm after alignment. Alignment is achieved after the best model has been oriented and positioned to give the maximum overlap of atomic coordinates of non-hydrogen protein atoms of the protein such as the protease in question to the *Bacillus amyloliquefaciens* subtilisin. The best model is the crystallographic model giving the lowest R factor for experimental diffraction data at the highest resolution available.

Equivalent residues which are functionally analogous to a specific residue of *Bacillus amyloliquefaciens* subtilisin are defined as those amino acids of the precursor protein such as a protease which may adopt a conformation such that they either alter, modify or contribute to protein structure, substrate binding or catalysis in a manner defined and attributed to a specific residue of the *Bacillus amyloliquefaciens* subtilisin. Further, they are those residues of the precursor protein, for example, protease (for which a tertiary structure has been obtained by x-ray crystallography) which occupy an analogous position to the extent that, although the main chain atoms of the given residue may not satisfy the criteria of equivalence on the basis of occupying a homologous position, the atomic coordinates of at least two of the side chain atoms of the residue lie with 0.13 nm of the corresponding side chain atoms of *Bacillus amyloliquefaciens* subtilisin. The coordinates of the three dimensional structure of *Bacillus amyloliquefaciens* subtilisin are set forth in EPO Publication No. 0 251 446 (equivalent to U.S. Pat. No. 5,182,204, the disclosure of which is incorporated herein by reference) and can be used as outlined above to determine equivalent residues on the level of tertiary structure.

"Derivative" means a protein which is derived from a precursor protein (e.g., the native protein) by addition of one or more amino acids to either or both the C- and N-terminal end, substitution of one or more amino acids at one or a number of different sites in the amino acid sequence, deletion of one or more amino acids at either or both ends of the protein or at one or more sites in the amino acid sequence, or insertion of one or more amino acids at one or more sites in the amino acid sequence. The preparation of a protease derivative is preferably achieved by modifying a DNA sequence which encodes for the native protein, transformation of that DNA sequence into a suitable host, and expression of the modified DNA sequence to form the derivative protease.

The derivative of the invention includes peptides comprising altered amino acid sequences in comparison with a precursor amino acid sequence (e.g., a wild type or native state protease), which peptides retain a characteristic protease nature of the precursor protease but which have altered properties in some specific aspect. For example, a protease derivative may have an increased pH optimum or increased temperature or oxidative stability but will retain its characteristic substrate activity. Similarly, derivatives according to the present invention include a calcium binding domain which has either been added, removed or modified in such a way so as to significantly impair or enhance its calcium binding ability. Similarly, a catalytic proteolytic domain may either be added, removed or modified to operate in conjunction with the protease. It is contemplated that derivatives according to the present invention may be derived from a DNA fragment encoding a protease derivative wherein the functional activity of the expressed protease derivative is retained. Suitable methods for such modification of the precursor DNA sequence include methods disclosed herein, as well as methods known to those skilled in the art (see, for example, EP 0 328299, WO89/06279 and the U.S. patents and applications referenced herein). Some of the residues identified for substitution, insertion or deletion are conserved residues whereas others are not.

Such modification is preferably of the "precursor DNA sequence" which encodes the amino acid sequence of the precursor enzyme, but can be by the manipulation of the precursor protein. Examples of a precursor DNA sequence include, but are not limited to BPN' and BPN'-Y217L. In the case of residues which are not conserved, the replacement of one or more amino acids is limited to substitutions which produce a variant which has an amino acid sequence that does not correspond to one found in nature. In the case of conserved residues, such replacements should not result in a naturally-occurring sequence. Derivative further includes chemical modification to change the characteristics of the protease.

The phrase "substantially identical" in the context of two nucleic acids or polypeptides thus typically means that a polynucleotide or polypeptide comprises a sequence that has at least 60% sequence identity, preferably at least 80%, more preferably at least 90%, still more preferably 95% and sometimes as much as 97%, compared to a reference sequence using the programs described above (e.g., BLAST, ALIGN, CLUSTAL) using standard parameters. One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution.

Another indication that two nucleic acid sequences are substantially identical is that the two molecules hybridize to each other under stringent conditions (e.g., within a range of medium to high stringency).

"Hybridization" includes any process by which a strand of a nucleic acid joins with a complementary nucleic acid strand through base-pairing. Thus, strictly speaking, the term refers to the ability of the complement of the target sequence to bind to a test sequence, or vice-versa.

"Hybridization conditions" are typically classified by degree of "stringency" of the conditions under which hybridization is measured. The degree of stringency can be based, for example, on the melting temperature (Tm) of the nucleic acid binding complex or probe. For example, "maximum stringency" typically occurs at about Tm-5° C. (5° below the Tm of the probe); "high stringency" at about 5–10° below the Tm; "intermediate stringency" at about 10–20° below the Tm of the probe; and "low stringency" at about 20–25° below the Tm. Alternatively, or in addition, hybridization conditions can be based upon the salt or ionic strength conditions of hybridization and/or one or more stringency washes. For example, 6×SSC=very low stringency; 3×SSC=low to medium stringency; 1×SSC=medium stringency; and 0.5×SSC=high stringency. Functionally, maximum stringency conditions may be used to identify nucleic acid sequences having strict identity or near-strict identity with the hybridization probe; while high stringency conditions are used to identify nucleic acid sequences having about 80% or more sequence identity with the probe.

The variant protease having an altered epitope can be used to obtain oligonucleotide sequences or primers of about 10–30 nucleotides in length can be designed from the polynucleotide sequence, for example those disclosed in FIG. 6, and used in PCR technology to isolate the naturally occurring sequence or variants from genomic sequences.

Another general strategy for the "cloning" of B. subtilis genomic DNA pieces for sequencing uses inverse PCR. A known region is scanned for a set of appropriate restriction enzyme cleavage sites and inverse PCR is performed with a set of DNA primers determined from the outermost DNA sequence. The DNA fragments from the inverse PCR are directly used as template in the sequencing reaction. The newly derived sequences can be used to design new oligonucleotides. These new oligonucleotides are used to amplify DNA fragments with genomic DNA as template. The sequence determination on both strands of a DNA region is finished by applying a primer walking strategy on the genomic PCR fragments. The benefit of multiple starting points in the primer walking results from the series of inverse PCR fragments with different sizes of new "cloned" DNA pieces. From the most external DNA sequence, a new round of inverse PCR is started. The whole inverse PCR strategy is based on the sequential use of conventional taq polymerase and the use of long range inverse PCR in those cases in which the taq polymerase failed to amplify DNA fragments. Nucleic acid sequencing is performed using standard technology. One method for nucleic acid sequencing involves the use of a Perkin-Elmer Applied Biosystems 373 DNA sequencer (Perkin-Elmer, Foster City, Calif.) according to manufacturer's instructions.

Nucleic acid sequences derived from genomic DNA may contain regulatory regions in addition to coding regions. Whatever the source, the isolated MP gene should be molecularly cloned into a suitable vector for propagation of the gene.

In molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the altered epitopic sequence may be accomplished in a number of ways. For example, a oligomer of the altered epitope of a *B.subtilis* gene of the present invention or its specific RNA, or a fragment thereof, such as a probe or primer, may be isolated and labeled and then used in hybridization assays to detect an epitopic sequence with an altered immunogenic response. (Benton, W. and Davis, R., 1977, *Science* 196:180; Grunstein, M. and Hogness, D., 1975, *Proc. Natl. Acad. Sci. USA* 72:3961). Those DNA fragments sharing substantial sequence similarity to the probe will hybridize under stringent conditions.

Accordingly, the present invention provides a method for the detection of altered immunogenic polynucleotide homologues which comprises hybridizing part or all of a nucleic acid sequence of *B. subtilis* epitope of either genomic or cDNA origin.

The process of amplification as carried out in polymerase chain reaction (PCR) technologies is described in Dieffenbach, C W and G S Dveksler, (*PCR Primer, a Laboratory Manual,* Cold Spring Harbor Press, Plainview, N.Y., 1995). A nucleic acid sequence of at least about 10 nucleotides and as many as about 60 nucleotides from *B. subtilis* MP, preferably about 12 to 30 nucleotides, and more preferably about 20–25 nucleotides can be used as a probe or PCR primer.

For applications requiring high selectivity, one will typically desire to employ relatively stringent conditions to form the hybrids, e.g., one will select relatively low salt and/or high temperature conditions. Hybridization conditions, including moderate stringency and high stringency, are provided in Sambrook et al., incorporated herein by reference.

The present invention encompasses proteases having altered immunogenicity that are equivalent to those that are derived from the particular microbial strain mentioned. Being "equivalent," in this context, means that the proteases are encoded by a polynucleotide capable of hybridizing to the polynucleotide having the sequence as shown in any one of FIGS. 1A–1C (SEQ ID NO: 1) under conditions of medium to high stringency and still retaining the altered immunogenic response to human T-cells. Being equivalent means that the protease comprises at least 55%, at least 65%, at least 70%, at least 75%, at least 80%, at least 85%, at least 90%, at least 95%, at least 97% or at least 99% identity to the epitope sequences and the variant proteases having such epitopes, e.g, having the amino acid sequence disclosed in FIG. 4*a* (SEQ ID NO: 3) modified as described elsewhere in this application.

"Hybrid proteases" or "fusion protease", are proteins engineered from at least two different or "parental" proteins, which are preferably homologs of one another. For example, a preferred hybrid protease or fusion protein might have the N-terminus of a protein and the C-terminus of a homolog of the protein. In a preferred embodiment, the two terminal ends can be combined to correspond to the full-length active protein. In a preferred embodiment, the homologs share substantial similarity but do not have identical T-cell epitopes. Therefore, in one embodiment, for example, a protease of interest having one or more T-cell epitopes in the C-terminus may have the C-terminus replaced with the C-terminus of a homolog having a less potent T-cell epitope in the C-terminus, less T-cell epitopes, or no T-cell epitope in the C-terminus. Thus, the skilled artisan understands that by being able to identify T-cell epitopes among homologs, a variety of variants producing different immunogenic responses can be formed. Moreover, it is understood that internal portions, and more than one homolog can be used to produce the variants of the present invention.

A hybrid example contemplated by the inventors included a protease hybrid constructed using established protein engineering techniques. The hybrid was constructed so that a highly allergenic amino acid sequence of the protein was replaced with a corresponding sequence from a less allergenic homolog. In this instance, the first 122 amino acids of the protease were derived from GG36, and the remaining amino acid sequence was derived from BPN'.

The variants of the present invention include the mature forms of protein variants, as well as the pro- and preproforms of such protein variants. The prepro-forms are the preferred construction since this facilitates the expression, secretion and maturation of the protein variants.

"Prosequence" refers to a sequence of amino acids bound to the N-terminal portion of the mature form of a protein which when removed results in the appearance of the "mature" form of the protein. Many proteolytic enzymes are found in nature as translational proenzyme products and, in the absence of post-translational processing, are expressed in this fashion. A preferred prosequence for producing protein variants such as protease variants is the putative prosequence of *Bacillus amyloliquefaciens* subtilisin, although other prosequences may be used.

A "signal sequence" or "presequence" refers to any sequence of amino acids bound to the N-terminal portion of a protein or to the N-terminal portion of a proprotein which may participate in the secretion of the mature or pro forms of the protein. This definition of signal sequence is a functional one, meant to include all those amino acid sequences encoded by the N-terminal portion of the protein gene which participate in the effectuation of the secretion of protein under native conditions. The present invention utilizes such sequences to effect the secretion of the protein variants as defined herein. One possible signal sequence comprises the first seven amino acid residues of the signal sequence from *Bacillus subtilis* subtilisin fused to the remainder of the signal sequence of the subtilisin from *Bacillus lentus* (ATCC 21536).

A "prepro" form of a protein variant consists of the mature form of the protein having a prosequence operably linked to the amino terminus of the protein and a "pre" or "signal" sequence operably linked to the amino terminus of the prosequence.

"Expression vector" refers to a DNA construct containing a DNA sequence which is operably linked to a suitable control sequence capable of effecting the expression of said DNA in a suitable host. Such control sequences include a promoter to effect transcription, an optional operator sequence to control such transcription, a sequence encoding suitable mRNA ribosome binding sites and sequences which control termination of transcription and translation. The vector may be a plasmid, a phage particle, or simply a potential genomic insert. Once transformed into a suitable host, the vector may replicate and function independently of the host genome, or may, in some instances, integrate into the host genome itself. In the present specification, "plasmid" and "vector" are sometimes used interchangeably as the plasmid is the most commonly used form of vector at present. However, the invention is intended to include such other forms of expression vectors which serve equivalent functions and which are, or become, known in the art.

The "host cells" used in the present invention generally are procaryotic or eucaryotic hosts which preferably have been manipulated by the methods disclosed in U.S. Pat. No. 4,760,025 (RE 34,606) to render them incapable of secreting enzymatically active endoprotease. A preferred host cell for expressing protein is the *Bacillus* strain BG2036 which is deficient in enzymatically active neutral protein and alkaline protease (subtilisin). The construction of strain BG2036 is described in detail in U.S. Pat. No. 5,264,366. Other host cells for expressing protein include *Bacillus subtilis* I168 (also described in U.S. Pat. No. 4,760,025 (RE 34,606) and U.S. Pat. No. 5,264,366, the disclosure of which are incorporated herein by reference), as well as any suitable *Bacillus* strain such as *B. licheniformis, B. lentus,* etc.

Host cells are transformed or transfected with vectors constructed using recombinant DNA techniques. These techniques can be found in any molecular biology practice guide, for example, Sambrook et al. Molecular Cloning—A Laboratory Manual (2nd ed.) Vol. 1–3, Cold Springs Harbor Publishing (1989) ("Sambrook"); and Current Protocols in Molecular Biology, Ausubel et al.(eds.), Current Protocols, a joint venture between Greene Publishing Associates, Inc. and John Wiley & Sons, Inc., (1997 Supplement) ("Ausubel"). Such transformed host cells are capable of either replicating vectors encoding the protein variants or expressing the desired protein variant. In the case of vectors which encode the pre- or prepro-form of the protein variant, such variants, when expressed, are typically secreted from the host cell into the host cell medium.

"Operably linked", when describing the relationship between two DNA regions, simply means that they are functionally related to each other. For example, a presequence is operably linked to a peptide if it functions as a signal sequence, participating in the secretion of the mature form of the protein most probably involving cleavage of the signal sequence. A promoter is operably linked to a coding sequence if it controls the transcription of the sequence; a ribosome binding site is operably linked to a coding sequence if it is positioned so as to permit translation.

The genes encoding the naturally-occurring precursor protein may be obtained in accord with the general methods known to those skilled in the art. The methods generally comprise synthesizing labeled probes having putative sequences encoding regions of the protein of interest, preparing genomic libraries from organisms expressing the protein, and screening the libraries for the gene of interest by hybridization to the probes. Positively hybridizing clones are then mapped and sequenced.

The protein gene is ligated into an appropriate expression plasmid. The cloned protein gene is then used to transform or transfect a host cell in order to express the protein gene. This plasmid may replicate in hosts in the sense that it contains the well-known elements necessary for plasmid replication or the plasmid may be designed to integrate into the host chromosome. The necessary elements will be provided for efficient gene expression, e.g., a promoter operably linked to the gene in question (which may be supplied as the gene's own homologous promoter if it is recognized, i.e., transcribed, by the host), a transcription terminator (a polyadenylation region for eucaryotic host cells) which is exogenous or is supplied by the endogenous terminator region of the protein gene and, desirably, a selection gene such as an antibiotic resistance gene that enables continuous cultural maintenance of plasmid-infected host cells by growth in antibiotic-containing media.

In one embodiment, the gene can be a natural gene such as that from *B lentus* or *B. amyloliquefaciens*. Alternatively, a synthetic gene encoding a naturally-occurring or mutant precursor protein may be produced. In such an approach, the DNA and/or amino acid sequence of the precursor protein is determined. Multiple, overlapping synthetic single-stranded DNA fragments are thereafter synthesized, which upon hybridization and ligation produce a synthetic DNA encoding the precursor protein. An example of synthetic gene construction is set forth in Example 3 of U.S. Pat. No. 5,204,015, the disclosure of which is incorporated herein by reference.

Once the naturally-occurring or synthetic precursor protein gene has been cloned, a number of modifications are undertaken to enhance the use of the gene beyond synthesis of the naturally-occurring precursor protein. Such modifications include the production of recombinant proteins as disclosed in U.S. Pat. No. 4,760,025 (RE 34,606) and EPO Publication No. 0 251 446 and the production of protein variants described herein.

Protein variants can be made by a wide variety of different mutagenesis techniques well known to those skilled in the art. These techniques can be found in any molecular biology laboratory manual, for example, Sambrook et al., Molecuar Cloning—A Laboratory Manual ($2^{nd}$ ed.), Cold Spring Harbor, or Current Protocols in Molecular Biology, Ausubel et al. Green Publishing Associates Inc. and John Wiley & Sons. Mutagenesis kits are also available from many commercial molecular biology suppliers. Methods are available to make specific substitutions at defined amino acids (site-directed), specific or random mutations in a localized region of the gene (regio-specific) or random mutqagenesis over the entire gene (saturation mutagensis). Site-directed mutagenesis of single-stranded DNA or double-stranded DNA using PCR, cassette mutagenesis, gene synthesis, error-prone PCR, and chemical saturation mutagenesis are all techniques that one can use to generate the desired protein variants. After the variants are produced, they can be screened for the desired property (altered, e.g., high or increased; or low or reduced immunogenic response, increased thermal or alkaline stability, etc.).

In one aspect of the invention, the objective is to secure a variant protein having altered immunogenic response potential as compared to the precursor protein. While the instant invention is useful to lower the immunogenic response, the mutations specified herein may be utilized in combination with mutations known in the art to result altered thermal stability and/or altered substrate specificity, modified activity, improved specific activity or altered alkaline stability as compared to the precursor.

Accordingly, the present invention is directed to altering the capability of the T-cell epitope which includes residue positions 109–123 in *B. amyloliquefaciens* to induce T-cell proliferation. In addition, the present invention is directed to altering the capability of the T-cell epitope which includes residue positions 70–84 in *B. amyloliquefaciens* to induce T-cell proliferation. One preferred embodiment of the invention comprises making modification at one or both of positions 79 and 122. Another embodiment of the invention comprises making modifications at one or both of position 76 and 122. Still another embodiment comprises modifications at positions 76, 79 and 122. In combination with the presently disclosed mutation(s) in the region corresponding to amino acid residues 109–123 and/or 70–84, the present invention further contemplates a mutation (e.g., a substitution) at position 76, optionally in combination with one or more substitutions selected from the group consisting of positions corresponding to 3, 31, 40, 41, 111, 147, 218, 206, and/or 217.

Embodiments of the present invention contemplate specific combinations of substituted residues corresponding to positions: 79–122–217, 76–122–217, and 76–79–122–217, optionally in combination with one or more substitutions in the protease of interest equivalent to those selected from the group consisting of positions corresponding to: 3, 76, 31, 40, 41, 111, 147, 218, 206, and/or 217 of Bacillus amyloliquefaciens subtilisin. Other embodiments include a further additional substitutions at one or more positions in said protease of interest equivalent to those selected from the group consisting of 216, 181, 101, 215, 216, 217, 247, 46, 154, 128, 182, 101, 104, 107, 250, 254, 258, 50, 47, 48, 182, 183, 185, 248, and 262 of Bacillus amyloliquefaciens. Such mutations may be used, in addition to decreasing the allergenic potential of the variant protein of the invention, to modulate overall stability and/or proteolytic activity of the enzyme.

More particularly, the specific substitutions include N76D, I79T, I79A, I122A and conservative substitutions thereof. Other embodiments of the present invention contemplate specific combinations of substituted residues corresponding to positions: I79A-I122A-Y217L, N76D-I122A-Y217L, and N76D-I79A-I122A-Y217L, optionally along with one or more of the following substitutions: S3T; N76D; I31L; P40Q; D41A; I111V; V147P,I; N218S; Q206L; and/or L217M. Optionally, further substitution at one or more positions corresponding to the group of positions consisting of A216K, D181G, S101V, G215A, A216E, Y217S, R247Y, R247S, R247Q, G46S, S101Q, S154G, G128S, S182T, S101R, Y104W, I107V, L250G, T254G, T254A, G258S, M50A, G47S, A48G, S182R, S183R, Q185A, S101R, S248G, and Y262F.

Combination sets contemplated by the inventors include, but are not limited to BPN'-Y217L/I79A; BPN'-Y217LN/I79A/I122A; BPN'-Y217L/N76D/I122A; BPN'-Y217L/N76D/I79A/I122A; and BPN'-Y217L/N76D. Additional combinations sets contemplated by the inventors include, but are not limited to N76D/I79A/I122A/N218S; N76D/I79A/I122A/Q206L; N76D/I79A/I122A/Q206L/N218S; I79A/I122A/Q206L; I79A/I122A/N218S; I79A/I122A/P40Q; I79A/I122A/D41A; and I79A/I122A/H238Y. In one embodiment these last combination sets were made in a BPN'-Y217L protease of interest. In another embodiment, additional combinations sets of P1-N76D/I79A/I122A/A216K; P1-N76D/I79A/I122A/D181G; P1-N76D/I79A/I122A/S101V; P1-N76D/I79A/I122A/G215A; P1-N76D/I79A/I122A/A216E; P1-N76D/I79A/I122A/L217S; P1-N76D/I79A/I122AR247Y; P1-N76D/I79A/I122A/R247S; P1-N76D/I79A/I122A/R247Q; P1-N76D/I79A/I122A/G46S; P1-N76D/I79A/I122A/S101Q/S154G; P1-N76D/I79A/I122A/G128S; P1-N76D/I79A/I122A/S182T; P1-N76D/I79A/I122A/S101R; P1-N76D/I79A/I122A/Y104W/I107V; P1-N76D/I79A/I122A/L250G; P1-N76D/I79A/I122A/T254G; P1-N76D/I79A/I122A/T254A; P1-N76D/I79A/I122A/G258S; P1-N76D/I79A/I122A/M50A; P1-N76D/I79A/I122A/G47S; P1-N76D/I79A/I122A/A48G; P1-N76D/I79A/I122A/S182R; P1-N76D/I79A/I122A/S183R; P1-N76D/I79A/I122A/Q185A; P1-N76D/I79A/I122A/S101R/I107V; P1-N76D/I79A/I122A/S248G; and P1-N76D/I79A/I122A/Y262F were constructed, P1 being BPN'-Y217L.

The most preferred embodiments of the invention include the following specific combinations of substituted residues corresponding to positions N76D-I122A-Y217L of Bacillus amyloliquefaciens subtilisin. These substitutions are preferably made in Bacillus amyloliquefaciens (recombinant or native-type) subtilisin, although the substitutions may be made in any Bacillus protein.

Based on the screening results obtained with the variant proteins, the mutations noted above in Bacillus amyloliquefaciens subtilisin are important to the proteolytic activity, performance and/or stability of these enzymes and the cleaning or wash performance as well as other applications of such variant enzymes.

In addition to the point mutations described above, fusing two homologous proteins can also eliminate T-cell epitopes. As is exemplified below, a region of a protein in which a T-cell epitope resides may be replaced with the same region in a homologous protein that doesn't have the T-cell epitope. In the exemplification below, a fusion protein is created with protease from Bacillus lentus and its B. amyloliquefaciens homolog so that the resulting protein does not have the T-cell epitope present in the parental B. lentus protease. Any length can be fused into the parental protein, from only the epitope to the majority of the protein, as long as the desired activity is maintained. However, it is not necessary that the original level of activity be maintained. Because of the lowered allergenicity of the protein, it may be possible to use more of the hybrid protein than of the parental protein to achieve the same activity levels.

The variant protease activity can be determined and compared with the protease of interest by examining the interaction of the protease with various commercial substrates, including, but not limited to casein, keratin, elastin, collagen. Protease activity can be determined by those analysis known in the art. Exemplary assays to determine protease activity include, but are not limited to, succinyl-Ala-Ala-Pro-Phe-para nitroanilide (SAAPFpNA) (citation) assay (SEQ ID NO: 6); and 2,4,6-trinitrobenzene sulfonate sodium salt (TNBS) assay. In the SAAPFpNA assay, proteases cleave the bond between the peptide and p-nitroaniline to give a visible yellow colour absorbing at 405 nm. In the TNBS color reaction method, the assay measures the enzymatic hydrolysis of the substrate into polypeptides containing free amino groups. These amino groups react with TNBS to form a yellow colored complex. Thus the more deeply colored the reaction, the more activity is measured. The yellow color can be determined by various analyzers or spectrophotometers known in the art.

Other characterisitics of the variant proteases can be determined by methods known to those skilled in the art. Exemplary characteristics include, but are not limited to thermal stability, alkaline stability, and stability of the particular protease in various substrate or buffer solutions or product formulations.

When combined with the enzyme stability assay procedure disclosed herein, mutants obtained by random mutagenesis were identified which demonstrated either increased or decreased alkaline or thermal stability while maintaining enzymatic activity.

Alkaline stability is measured either by known procedures or by the methods described herein. A substantial change in alkaline stability is evidenced by at least about a 5% or greater increase or decrease (preferably increase) in the half life of the enzymatic activity of a mutant when compared to the precursor carbonyl hydrolase. In the case of subtilisins, alkaline stability can be measured as a function of enzymatic activity of subtilisin at varying pH.

Thermal stability is measured either by known procedures or by the methods described herein. A substantial change in thermal stability is evidenced by at least about a 5% or greater increase or decrease (preferably increase) in the half-life of the catalytic activity of a mutant when exposed to a relatively high temperature and neutral pH as compared to the precursor carbonyl hydrolase. In the case of subtilisins, thermal stability is measured by the autoproteolytic degradation of subtilisin at elevated temperatures and various pH's. See FIGS. 14 and 15.

Many of the protein variants of the invention are useful in formulating various detergent compositions. A number of known compounds are suitable surfactants useful in compositions comprising the protein mutants of the invention. These include nonionic, anionic, cationic, anionic or zwitterionic detergents, as disclosed in U.S. Pat. No. 4,404,128 to Barry J. Anderson and U.S. Pat. No. 4,261,868 to Jiri Flora, et al. A suitable detergent formulation is that described in Example 7 of U.S. Pat. No. 5,204,015 (previously incorporated by reference). The art is familiar with the different formulations which can be used as cleaning compositions. In addition to typical cleaning compositions, it is readily understood that the protein variants of the present invention may be used for any purpose that native or wild-type proteins are used. Thus, these variants can be used, for example, in bar or liquid soap applications, dishcare formulations, surface cleaning applications, contact lens cleaning solutions or products, peptide hydrolysis, waste treatment, textile applications, as fusion-cleavage enzymes in protein production, etc. The variants of the present invention may comprise, in addition to decreased allergenicity, enhanced performance in a detergent composition (as compared to the precursor). As used herein, enhanced performance in a detergent is defined as increasing cleaning of certain enzyme sensitive stains such as grass or blood, as determined by usual evaluation after a standard wash cycle.

Proteins, particularly proteases of the invention can be formulated into known powdered and liquid detergents having pH between 6.5 and 12.0 at levels of about 0.01 to about 5% (preferably 0.1% to 0.5%) by weight. These detergent cleaning compositions can also include other enzymes such as known proteases, amylases, cellulases, lipases or endoglycosidases, as well as builders and stabilizers.

The addition of proteins, particularly proteases of the invention to conventional cleaning compositions does not create any special use limitation. In other words, any temperature and pH suitable for the detergent is also suitable for the present compositions as long as the pH is within the above range, and the temperature is below the described protein's denaturing temperature. In addition, proteins of the invention can be used in a cleaning composition without detergents, again either alone or in combination with builders and stabilizers.

One aspect of the invention is a composition for the treatment of a textile that includes variant proteins of the present invention. The composition can be used to treat for example silk or wool as described in publications such as RD 216,034; EP 134,267; U.S. Pat. No. 4,533,359; and EP 344,259.

The variants can be screened for proteolytic activity according to methods well known in the art. Preferred protease variants include multiple substitutions at positions corresponding to 76, 79, 122 of *Bacillus amyloliquefaciens* subtilisin.

The protease of this invention exhibit modified immunogenicity when compared to their precursor proteins. In preferred embodiments, the proteins exhibit reduced allergenicity. One of skill will readily recognize that the uses of the proteases of this invention will be determined, in large part, on the immunological properties of the proteins. For example, proteases that exhibit reduced allergenicity can be used in cleaning compositions. "Cleaning compositions" are compositions that can be used to remove undesired compounds from substrates, such as fabric, dishes, contact lenses, other solid substrates, hair (shampoos), skin (soaps and creams), teeth (mouthwashes, toothpastes) etc. An effective amount of one or more protease variants described herein may be included in compositions useful for cleaning a variety of surfaces in need of proteinaceous stain removal. Such cleaning compositions include detergent compositions for cleaning hard surfaces, unlimited in form (e.g., liquid and granular); detergent compositions for cleaning fabrics, unlimited in form (e.g., granular, liquid and bar formulations); dishwashing compositions (unlimited in form); oral cleaning compositions, unlimited in form (e.g., dentifrice, toothpaste and mouthwash formulations); and denture cleaning compositions, unlimited in form (e.g., liquid, tablet). As used herein, "effective amount" refers to the quantity of protease variants necessary to achieve the enzymatic activity necessary in the specific cleaning composition. Such effective amounts are readily ascertained by one of ordinary skill in the art and is based on many factors, such as the particular enzyme variant used, the cleaning application, the specific composition of the cleaning composition, and whether a liquid or dry (e.g., granular, bar) composition is required, and the like.

An effective amount of one or more protease variants described herein may also be included in compositions to be applied to keratinous materials such as nails and hair, including but not limited to those useful as hair spray compositions, hair shampooing and/or conditioning compositions, compositions applied for the purpose of hair growth regulation, and compositions applied to the hair and scalp for the purpose of treating seborrhea, dermatitis, and/or dandruff.

An effective amount of one or more protease variant described herein may be in included in compositions suitable for topical application to the skin or hair. These compositions can be in the form of creams, lotions, gels, and the like, and may be formulated as aqueous compositions or may be formulated as emulsions of one or more oil phases in an aqueous continuous phase.

For example, the skin care compositions may include a variant of a protease of interest as described above comprising a T-cell epitope, wherein said variant differs from said protease of interest by having an altered T-cell epitope such that said variant and said protease of interest produce different immunogenic responses in a human. The variant of the protease of interest may include an amino acid substitution selected from the group consisting of residues corresponding to 76, 79 and 122 of *Bacillus amyloliquefaciens* subtilisin; humectants; skin care actives; surfactants; emollients; polymeric thickening agents and silicone.

Skin Care Active

The compositions herein may comprise a skin care active at a level from about 0.1% to about 20%, preferably from about 1% to about 10%, more preferably from about 2% to about 8%, by weight. Non-limiting examples of suitable skin care actives for use herein include a vitamin $B_3$ component, panthenol, vitamin E, vitamin E acetate, retinol, retinyl propionate, retinyl palmitate, retinoic acid, vitamin C, theobromine, α-hydroxyacid, farnesol, phytantriol, salicylic acid, palmityl peptapeptide-3 and mixtures thereof.

B3 Compound

As used herein, "vitamin $B_3$ compound" means a compound having the formula:

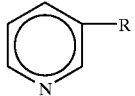

wherein R is —$CONH_2$ (i.e., niacinamide), —COOH (i.e., nicotinic acid) or —$CH_2OH$ (i.e., nicotinyl alcohol); derivatives thereof; and salts of any of the foregoing. Exemplary derivatives of the foregoing vitamin $B_3$ compounds include nicotinic acid esters, including non-vasodilating esters of nicotinic acid, nicotinyl amino acids, nicotinyl alcohol esters of carboxylic acids, nicotinic acid N-oxide and niacinamide N-oxide.

Suitable esters of nicotinic acid include nicotinic acid esters of $C_1$–$C_{22}$, preferably $C_1$–$C_{16}$, more preferably $C_1$–$C_6$ alcohols. The alcohols are suitably straight-chain or branched chain, cyclic or acyclic, saturated or unsaturated (including aromatic), and substituted or unsubstituted. The esters are preferably non-vasodilating. As used herein, "non-vasodilating" means that the ester does not commonly yield a visible flushing response after application to the skin in the subject compositions (the majority of the general population would not experience a visible flushing response, although such compounds may cause vasodilation not visible to the naked eye). Non-vasodilating esters of nicotinic acid include tocopherol nicotinate and inositol hexanicotinate; tocopherol nicotinate is preferred. A more complete description of vitamin $B_3$ compounds is given in WO 98/22085. Preferred vitamin $B_3$ compounds are niacinamide and tocopherol nicotinate.

Retinoids

Another suitable skin care active is a retinoid. As used herein, "retinoid" includes all natural and/or synthetic analogs of Vitamin A or retinol-like compounds which possess the biological activity of Vitamin A in the skin as well as the geometric isomers and stereoisomers of these compounds. When a retinoid is included in the compositions herein, it will typically comprise from or about 0.005% to or about 2%, more preferably 0.01% to about 2% retinoid. Retinol is preferably used in an amount of from or about 0.01% to or about 0.15%; retinol esters are preferably used in an amount of from about 0.01% to about 2% (e.g., about 1%).

The retinoid is preferably retinol, retinol esters (e.g., $C_2$–$C_{22}$ alkyl esters of retinol, including retinyl palmitate, retinyl acetate, retinyl proprionate), retinal, and/or retinoic acid (including all-trans retinoic acid and/or 13-cis-retinoic acid), more preferably retinoids other than retinoic acid. These compounds are well known in the art and are commercially available from a number of sources, e.g., Sigma Chemical Company (St. Louis, Mo.), and Boehringer Mannheim (Indianapolis, Ind.). Preferred retinoids are retinol, retinyl palmitate, retinyl acetate, retinyl proprionate, retinal, retinoic acid and combinations thereof. More preferred are retinol, retinoic propionate, retinoic acid and retinyl palmitate. The retinoid may be included as the substantially pure material, or as an extract obtained by suitable physical and/or chemical isolation from natural (e.g., plant) sources.

Carrier

The compositions herein can comprise a safe and effective amount of a dermatologically acceptable carrier, suitable for topical application to the skin or hair within which the essential materials and optional other materials are incorporated to enable the essential materials and optional components to be delivered to the skin or hair at an appropriate concentration. The carrier can thus act as a diluent, dispersant, solvent, or the like for the essential components which ensures that they can be applied to and distributed evenly over the selected target at an appropriate concentration.

The type of carrier utilized in the present invention depends on the type of product form desired for the composition. The carrier can be solid, semi-solid or liquid. Suitable carriers are liquid or semi-solid, such as creams, lotions, gels, sticks, ointments, pastes and mousses. Preferably the carrier is in the form of a lotion, cream or a gel, more preferably one which has a sufficient thickness or yield point to prevent the particles from sedimenting. The carrier can itself be inert or it can possess dermatological benefits of its own. The carrier may be applied directly to the skin and/or hair, or it may be applied via a woven or non-woven wipe or cloth. It may also be in the form of a patch, mask, or wrap. It may also be aerosolized or otherwise sprayed onto the skin and/or hair. The carrier should also be physically and chemically compatible with the essential components described herein, and should not unduly impair stability, efficacy or other use benefits associated with the compositions of the present invention.

Preferred carriers contain a dermatologically acceptable, hydrophilic diluent. Suitable hydrophilic diluents include water, organic hydrophilic diluents such as $C_1$–$C_4$ monohydric alcohols and low molecular weight glycols and polyols, including propylene glycol, polyethylene glycol (e.g. of MW 200–600), polypropylene glycol (e.g. of MW 425–2025), glycerol, butylene glycol, 1,2,4-butanetriol, sorbitol esters, 1,2,6-hexametriol, ethanol, iso-propanol, sorbitol esters, ethoxylated ethers, propoxylated ethers and combinations thereof. The diluent is preferably liquid. Water is a preferred diluent. The composition preferably comprises at least about 20% of the hydrophilic diluent.

Suitable carriers may also comprise an emulsion comprising a hydrophilic phase, especially an aqueous phase, and a hydrophobic phase e.g., a lipid, oil or oily material. As well known to one skilled in the art, the hydrophilic phase will be dispersed in the hydrophobic phase, or vice versa, to form respectively hydrophilic or hydrophobic dispersed and continuous phases, depending on the composition ingredients. In emulsion technology, the term "dispersed phase" is a term well-known to one skilled in the art which means that the phase exists as small particles or droplets that are suspended in and surrounded by a continuous phase. The dispersed phase is also known as the internal or discontinuous phase. The emulsion may be or comprise (e.g., in a triple or other multi-phase emulsion) an oil-in-water emulsion or a water-in-oil emulsion such as a water-in-silicone emulsion. Oil-in-water emulsions typically comprise from about 1% to about 60% (preferably about 1% to about 30%) of the dispersed hydrophobic phase and from about 1% to about 99% (preferably from about 40% to about 90%) of the continuous hydrophilic phase; water-in-oil emulsions typically comprise from about 1% to about 98% (preferably from about 40% to about 90%) of the dispersed hydrophilic phase and from about 1% to about 50% (preferably about 1% to about 30%) of the continuous hydrophobic phase.

Humectants

The compositions of the present invention may comprise humectants which are preferably present at a level of from about 0.01% to about 20%, more preferably from about 0.1% to about 15% and especially from about 0.5% to about 10%. Preferred humectants include, but are not limited to, compounds selected from polyhydric alcohols, urea, D or DL panthenol, calcium pantothenate, royal jelly, panthetine, pantotheine, panthenyl ethyl ether, pangamic acid, pyridoxin, pantoyl lactose Vitamin B complex, hexane-1,2, 6,-triol, guanidine or its derivatives, and mixtures thereof.

Suitable polyhydric alcohols for use herein include polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, erythritol, threitol, pentaerythritol, xylitol, glucitol, mannitol, hexylene glycol, butylene glycol (e.g., 1,3-butylene glycol), hexane triol (e.g., 1,2,6-hexanetriol), trimethylol propane, neopentyl glycol, glycerine, ethoxylated glycerine, propane-1,3 diol, propoxylated glycerine and mixtures thereof. The alkoxylated derivatives of any of the above polyhydric alcohols are also suitable for use herein. Preferred polyhydric alcohols of the present invention are selected from glycerine, butylene glycol, propylene glycol, dipropylene glycol, polyethylene glycol, hexane triol, ethoxylated glycerine and propoxylated glycerine, and mixtures thereof.

Suitable humectants useful herein are sodium 2-pyrrolidone-5-carboxylate (NaPCA), guanidine; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); hyaluronic acid and derivatives thereof (e.g., salt derivatives such as sodium hyaluronate); lactamide monoethanolamine; acetamide monoethanolamine; urea; panthenol and derivatives thereof; and mixtures thereof.

At least part (up to about 5% by weight of composition) of a humectant can be incorporated in the form of an admixture with a particulate cross-linked hydrophobic acrylate or methacrylate copolymer, itself preferably present in an amount of from about 0.1% to about 10%, which can be added either to the aqueous or disperse phase. This copolymer is particularly valuable for reducing shine and controlling oil while helping to provide effective moisturization benefits and is described in further detail by WO96/03964, incorporated herein by reference.

Emollients

The oil in water emulsion embodiments of the present invention may comprise from about 1% to about 20%, preferably from about 1.5% to about 15%, more preferably from about 0.1% to about 8%, more preferably from about 0.5% to about 5% of a dermatologically acceptable emollient. Emollients tend to lubricate the skin, increase the smoothness and suppleness of the skin, prevent or relieve dryness of the skin, and/or protect the skin. Emollients are typically water-immiscible, oily or waxy materials and emollients with high molecular weights can confer tacky properties to a topical composition. A wide variety of suitable emollients are known and may be used herein. Sagarin, *Cosmetics, Science and Technology*, 2nd Edition, Vol. 1, pp. 32–43 (1972), contains numerous examples of materials suitable as an emollient. All emollients discussed in application WO 00/24372 should be considered as suitable for use in the present invention although preferred examples are outlined in further detail below:

i) Straight and branched chain hydrocarbons having from about 7 to about 40 carbon atoms, such as dodecane, squalane, cholesterol, hydrogenated polyisobutylene, isohexadecane, isoeicosane, isooctahexacontane, isohexapentacontahectane, and the $C_7$–$C_{40}$ isoparaffins, which are $C_7$–$C_{40}$ branched hydrocarbons. Suitable branched chain hydrocarbons for use herein are selected from isopentacontaoctactane, petrolatum, and mixtures thereof. Suitable for use herein are branched chain aliphatic hydrocarbons sold under the trade name Permethyl (RTM) and commercially available from Presperse Inc., P.O. Box 735, South Plainfield, N.J. 07080, U.S.A.

ii) $C_1$–$C_{30}$ alcohol esters of $C_1$–$C_{30}$ carboxylic acids, C12–15 alkyl benzoates, and of $C_2$–$C_{30}$ dicarboxylic acids, e.g. isononyl isononanoate, isostearyl neopentanoate, isodecyl octanoate, isodecyl isononanoate, tridecyl isononanoate, myristyl octanoate, octyl pelargonate, octyl isononanoate, myristyl myristate, myristyl neopentanoate, myristyl octanoate, isopropyl myristate, myristyl propionate, isopropyl stearate, isopropyl isostearate, methyl isostearate, behenyl behenate, dioctyl maleate, diisopropyl adipate, and diisopropyl dilinoleate and mixtures thereof.

iii) $C_1$–$C_{30}$ mono- and poly- esters of sugars and related materials. These esters are derived from a sugar or polyol moiety and one or more carboxylic acid moieties. Depending on the constituent acid and sugar, these esters can be in either liquid or solid form at room temperature. Examples include: glucose tetraoleate, the galactose tetraesters of oleic acid, the sorbitol tetraoleate, sucrose tetraoleate, sucrose pentaoleate, sucrose hexaoleate, sucrose heptaoleate, sucrose octaoleate, sorbitol hexaester in which the carboxylic acid ester moieties are palmitoleate and arachidate in a 1:2 molar ratio, and the octaester of sucrose wherein the esterifying carboxylic acid moieties are laurate, linoleate and behenate in a 1:3:4 molar ratio. Other materials include cottonseed oil or soybean oil fatty acid esters of sucrose. Other examples of such materials are described in WO 96/16636, incorporated by reference herein. A particularly preferred material is known by the INCI name sucrose polycottonseedate iv) Vegetable oils and hydrogenated vegetable oils. Examples of vegetable oils and hydrogenated vegetable oils include safflower oil, coconut oil, cottonseed oil, menhaden oil, palm kernel oil, palm oil, peanut oil, soybean oil, rapeseed oil, linseed oil, rice bran oil, pine oil, sesame oil, sunflower seed oil, partially and fully hydrogenated oils from the foregoing sources, and mixtures thereof v) Soluble or colloidally-soluble moisturizing agents. Examples include hylaronic acid and starch-grafted sodium polyacrylates such as Sanwet (RTM) IM-1000, IM-1500 and IM-2500 available from Celanese Superabsorbent Materials, Portsmith, Va., USA and described in U.S. Pat. No. 4,076,663.

Preferred emollients for use herein are isohexadecane, isooctacontane, petrolatum, isononyl isononanoate, isodecyl octanoate, isodecyl isononanoate, tridecyl isononanoate, myristyl octanoate, octyl isononanoate, myristyl myristate, methyl isostearate, isopropyl isostearate, C12–15 alkyl benzoates and mixtures thereof. Particularly preferred emollients for use herein are isohexadecane, isononyl isononanoate, methyl isostearate, isopropyl isostearate, petrolatum, or mixtures thereof.

Emulsifiers/Surfactants

Compositions herein may contain an emulsifier and/or surfactant, generally to help disperse and suspend the disperse phase within the continuous aqueous phase. A surfactant may also be useful if the product is intended for skin cleansing. For convenience hereinafter emulsifiers will be referred to under the term 'surfactants', thus 'surfactant(s)' will be used to refer to surface active agents whether used as emulsifiers or for other surfactant purposes such as skin cleansing. Known or conventional surfactants can be used in the composition, provided that the selected agent is chemically and physically compatible with essential components of the composition, and provides the desired characteristics. Suitable surfactants include non-silicone derived materials, and mixtures thereof. All surfactants discussed in application WO 00/24372 should be considered as suitable for use in the present invention.

The compositions of the present invention may comprise from about 0.05% to about 15% of a surfactant or mixture of surfactants. The exact surfactant or surfactant mixture chosen will depend upon the pH of the composition and the other components present.

Among the nonionic surfactants that are useful herein are those that can be broadly defined as condensation products of long chain alcohols, e.g. $C_{8-30}$ alcohols, with sugar or starch polymers ie glycosides. Other useful nonionic surfactants include the condensation products of alkylene oxides with fatty acids (i.e. alkylene oxide esters of fatty acids). These materials have the general formula $RCO(X)_n$ OH wherein R is a $C_{10-30}$ alkyl group, X is —$OCH_2CH_2$— (i.e. derived from ethylene glycol or oxide) or —$OCH_2CHCH_3$— (i.e. derived from propylene glycol or oxide), and n is an integer from about 6 to about 200. Other nonionic surfactants are the condensation products of alkylene oxides with 2 moles of fatty acids (i.e. alkylene oxide diesters of fatty acids). These materials have the general formula $RCO(X)_nOOCR$ wherein R is a $C_{10-30}$ alkyl group, X is —$OCH_2CH_2$— (i.e. derived from ethylene glycol or oxide) or —$OCH_2CHCH_3$— (i.e. derived from propylene glycol or oxide), and n is an integer from about 6 to about 100. An emulsifier for use herein is most preferably a fatty acid ester blend based on a mixture of sorbitan fatty acid ester and sucrose fatty acid ester, especially a blend of sorbiton stearate and sucrose cocoate. This is commercially available from ICI under the trade name Arlatone 2121. Even further suitable examples include a mixture of cetearyl alcohols, cetearyl glucosides such as those available under the trade name Montanov 68 from Seppic and Emulgade PL68/50 available from Henkel.

The hydrophilic surfactants useful herein can alternatively or additionally include any of a wide variety of cationic, anionic, zwitterionic, and amphoteric surfactants such as are known in the art. See, e.g., McCutcheon's, *Detergents and Emulsifiers,* North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973. A wide variety of anionic surfactants are also useful herein. See, e.g., U.S. Pat. No. 3,929,678, to Laughlin et al., issued Dec. 30, 1975.

A variety of anionic surfactants are also useful herein. See, e.g., U.S. Pat. No. 3,929,678, to Laughlin et al., issued Dec. 30, 1975. Exemplary anionic surfactants include the alkoyl isethionates (e.g., $C_{12}$–$C_{30}$), alkyl and alkyl ether sulfates and salts thereof, alkyl and alkyl ether phosphates and salts thereof, alkyl methyl taurates (e.g., $C_{12}$–$C_{30}$), and soaps (e.g., alkali metal salts, e.g., sodium or potassium salts) of fatty acids.

Amphoteric and zwitterionic surfactants are also useful herein. Examples of amphoteric and zwitterionic surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 22 carbon atoms (preferably $C_8$–$C_{18}$) and one contains an anionic water solubilising group, e.g., carboxy, sulfonate, sulfate, phosphate, or phosphonate. Examples are alkyl imino acetates, and iminodialkanoates and aminoalkanoates, imidazolinium and ammonium derivatives. Other suitable amphoteric and zwitterionic surfactants are those selected from the group consisting of betaines, sultaines, hydroxysultaines, and branched and unbranched alkanoyl sarcosinates, and mixtures thereof.

Some emulsions of the present invention may include a silicone containing emulsifier or surfactant. A wide variety of silicone emulsifiers are useful herein. These silicone emulsifiers are typically organically modified organopolysiloxanes, also known to those skilled in the art as silicone surfactants. Useful silicone emulsifiers include dimethicone copolyols. These materials are polydimethyl siloxanes which have been modified to include polyether side chains such as polyethylene oxide chains, polypropylene oxide chains, mixtures of these chains, and polyether chains containing moieties derived from both ethylene oxide and propylene oxide. Other examples include alkyl-modified dimethicone copolyols, i.e., compounds which contain $C_2$–$C_{30}$ pendant side chains. Still other useful dimethicone copolyols include materials having various cationic, anionic, amphoteric, and zwitterionic pendant moieties.

Polymeric Thickening Agents

The compositions of the present invention can comprise at least one polymeric thickening agent. The polymeric thickening agents useful herein preferably have a number average molecular weight of greater than 20,000, more preferably greater than 50,000 and especially greater than 100,000. The compositions of the present invention may comprise from about 0.01% to about 10%, preferably from about 0.1% to about 8% and most preferably from about 0.5% to about 5% by weight of the composition of the polymeric thickening agent, or mixtures thereof.

Preferred polymer thickening agents for use herein include non-ionic thickening agents and anionic thickening agents, or mixtures thereof. Suitable non-ionic thickening agents include polyacrylamide polymers, crosslinked poly (N-vinylpyrrolidones), polysaccharides, natural or synthetic gums, polyvinylpyrrolidone, and polyvinylalcohol. Suitable anionic thickening agents include acrylic acid/ethyl acrylate copolymers, carboxyvinyl polymers and crosslinked copolymers of alkyl vinyl ethers and maleic anhydride. Particularly preferred thickening agents for use herein are the non-ionic polyacrylamide polymers such as polyacrylamide and isoparaffin and laureth-7, available under the trade name Sepigel 305 from Seppic Corporation, and acrylic acid/ethyl acrylate copolymers and the carboxyvinyl polymers sold by the B.F. Goodrich Company under the trade mark of Carbopol resins, or mixtures thereof. Suitable Carbopol resins may be hydrophobically modified, and other suitable resins are described in WO98/22085, or mixtures thereof.

Silicone Oil

The present compositions may comprise, at least one silicone oil phase. Silicone oil phase(s) generally comprises from about 0.1% to about 20%, preferably from about 0.5% to about 10%, more preferably from about 0.5% to about 5%, of the composition. The, or each, silicone oil phase preferably comprises one or more silicone components.

Silicone components can be fluids, including straight chain, branched and cyclic silicones. Suitable silicone fluids useful herein include silicones inclusive of polyalkyl siloxane fluids, polyaryl siloxane fluids, cyclic and linear polyalkylsiloxanes, polyalkoxylated silicones, amino and quaternary ammonium modified silicones, polyalkylaryl siloxanes or a polyether siloxane copolymer and mixtures thereof. The silicone fluids can be volatile or non-volatile. Silicone fluids generally have a weight average molecular weight of less than about 200,000. Suitable silicone fluids have a molecular weight of about 100,000 or less, preferably about 50,000 or less, most preferably about 10,000 or less. Preferably the silicone fluid is selected from silicone fluids having a weight average molecular weight in the range from about 100 to about 50,000 and preferably from about 200 to about 40,000. Typically, silicone fluids have a viscosity ranging from about 0.65 to about 600,000 $mm^2.s^{-1}$, preferably from about 0.65 to about 10,000 $mm^2.s^{-1}$ at 25° C. The viscosity can be measured by means of a glass capillary viscometer as set forth in Dow Corning Corporate Test Method CTM0004, Jul. 29, 1970. Suitable polydimethyl siloxanes that can be used herein include those available, for example, from the General Electric Company as the SF and Viscasil (RTM) series and from Dow Corning as the Dow Corning 200 series. Also useful are essentially non-volatile polyalkylarylsiloxanes, for example, polymethylphenylsiloxanes, having viscosities of about 0.65 to 30,000 $mm^2.s^{-1}$ at 25° C. These siloxanes are available, for example, from the General Electric Company as SF 1075 methyl phenyl fluid or from Dow Corning as 556 Cosmetic Grade Fluid. Cyclic polydimethylsiloxanes suitable for use herein are those having a ring structure incorporating from about 3 to about 7 $(CH_3)_2SiO$ moieties.

Silicone gums can also be used herein. The term "silicone gum" herein means high molecular weight silicones having a weight average molecular weight in excess of about 200,000 and preferably from about 200,000 to about 4,000,000. Iincluded are non-volatile polyalkyl and polyaryl siloxane gums. In preferred embodiments, a silicone oil phase comprises a silicone gum or a mixture of silicones including the silicone gum. Typically, silicone gums have a viscosity at 25° C. in excess of about 1,000,000 $mm^2s^{-1}$. The silicone gums include dimethicones as described by Petrarch and others including U.S. Pat. No. 4,152,416, May 1, 1979 to Spitzer, et al, and Noll, Walter, *Chemistry and Technology of Silicones*, New York: Academic Press 1968. Also describing silicone gums are General Electric Silicone Rubber Product Data Sheets SE 30, SE 33, SE 54 and SE 76. Specific examples of silicone gums include polydimethylsiloxane, (polydimethylsiloxane)(methylvinylsiloxane) copolymer, poly(dimethylsiloxane)(diphenyl)(methylvinylsiloxane) copolymer and mixtures thereof. Preferred silicone gums for use herein are silicone gums having a molecular weight of from about 200,000 to about 4,000,000 selected from dimethiconol, dimethicone copolyol, dimethicone, and mixtures thereof.

A silicone phase herein preferably comprises a silicone gum incorporated into the composition as part of a silicone gum-fluid blend. When the silicone gum is incorporated as part of a silicone gum-fluid blend, the silicone gum preferably constitutes from about 5% to about 40%, especially from about 10% to 20% by weight of the silicone gum-fluid blend. Suitable silicone gum-fluid blends herein are mixtures consisting essentially of:
(i) a silicone having a molecular weight of from about 200,000 to about 4,000,000 selected from dimethiconol, fluorosilicone and dimethicone and mixtures thereof; and
(ii) a carrier which is a silicone fluid, the carrier having a viscosity from about 0.65 $mm^2.s^{-1}$ to about 100 $mm^2.s^{-1}$, wherein the ratio of i) to ii) is from about 10:90 to about 20:80 and wherein said silicone gum-based component has a final viscosity of from about 100 $mm^2.s^{-1}$ to about 100,000 $mm^2.s^{-1}$, preferably from 500 $mm^2.s^{-1}$ to about 10,000 $mm^2.s^{-1}$.

Further silicone components suitable for use in a silicone oil phase herein are crosslinked polyorganosiloxane polymers, optionally dispersed in a fluid carrier. In general, when present the crosslinked polyorganosiloxane polymers, together with its carrier (if present) comprises 0.1% to about 20%, preferably from about 0.5% to about 10%, more preferably from about 0.5% to about 5% of the composition. Such polymers comprise polyorganosiloxane polymers crosslinked by a crosslinking agent. Suitable crosslinking agents are disclosed in WO98/22085. Examples of suitable polyorganosiloxane polymers for use herein include methyl vinyl dimethicone, methyl vinyl diphenyl dimethicone and methyl vinyl phenyl methyl diphenyl dimethicone.

Another class of silicone components suitable for use in a silicone oil phase herein includes polydiorganosiloxane-polyoxyalkylene copolymers containing at least one polydiorganosiloxane segment and at least one polyoxyalkylene segment. Suitable polydiorganosiloxane segments and copolymers thereof are disclosed in WO98/22085. Suitable polydiorganosiloxane-polyalkylene copolymers are available commercially under the tradenames Belsil (RTM) from Wacker-Chemie GmbH, Geschäftsbereich S, Postfach D-8000 Munich 22 and Abil (RTM) from Th. Goldschmidt Ltd., Tego House, Victoria Road, Ruislip, Middlesex, HA4 0YL, for example Belsil (RTM) 6031 and Abil (RTM) B88183. A particularly preferred copolymer fluid blend for use herein includes Dow Corning DC3225C which has the CTFA designation Dimethicone/Dimethicone copolyol.

Sunscreens

Compositions of the present invention may comprise an organic sunscreen. Suitable sunscreens can have UVA absorbing properties, UVB absorbing properties or a mixture thereof. The exact amount of the sunscreen active will vary depending upon the desired Sun Protection Factor, ie the "SPF" of the composition as well as the desired level of UV protection. The compositions of the present invention preferably comprise an SPF of at least 10, preferably at least 15. SPF is a commonly used measure of photoprotection of a sunscreen against erythema. The SPF is defined as a ratio of the ultraviolet energy required to produce minimal erythema on protected skin to that required to products the same minimal erythema on unprotected skin in the same individual. See Federal Register, 43, No 166, pp. 38206–38269, Aug. 25, 1978). Amounts of the sunscreen used are typically from about 2% to about 20%, more typically from about 4% to about 14%. Suitable sunscreens include, but are not limited to, those found in the *CTFA International Cosmetic Ingredient Dictionary and Handbook*, 7th edition, volume 2 pp. 1672, edited by Wenninger and McEwen (*The Cosmetic, Toiletry, and Fragrance Association, Inc., Washington, D.C.*, 1997).

The compositions of the present invention may comprise a UVA absorbing sunscreen actives which absorb UV radiation having a wavelength of from about 320 nm to about 400 nm. Suitable UVA absorbing sunscreen actives are selected from dibenzoylmethane derivatives, anthranilate derivatives such as methylanthranilate and homomethyl, 1-N-acetylanthranilate, and mixtures thereof. Examples of dibenzoylmethane sunscreen actives are described in U.S. Pat. No 4,387,089 issued to Depolo; and in Sunscreens: Development, Evaluation, and Regulatory Aspects edited by N. J. Lowe and N. A. Shaath, Marcel Dekker, Inc (1990).

The UVA absorbing sunscreen active is preferably present in an amount to provide broad spectrum UVA protection either independently, or in combination with, other UV protective actives which may be present in the composition.

Suitable UVA sunscreen actives are dibenzoylmethane sunscreen actives and their derivatives. They include, but are not limited to, those selected from 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropylbenzoylmethane, 4-(1,1-dimethylethyl)-4'-methoxydibenzoylmethane, 2-methyl-5-isopropyl-4'-methoxydibenzoylmethane, 2-methyl-5-tert-butyl-4'-methoxy-dibenzoylmethane, 2,4-dimethyl-4'-methoxydibenzoylmethane, 2,6-dimethyl-4'-tert-butyl-4'methoxydibenzoylmethane, and mixtures thereof. Preferred dibenzoyl sunscreen actives include those selected from 4-(1,1-dimethylethyl)-4'-methoxydibenzoylmethane, 4-isopropyldibenzoylmethane, and mixtures thereof. A preferred sunscreen active is 4-(1,1-dimethylethyl)-4'-methoxydibenzoylmethane.

The sunscreen active 4-(1,1-dimethylethyl)-4'-methoxydibenzoylmethane, which is also known as butyl methoxydibenzoylmethane or Avobenzone, is commercially available under the names of Parsol® 1789 from Givaudan Roure (International) S. A. (Basel, Switzerland) and Eusolex® 9020 from Merck & Co., Inc (Whitehouse Station, N.J.). The sunscreen 4-isoproplydibenzoylmethane, which is also known as isopropyldibenzoylmethane, is commercially available from Merck under the name of Eusolex® 8020.

The compositions of the present invention may further comprise a UVB sunscreen active which absorbs UV radiation having a wavelength of from about 290 nm to abut 320 nm. The compositions comprise an amount of the UVB sunscreen active which is safe and effective to provide UVB protection either independently, or in combination with, other UV protective actives which may be present in the compositions. The compositions may comprise from about 0.1% to abut 16%, more preferably from about 0.1% to about 12%, and most preferably from about 0.5% to about 8% by weight, of UVB absorbing organic sunscreen.

A variety of UVB sunscreen actives are suitable for use herein. Nonlimiting examples of such organic sunscreen actives are described in U.S. Pat. No. 5,087,372 issued Feb. 11, 1992 to Haffey et al.; and U.S. Pat. Nos. 5,073,371 and 5,073,372 both issued on Dec. 17, 1991 to Turner et al. and Segarin, et al., at Chapter VIII, pages 189 et seq., of *Cosmetics Science and Technology*. Still other useful sunscreens are those disclosed in U.S. Pat. No. 4,937,370, to Sabatelli, issued Jun. 26, 1990; and U.S. Pat. No. 4,999,186, to Sabatelli et al., issued Mar. 12, 1991. Preferred UVB sunscreen actives are selected from 2-ethylhexyl-2-cyano-3,2-ethylhexyl N,N-dimethyl-p-aminobenzoate, p-aminobenzoic acid, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene) camphor, 3-diphenylacrylate (referred to as octocrylene), 2-phenyl-benzimidazole-5-sulphonic acid (PBSA), cinnamates and their derivatives such as 2-ethylhexyl-p-methoxycinnamate and octyl-p-methoxycinnamate, TEA salicylate, octyldimethyl PABA, camphor derivatives and their derivatives, and mixtures thereof. Preferred organic sunscreen actives are 2-ethylhexyl-2-cyano-3,3-diphenylacrylate (referred to as octocrylene), 2-phenyl-benzimidazole-5-sulphonic acid (PBSA), octyl-p-methoxycinnamate, and mixtures thereof.

Salt and acid neutralized forms of the acidic sunscreens are also useful herein.

An agent may also be added to any of the compositions useful in the present invention to stabilize the UVA sunscreen to prevent it from photo-degrading on exposure to UV radiation and thereby maintaining its UVA protection efficacy. A wide range of compounds have been cited as providing these stabilizing properties and should be chosen to compliment both the UVA sunscreen and the composition as a whole. Suitable stabilizing agents include, but are not limited to, those described in U.S. Pat. Nos. 5,972,316; 5,968,485; 5,935,556; 5,827,508 and Patent WO 00/06110. Preferred examples of stabilizing agents for use in the present invention include 2-ethylhexyl-2-cyano-3,3-diphenylacrylate (referred to as octocrylene), ethyl-2-cyano-3,3-diphenylacrylate, 2-ethylhexyl-3,3-diphenylacrylate, ethyl-3,3-bis(4-methoxyphenyl)acrylate, and mixtures thereof. 2-ethylhexyl-2-cyano-3,3-diphenylacrylate is most preferred.

An agent may also be added to any of the compositions useful in the present invention to improve the skin substantivity of those compositions, particularly to enhance their resistance to being washed off by water, or rubbed off. A preferred agent which will provide this benefit is a copolymer of ethylene and acrylic acid. Compositions comprising this copolymer are disclosed in U.S. Pat. No. 4,663,157, Brock, issued May 5, 1987.

In addition to the organic sunscreens compositions of the present invention can additionally comprise inorganic physical sunblocks. Nonlimiting examples of suitable physical sunblocks are described in CTFA International Cosmetic Ingredient Dictionary, $6^{th}$ Edition, 1995, pp. 1026–28 and 1103, Sayre, R. M. et al., "Physical Sunscreens", J. Soc. Cosmet. Chem., vol 41, no 2, pp. 103–109 (1990). Preferred inorganic physical sunblocks are zinc oxide and titanium dioxide, and mixtures thereof.

When used, the physical sunblocks are present in an amount such that the present compositions are transparent on the skin (ie non-whitening), preferably less than or equal to about 5%. When titanium dioxide is used, it can have an anatase, rutile, or amorphous structure. Physical sunblock particles, e.g. titanium dioxide and zinc oxide, can be uncoated or coated with a variety of materials including but not limited to amino acids, aluminum compounds such as alumina, aluminium stearate, aluminium laurate, and the like; carboxylic acids and their salts e.g. stearic acid and its salts; phospholipids such as lecithin; organic silicone compounds; inorganic silicone compounds such as silica and silicates; and mixtures thereof. A preferred titanium dioxide is commercially available from Tayca (Japan) and is distributed by Tri-K Industries (Emerson, N.J.) under the MT micro-ionised series (e.g. MT 100SAS). The compositions of the present invention may comprise from about 0.1% to about 10%, more preferably from about 0.1% to about 4%, and most preferably from about 0.5% to about 2.5%, by weight, of inorganic sunscreen.

Anti-Microbial and Anti-Fungal Actives

The compositions herein may also comprise anti-microbial and anti-fungal actives. Non-limiting examples of anti-microbial and anti-fungal actives useful herein include β-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, octopirox, parachlorometa xylenol, nystatin, tolnaftate, clotrimazole, cetylpyridinium chloride (CPC), piroctone olamine, selenium sulfide, ketoconazole, triclocarbon, triclosan, zinc pyrithione, itraconazole, asiatic acid, hinokitiol, mipirocin and those described in EPA 0,680,745 (herein incorporated by reference), clinacycin hydrochloride, benzoyl peroxide, benzyl peroxide, minocyclin, phenoxy isopropanol, and mixtures thereof.

Other Optional Ingredients

A variety of optional ingredients such as neutralizing agents, perfumes, and colouring agents, can also be added to the compositions herein. It is preferred that any additional ingredients enhance the skin softness/smoothness benefits of the product. In addition it is preferred that any such ingredients do not negatively impact the aesthetic properties of the product. As such high levels of proteins such as collagen and elastin are not preferred in compositions useful in the present invention.

The compositions of the invention can also contain from about 0.01% to about 10%, preferably from about 0.1% to about 5% of a panthenol moisturizer. The panthenol moisturizer can be selected from D-panthenol ([R]-2,4-dihydroxy-N-[3-hydroxypropyl)]-3,3-dimethylbutamide), DL-panthenol, calcium pantothenate, royal jelly, panthetine, pantotheine, panthenyl ethyl ether, pangamic acid, pyridoxin, and pantoyl lactose.

Neutralizing agents suitable for use in neutralizing acidic group containing hydrophilic gelling agents herein include sodium hydroxide, potassium hydroxide, ammonium hydroxide, monoethanolamine, diethanolamine, amino methyl propanol, tris-buffer and triethanolamine.

Other optional materials include keratolytic agents; water-soluble or solubilizable preservatives preferably at a level of from about 0.1% to about 5%, such as Germall 115, methyl, ethyl, propyl and butyl esters of hydroxybenzoic acid, benzyl alcohol, DMDM hydantoin iodopropanyl butylcarbanate available under the trade name Glydant Plus from Lonza, EDTA, Euxyl (RTM) K400, Bromopol (2-bromo-2-nitropropane-1,3-diol) and phenoxypropanol; anti-bacterials such as Irgasan (RTM) and phenoxyethanol (preferably at levels of from 0.1% to about 5%); soluble or colloidally-soluble moisturising agents such as hylaronic acid and starch-grafted sodium polyacrylates such as Sanwet (RTM) IM-1000, IM-1500 and IM-2500 available from Celanese Superabsorbent Materials, Portsmith, Va., USA and described in U.S. Pat. No. 4,076,663; vitamins such as vitamin A, vitamin C, vitamin E and derivatives thereof and building blocks thereof such as phytantriol and vitamin K and components thereof such as the fatty alcohol dodecatrienol; alpha and beta hydroxyacids; aloe vera; sphingosines and phytosphingosines, cholesterol; skin whitening agents; N-acetyl cysteine; colouring agents; antibacterial agents such as TCC/TCS, also known as triclosan and trichlorocarbon; perfumes and perfume solubilizers. Examples of alpha hydroxy acids include glycolic acid, lactic acid, malic acid, citric acid, glycolic acid in conjunction with ammonium glycolate, alpha-hydroxy ethanoic acid, alpha-hydroxyoctanoic acid, alpha-hydroxycaprylic acid, hydroxycaprylic acid, mixed fruit acid, tri-alp0ha hydroxy fruit acids, triple fruit acid, sugar cane extract, alpha hydroxy and botanical comprise, I-alpha hydroxy acid and glycomer in crosslinked fatty acids alpha nutrium. Preferred examples of alpha hydroxy acids are glycolic acid and lactic acid. It is preferred that alpha hydroxy acids are used in levels of upto 10%.

A safe and effective amount of an anti-inflammatory agent may be added to the compositions of the subject invention, preferably from about 0.1% to about 5%, more preferably from about 0.1% to about 2%, of the composition. The anti-inflammatory agent enhances the skin appearance benefits of the present invention, e.g., such agents contribute to a more uniform and acceptable skin tone or colour. The exact amount of anti-inflammatory agent to be used in the compositions will depend on the particular anti-inflammatory agent utilized since such agents vary widely in potency.

Compositions of the subject invention can further include an anti-oxidant/radical scavenger. The anti-oxidant/radical scavenger is especially useful for providing protection against UV radiation which can cause increased scaling or texture changes in the stratum corneum and against other environmental agents which can cause skin damage. Suitable amounts are from about 0.1% to about 10%, more preferably from about 1% to about 5%, of the composition. Anti-oxidants/radical scavengers such as ascorbic acid (vitamin C) and its salts.

The inclusion of a chelating agent is especially useful for providing protection against UV radiation which can contribute to excessive scaling or skin texture changes and against other environmental agents which can cause skin damage. A suitable amount is from about 0.01% to about 1%, more preferably from about 0.05% to about 0.5%, of the composition. Exemplary chelators that are useful herein are disclosed in U.S. Pat. No. 5,487,884, incorporated herein by reference. Preferred chelators useful in compositions of the subject invention are ethylenediamine tetraacetic acid (EDTA), furildioxime, and derivatives thereof.

The compositions of the present invention can also comprise a skin lightening agent. When used, the compositions preferably comprise from about 0.1% to about 10%, more preferably from about 0.2% to about 5%, also preferably from about 0.5% to about 2%, of a skin lightening agent. Suitable skin lightening agents include those known in the art, including kojic acid, arbutin, ascorbic acid and derivatives thereof, e.g., magnesium ascorbyl phosphate. Further skin lightening agents suitable for use herein also include those described in WO 95/34280 and WO 95/23780; each incorporated herein by reference.

Other optional materials include water-soluble or solubilizable preservatives preferably at a level of from about 0.1% to about 5%, such as Germall 115, methyl, ethyl, propyl and butyl esters of hydroxybenzoic acid, benzyl alcohol, DMDM hydantoin iodopropanyl butylcarbanate available under the trade name Glydant Plus from Lonza, EDTA, Euxyl (RTM) K400, Bromopol (2-bromo-2-nitropropane-1,3-diol) and phenoxypropanol; anti-bacterials such as Irgasan (RTM) and phenoxyethanol (preferably at levels of from 0.1% to about 5%). Antibacterial agents such as TCC/TCS, also known as triclosan and trichlorocarbon are also useful in compositions of the present invention.

Other optional materials herein include pigments which, where water-insoluble, contribute to and are included in the total level of oil phase ingredients. Pigments suitable for use in the compositions of the present invention can be organic and/or inorganic. Also included within the term pigment are materials having a low colour or lustre such as matte finishing agents, and also light scattering agents. Preferably the compositions of the present invention comprise particulate materials having a refractive index of from about 1.3 to about 1.7, the particulate materials being dispersed in the composition and having a median particle size of from about 2 to about 30 $\mu$m. Preferably the particulates useful herein have relatively narrow distributions, by which is meant that more than 50% of the particles fall within 31 $\mu$m either side of the respective median value. Also preferred is that more than 50%, preferably more than 60%, more preferably more than 70% of particles fall within the size ranges prescribed for the respective median values. Suitable particulate materials are organic or organosilicone and preferably organosilicone polymers. Preferred particles are free-flowing, solid, materials. By "solid" is meant that the particles are not hollow. The void at the centre of hollow particles can have an adverse effect on refractive index and therefore the visual effects of the particles on either skin or the composition. Suitable organic particulate materials include those made of polymethylsilsesquioxane, referenced above, polyamide, polythene, polyacrylonitrile, polyacrylic acid, polymethacrylic acid, polystyrene, polytetrafluoroethylene (PTFE) and poly(vinylidene chloride). Copolymers derived from monomers of the aforementioned materials can also be used. Inorganic materials include silica and boron nitride. Representative commercially available examples of useful particulate materials herein are Tospearl® 145 which has a median particle size of about 4.5 $\mu$m and EA-209® from Kobo which is an ethylene/acrylic acid copolymer having a median particle size of about 10 $\mu$m, Nylon-12 available under the trade name Orgasol 2002 from Elf Atochem, France, or mixtures thereof.

Further examples of suitable pigments are titanium dioxide, predispersed titanium dioxide from Kobo e.g. Kobo GWL75CAP, iron oxides, acyglutamate iron oxides, ultramarine blue, D&C dyes, carmine, and mixtures thereof. Depending upon the type of composition, a mixture of pigments will normally be used. The preferred pigments for use herein from the viewpoint of moisturisation, skin feel, skin appearance and emulsion compatibility are treated pigments. The pigments can be treated with compounds such as amino acids, silicones, lecithin and ester oils.

Suitably, the pH of the compositions herein is in the range from about 6.1 to about 10.0, wherein the pH of the final composition is adjusted by addition of acidic, basic or buffer salts as necessary.

Preparation of Compositions

The compositions of the present invention are prepared by standard techniques well known to those skilled in the art. In general the aqueous phase and/or the oil phase would be prepared separately, with materials of similar phase partitioning being added in any order. If the final product is an emulsion, the two phases will then be combined with vigorous stirring. Any ingredients in the formulation with high volatility, or which are susceptible to hydrolysis at high temperatures, can be added with gentle stirring towards the end of the process, post emulsification if applicable.

Proteases with reduced allergenicity can also be used in the treatment of textiles. "Textile treatment" comprises a process wherein textiles, individual yarns or fibers that can be woven, felted or knitted into textiles or garments are treated to effect a desired characteristic. Examples of such desired characteristics are "stone-washing", depilling, dehairing, desizing, softening, and other textile treatments well known to those of skill in the art.

In one embodiment of the present invention, the epitopes identified herein can be used to elicit an immune response, e.g., where it is desired to raise antibodies against a protease including one or both of such epitopes. Such antibodies can be used, for example, to screen for other proteases that include one or both of these regions, or regions highly homologous thereto. Accordingly, the present invention provides a protease including one or both of the following sequences: (i) residues 70–84 and/or (ii) residues 109–123 of *Bacillus amyloliquefaciens* subtilisin. The present invention can be embodied in immunoassays utilizing isolated natural epitope, recombinant protein, or synthetic peptide representing specific epitopic regions to evaluate persons for sensitization to proteins including these or highly homologous regions.

In another embodiment, the epitopic fragments herein can be used in the detection of antigen presenting cells having MHC molecules capable of binding and displaying such fragments. For example, the epitopic fragments can include a detectable label (e.g., radiolabel). The labeled fragments can then be incubated with cells of interest, and then cells which bind (or display) the labeled fragments can be detected.

It should be appreciated that the present invention extends to all proteins against which it is desired to modulate the immunogenic response, for example, peptides to be used as T-cell vaccines, or peptides or proteins to be used as therapeutic agents against, e.g., cancer, infectious diseases and autoimmune diseases.

Vaccines and or therapeutic agents can be used in conjunction with pharmaceutically acceptable carriers. As used herein, a "pharmaceutically acceptable" component is one that is suitable for use with humans and/or animals without undue adverse side effects (such as toxicity, irritation, and allergic response) commensurate with a reasonable benefit/risk ratio. As used herein, a "pharmaceutical carrier" is a pharmaceutically acceptable solvent, suspending agent or vehicle for delivering the protease having reduced allergenicity to the animal or human. The carrier may be liquid or solid and is selected with the planned manner of administration in mind. Exemplary liquid carriers include sterile saline, water, buffers, organic solvents and combinations thereof.

The doseage amount will vary widely depending on the species of the warm blooded animal or human, and virus being treated. The dosage administered will, of course, vary depending upon known factors, such as the pharmacodynamic characteristics of the particular agent and its mode and route of administration; the age, health and/or weight of the recipient; the nature and extent of the symptoms; the metabolic characteristics of the drug and patient, the kind of concurrent treatment; the frequency of treatment; or the effect desired.

Generally a dosage of as little as about 1 milligrams (mg) per kilogram (kg) of body mass is suitable, but preferably as little as 10 mg/kg and up to about 10,000 mg/kg can be used. Preferably from 10 mg/kg to about 5000 mg/kg is used. Most preferably the doses are between 250 mg/kg to about 5000 mg/kg. Doses useful in the topical reduction of an immunogenic response are 250 mg/kg, 500 mg/kg, 2500 mg/kg, 3500 mg/kg, 4000 mg/kg, 5000 mg/kg and 6000 mg/kg. Any range of doses can be used. Generally the altered immunogenic protease can be administered on a daily basis one or more times a day, or reduced immunogenic proteases can be given one to four times a week either in a single dose or separate doses during the day. Twice weekly dosing over a period of at least several weeks is preferred, and often dosing will be continued over extended periods of time and maybe for the lifetime of the patient. However, the dosage and the dosage regimen will vary depending on the ability of the patient to sustain the desired and effective plasma levels of the anti-viral agents in the blood.

Intravenously, the most preferred doses may range from about 1 to about 10 mg/kg/minute during a constant rate infusion.

The dosage for humans is generally less than that used in mice and is typically about $1/12$ of the dose that is effective in mice. Thus, if 500 mg/kg was effective in mice, a dose of 42 mg/kg would be used in humans. For a 60 kg man, this dose would be 2520 mg.

The compounds of the present invention can be administered by any suitable means including, but not limited to, for example, oral, rectal, nasal, topical (including transdermal, aerosol, buccal and sublingual), vaginal, parenteral (including subcutaneous, intramuscular, intravenous and intradermal), intravesical or injection into or around the virus.

The dosage amounts are based on the effective inhibitory concentrations observed in anti-viral studies. The preferred route will vary with the (1) condition and age of the recipient, (2) virus being treated (3) nature of the infection and (4) desired blood levels. It is believed that parenteral treatment by intravenous, subcutaneous, or intramuscular application of the compounds of the present invention formulated with an appropriate carrier, other antiviral agents or compounds or diluents to facilitate application will be the preferred method of administering the compounds to warm blooded animals.

All publications and patents referenced herein are hereby incorporated by reference in their entirety. The following is presented by way of example and is not to be construed as a limitation to the scope of the claims.

EXAMPLES

Example 1

Skin Care Products

"Minors" is inclusive of: pH modifiers, preservatives, viscosity modifiers, and perfumes. Amounts represent approximate weight percent, unless otherwise indicated, and are not intended to indicate significant digits.

| MOISTURISING BODYWASH RAW MATERIAL | pH = 7 Amount |
| --- | --- |
| Deionised Water | QS |
| Glycerin | 4.0 |
| PEG-6 Caprylic/Capric Glycerides | 4.0 |
| Palm Kernal Fatty acids | 3.0 |
| Sodium Laureth-3 Sulphate | 45.0 |
| Cocamide MEA | 3.0 |
| Sodium Lauroamphoacetate | 25.0 |
| Soyabean Oil | 10.0 |
| Polyquaternium-10 (JR30M) | 0.70 |
| Protease | 1000 ppm |

| BODYWASH RAW MATERIAL | pH 6.5 Amount | pH 7 Amount | pH 8.5 Amount |
| --- | --- | --- | --- |
| Deionised water | QS | QS | QS |
| Sodium Laureth Sulphate | 12 | 15 | 8 |
| Cocamidopropyl Betaine | 8 | 10 | 15 |
| APG Glucoside (Plantacare 2000 1) | 0 | 2 | 1 |
| Polyquaternium-10 (JR30M) | 0.25 | 0 | 0 |
| Polyquaternium-7 (Mackam 55) | 0 | 0 | 0.7 |
| Protease | 250 ppm | 500 ppm | 1000 ppm |

1 - Cognis

| BODY LOTION RAW MATERIAL | pH 7 Amount | pH 7 Amount | pH 7.5 Amount | pH 7 Amount |
| --- | --- | --- | --- | --- |
| DEIONISED WATER | QS | QS | QS | QS |
| GLYCERINE | 8 | 8 | 10 | 12 |
| ISOHEXADECANE | 3 | 3 | 3 | 6 |
| NIACINAMIDE | 0 | 3 | 5 | 6 |
| ISOPROPYL ISOSTEARATE | 3 | 3 | 3 | 3 |
| Polyacrylamide, Isoparaffin, Laureth-7 (Sepigel 305[2]) | 3 | 3 | 3 | 3 |
| PETROLATUM | 4 | 4 | 4 | 2 |
| NYLON 12 | 2 | 2 | 2.5 | 2.5 |
| DIMETHICONE (DC1403[4]) | 2 | 2 | 2.5 | 2.5 |
| SUCROSE POLYCOTTONSEED OIL | 1.5 | 1.5 | 1.5 | 1.5 |
| Stearyl Alcohol 97% | 1 | 1 | 1 | 1 |
| D PANTHENOL | 1 | 1 | 1 | 1 |
| DL-alphaTOCOPHEROL ACETATE | 1 | 1 | 1 | 1 |
| Cetyl Alcohol 95% | 0.5 | 0.5 | 0.5 | 1 |
| BEHYNYL ALCOHOL | 1 | 1 | 1 | 0.5 |
| EMULGADE PL 68/50 | 0.4 | 0.4 | 0.5 | 0.5 |
| STEARIC ACID | 0.15 | 0.15 | 0.15 | 0.15 |
| Peg-100-stearate (MYRJ 59[1]) | 0.15 | 0.15 | 0.15 | 0.15 |
| Protease | 50 ppm | 50 ppm | 250 ppm | 1000 ppm |

[1]Uniqema
[2]Seppic
[4]Dow Corning

| ULTRA-HIGH MOISTURISING FACIAL CREAM/LOTION RAW MATERIAL | pH 7 Amount | pH 7 Amount |
| --- | --- | --- |
| Deionised water | QS | QS |
| Glycerin | 12 | 5 |
| PEG 400[6] | 0 | 10 |
| Niacinamide | 5 | 7 |
| Isohexadecane | 5 | 5 |
| Dimethicone (DC1403[3]) | 3 | 2 |
| Polyacrylamide, Isoparaffin, Laureth-7 (Sepigel 305[1]) | 3 | 3 |
| Isopropyl Isostearate | 2 | 2 |
| Polymethylsilsesquioxane | 2 | 2 |
| Cetyl Alcohol 95% | 1 | 1 |
| Sucrose polycottonseed oil | 1 | 1 |
| D-Panthenol | 1 | 1 |
| Vitamin E (Tocopherol Acetate) | 1 | 1 |
| Stearyl Alcohol 95% | 0.5 | 0.5 |
| Cetearyl Glucoside | 0.5 | 0.5 |
| Titanium dioxide | 0.3 | 0.3 |
| Stearic Acid | 0.15 | 0.15 |
| PEG-100-Stearate (Myrj 59[4]) | 0.15 | 0.15 |
| Protease | 500 ppm | 500 ppm |

[1]Seppic
[3]Dow Corning
[4]Uniqema
[5]Scher Chemicals
[6]Dow Chemicals

| FACIAL MOISTURISING CREAM RAW MATERIAL | pH 7 Amount | pH 7 Amount | pH 7.5 Amount |
| --- | --- | --- | --- |
| Deionised water | QS | QS | QS |
| Glycerin | 3 | 5 | 10 |
| Petrolatum | 3 | 3 | 0 |
| Cetyl Alcohol 95% | 1.5 | 1.5 | 1 |
| Dimethicone Copolyol (DC 3225C[4]) | 2 | 2 | 2 |
| Isopropyl Palmitate | 1 | 1 | 0.5 |
| Carbomer 954 [2] | 0.7 | 0.7 | 0.7 |
| Dimethicone (DC 200/350cs[4]) | 1 | 1 | 1 |
| Stearyl Alcohol 97% | 0.5 | 0.5 | 1 |
| Stearic acid | 0.1 | 0.1 | 0.1 |
| Peg-100-stearate (MYRJ 59[1]) | 0.1 | 0.1 | 0.1 |
| Titanium Dioxide | 0.3 | 0.3 | 0.3 |
| Protease | 50 ppm | 250 ppm | 1000 ppm |

[1]Uniqema
[2]BF Goodrich
[4]Dow Corning

Example 2

Assay for the Identification of Peptide T-Cell Epitopes Using Naïve Human T-Cells Fresh human peripheral blood cells were collected from "naïve" humans, i.e., persons not known to be exposed to or sensitized to *Bacillus lentus* protease, for determination of antigenic epitopes in protease from *Bacillus lentus* and human subtilisin. Naïve humans is intended to mean that the individual is not known to have been exposed to or developed a reaction to protease in the past. Peripheral mononuclear blood cells (stored at room temperature, no older than 24 hours) were prepared for use as follows: Approximately 30 mls of a solution of buffy coat preparation from one unit of whole blood was brought to 50 ml with Dulbecco's phosphate buffered solution (DPBS) and split into two tubes. The samples were underlaid with 12.5 ml of room temperature lymphoprep density separation media (Nycomed density 1.077 g/ml). The tubes were centrifuged for thirty minutes at 600G. The interface of the two phases was collected, pooled and washed in DPBS. The cell density of the resultant solution was measured by hemocytometer. Viability was measured by trypan blue exclusion.

From the resulting solution, a differentiated dendritic cell culture was prepared from the peripheral blood mononuclear cell sample having a density of $10^8$ cells per 75 ml culture flask in a solution as follows:

(1) 50 ml of serum free AIM V media (Gibco) was supplemented with a 1:100 dilution beta-mercaptoethanol (Gibco). The flasks were laid flat for two hours at 37° C. in 5% $CO_2$ to allow adherence of monocytes to the flask wall.

(2) Differentiation of the monocyte cells to dendritic cells was as follows: nonadherent cells were removed and the resultant adherent cells (monocytes) combined with 30 ml of AIM V, 800 units/ml of GM-CSF (Endogen) and 500 units/ml of IL-4 (Endogen); the resulting mixture was cultured for 5 days under conditions at 37° C. in 5% $CO_2$. After five days, the cytokine TNFα (Endogen) was added to 0.2 units/ml, and the cytokine IL-1α (Endogen) was added to a final concentration of 50 units/ml and the mixture incubated at 37° C. in 5% $CO_2$ for two more days.

(3) On the seventh day, Mitomycin C was added to a concentration of 50 microgram/ml was added to stop growth of the now differentiated dendritic cell culture. The solution was incubated for 60 minutes at 37° C. in 5% $CO_2$. Dendritic cells were collected by gently scraping the adherent cells off the bottom of the flask with a cell scraper. Adherent and non-adherent cells were then centrifuged at 600G for 5 minutes, washed in DPBS and counted.

(4) The prepared dendritic cells were placed into a 96 well round bottom array at $2 \times 10^4$/well in 100 microliter total volume of AIM V media.

CD4+ T cells were prepared from frozen aliquots of the peripheral blood cell samples used to prepare the dendritic cells using the human CD4+ Cellect Kit (Biotex) as per the manufacturers instructions with the following modifications: the aliquots were thawed and washed such that approximately 108 cells will be applied per Cellect column; the cells were resuspended in 4 ml DPBS and 1 ml of the Cell reagent from the Cellect Kit, the solution maintained at room temperature for 20 minutes. The resultant solution was centrifuged for five minutes at 600G at room temperature and the pellet resuspended in 2 ml of DPBS and applied to the Cellect columns. The effluent from the columns was collected in 2% human serum in DPBS. The resultant CD4+ cell solution was centrifuged, resuspended in AIMV media and the density counted.

The CD4+ T-cell suspension was resuspended to a count of $2 \times 10^6$/ml in AIM V media to facilitate efficient manipulation of the 96 well plate.

Peptide antigen is prepared from a 1M stock solution in DMSO by dilution in AIM V media at a 1:10 ratio. 10 microliters of the stock solution is placed in each well of the 96 well plate containing the differentiated dendritic cells. 100 microliter of the diluted CD4+ T-cell solution as prepared above is further added to each well. Useful controls include diluted DMSO blanks, and tetanus toxoid positive controls.

The final concentrations in each well, at 210 microliter total volume are as follows:
$2 \times 10^4$ CD4+
$2 \times 10^5$ dendtritic cells (R:S of 10:1)
5 mM peptide

Example 3

Testing for Reduced Allergenicity in Protease Variants by Whole Enzyme/human Cell in Vitro Proliferation Assay Rationale:

This assay was designed to test in vitro proliferative responses by human peripheral blood mononuclear cells (PBMC) to a peptide of interest (P1, BPN'-Y217L) and its variants. P1 and the enzyme variants were inactivated by treatment with phenyl methyl sulfonyl fluoride ("PMSF"). Human PBMC were cultured with increasing doses of inactivated P1 and all the variants to be tested. The variants tested in these experiments were:

LAP 1: BPN'-Y217L; I79A
LAP 2: BPN'-Y217L; I79A; I122A
LAP 3: BPN'-Y217L; N76D; I122A
LAP 4: BPN'-Y217L; N76D; I79A; I122A
LAP 5: BPN'-Y217L; N76D

Proliferation to P1 indicated that the whole molecule had been processed and presented to T cells by the antigen-presenting cells in the PBMC population. A lack of proliferation to the variants could indicate where amino acid modifications have successfully inhibited the processing, presentation and/or T cell recognition of the P1 epitopes.

Methods:

Human buffy coat samples were obtained from the Stanford University Blood Center (Palo Alto, Calif.). PBMC were isolated by density separation, washed in Dulbecco's phosphate buffered saline ("DPBS") and counted.

P1 and its variants were inactivated by PMSF: 100 mM PMSF in 100% ethanol was added to a 2 mg/ml solution of the enzymes in Dulbeccos phosphate buffered saline ("DPBS") at a 1:50 dilution. The mixture was vortexed and allowed to stand at room temperature for 5 minutes. The PMSF was added again at a 1:50 dilution, and allowed to stand another 5 minutes. PMSF was added a third time, allowed to stand an additional 5 minutes and residual enzyme activity was assessed on the colorometric substrate succinyl-Ala-Ala-Pro-Phe-para-nitroanilide assay (SEQ ID NO: 6) (Delmar, EG, et al, (1979)).

PBMC were resuspended at a concentration of $2 \times 10^6$ cells/ml in 5% human AB-sera, RPMI 1640 (pen/strep/glutamine). Cells were plated at 2 mls/well in 24 well plates, and enzymes were added. Each donor was tested with P1, and as many of the variants as could be tested (cell number limitations). Enzyme concentrations used throughout most of these studies were 1, 5 10 and 20 ug/ml. The last nine experiments were performed with an extended dose range of 5, 10, 20 and 40 ug/ml enzyme. However, for consistency the data compiled here is based on the top dose of 20 ug/ml. Cultures were incubated at 37° C., 5% $CO_2$ for 5 days. On day 5, the cultures were resuspended by pipetting, and 100 ul replicates from each well were transferred to 96 well plates. The wells were pulsed with tritiated thymidine (0.5 uCi/well) and incubation was allowed to proceed for 6 hours at 37° C. The plates were then harvested, and incorporated counts where determined.

Results

Between 30 and 40 individuals were tested for their responses to P1 and the P1-based variants (e.g., LAP1–LAP5). The LAP5 enzyme was added to the protocol later, and only 18 individuals were tested with that variant. The results for all individuals were compiled and are presented in the table and graph below. A result was called positive ("yes") if there was a stimulation index (S.I.) of greater than or equal to 2.0 at the higher doses. A response was called weak if it displayed an S.I. less than 2.0, but above the background (FIG. 4)

Sixty percent of all the donors tested mounted a proliferative response to P1 with an S.I. of 2.0 or better. The responses to all 6 enzymes were compiled, and are represented in the table below:

TABLE 1

| P1 | LAP1 | LAP2 | LAP3 | LAP4 | LAP5 |
|---|---|---|---|---|---|
| n = 40 | n = 40 | n = 37 | n = 34 | n = 33 | n = 18 |
| 22% no | 87% no | 65% no | 82% no | 69% no | 83% no |
| 17% weak | 2% weak | 11% weak | 3% weak | 18% weak | 11% weak |
| 60% yes | 10% yes | 24% yes | 15% yes | 12% yes | 5% yes |

Many individuals who have positive responses to the variants had much lower responses than to the parent P1 molecule.

Conclusions:

All variants tested induce a lower percent of responders. All the variants include amino acid changes to the 70–84 region, either the N76D change, or the I79A change. A few donors responded to each of the variants, suggesting that the variants could be processed and presented by antigen-presenting cells in the cultures. However, responses to the variants were always lower than to the parent molecule P1. In only one individual of 40 tested (T78186) was there a response to a variant in the absence of a response to the parent enzyme. This donor responded to LAP1 and LAP2, but not to LAP3, LAP4 or LAP5.

Example 4

Determination of Specific Altered Allergenicity Residue within an Epitope

Peptide variants based on the 70–84 sequence of P1 were tested in the Stickler, et al mapping assay with 20 community donor blood samples. A set of peptides was constructed by Mimostopes (San Diego, Calif.). For each of the peptide variants, three amino acid offset 15-mers were constructed to cover the entire region of the proposed change. This was done to ensure that we do not create a new T cell epitope in another 3-mer "reading frame" when the variant is incorporated into a low allergenic protease. The parent peptides in the set were analyzed by mass spectrometry and found to be approximately 70% intact 15-mer.

The peptide sequences were as follows:

| Peptide | | |
|---|---|---|
| 70-84 | GTVAALNNSIGVLGV | (SEQ ID NO: 7) |
| I79A | GTVAALNNSAGVLGV | (SEQ ID NO: 8) |
| N76D | GTVAALDNSIGVLGV | (SEQ ID NO: 9) |
| N76D/I79A | GTVAALDNSAGVLGV | (SEQ ID NO: 10) |
| V81A | GTVAALNNSIGALGV | (SEQ ID NO: 11) |
| N76D/V81A | GTVAALDNSIGALGV | (SEQ ID NO: 12) |
| I79T | GTVAALNNSTGVLGV | (SEQ ID NO: 13) |
| N76D/I79T | GTVAALDNSTGVLGV | (SEQ ID NO: 14) |

The three-mer offsets across each region are not shown for clarity.

Twenty blood samples were used to test all of the peptide variants. Peptides were used at 5 uM. In this cohort, it was found that 50% of the donors responded to the 70–84 region FIG. 4b. All of the 70–84 variants induced significantly fewer responses. Note that only one responded to the I79A peptide and no others responded to N76D peptide, illustrating the reduction of the immunogenic response of the variant subsequent to the specified peptide modification.

Example 5

Determination of Specific Altered Allergenicity Residue within a Second Eptitope A set of alanine substituted peptides describing the 109–123 region of P1 were tested in the standard priming assay procedure (Stickler, M M, et al. J. Immunother. 23(6): 654–660 (2000). The sequence at 109–123 was: NGIEWA-IANNMDVIN (SEQ ID NO: 15). The alanine substituted peptides are as depicted in FIG. 6 (SEQ ID NO: 15–17 and 19–30). The non-responders are depicted in FIG. 4c.

Figure 5:
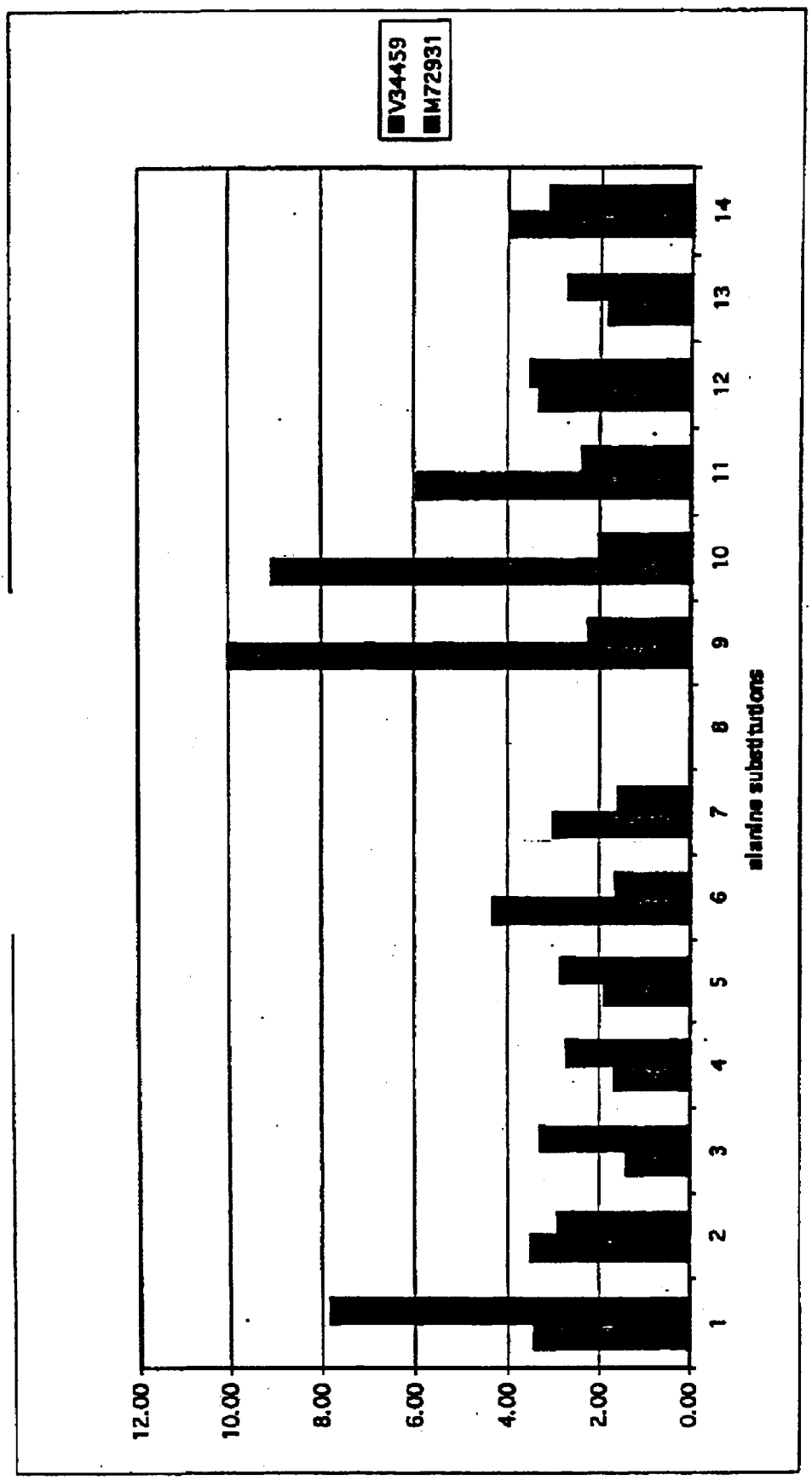
FIG. 5 illustrates the stimulation index (SI) of P1 (BPN'-Y217L) 109–123 residue site responders.
Figure 7:
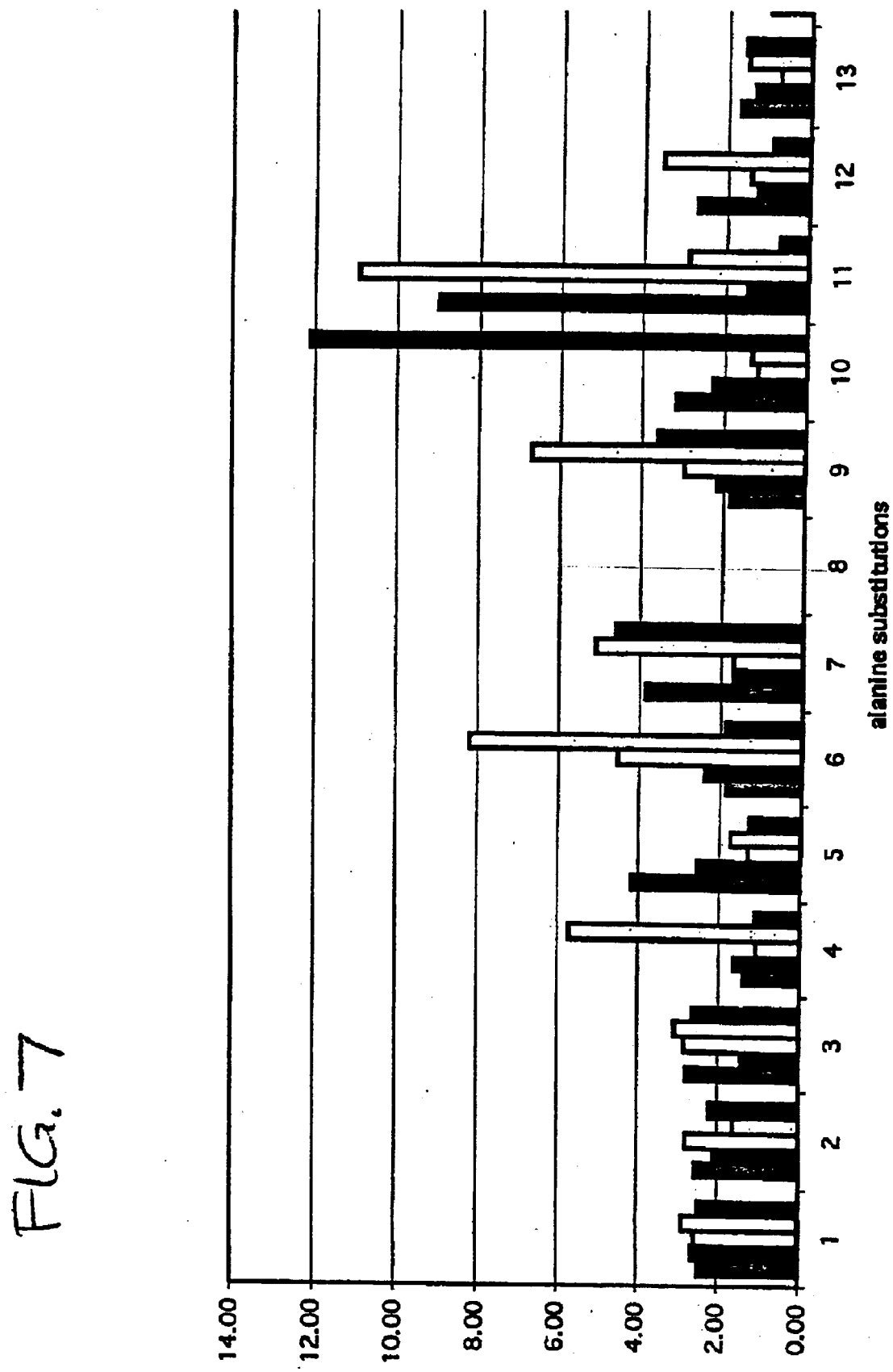
FIG. 7 illustrates the stimulation index (SI) of five human subjects as exposed to the synthesized alanine peptides of FIG. 6.

A total of twenty community donors were tested. Two individuals reached an Stimulation Index ["SI"] of 3 or more (FIG. 5), consistent with the low percent of naïve responders to this region. In order to make a more robust assessment of anchor residues, the data for all individuals whose SI response to the control peptide was 2 or better was also compiled (FIG. 7). From this data, the change at position 13 was deemed best for reducing immunogenicity, as none of the non-responders mounted a response to this change (FIG. 7) and all responders with an SI of 2 or better to the control peptide exhibited reduced proliferation to this changed peptide. The amino acid change in peptide #13 is designated I122A, and would be this sequence: NGIEWAIANNMDVAN (SEQ ID NO: 16).

In addition, from this data, a change at position 11 was deemed best for increasing the immunogenic response as three of five responders with an SI of 2 or better to the control peptide exhibited increased proliferation to this changed peptide. The amino acid change in peptide #11 is designated D120A and would be this sequence: NGIEWAIANNMAVIN (SEQ ID NO: 17).

Example 6

Reduction of Allergenicity in Vivo HLA-DR3/DQ2 Mouse T Cell Responses to P1

Methods:

The HLA-DR3/DQ2 transgene was bred onto an MHC class II knockout (C2D) background to create the mice used in this study (Cosgrove D, et al, Cell 66:1051–66 (1991). Both male and female mice were used in these studies. Animals ranges in age from one year to 6–8 weeks. All animals were bred and maintained in the Aviron Animal Facility (Mountain View, Calif.), an AALAC accredited facility. Animals were assessed by flow cytometry and found to express high levels of HLA-DR, and low levels of HLA-DQ using two different anti-HLA-DQ antibody reagents. Females express overall higher levels of HLA molecules than males. Animals were immunized by a number of routes, including footpad immunizations in complete Freund's adjuvant (CFA), intraperitoneal immunization in CFA, and intraperitoneal immunization with P1 precipitated on alum. Some animals were immunized by multiple routes.

Figure 7B:
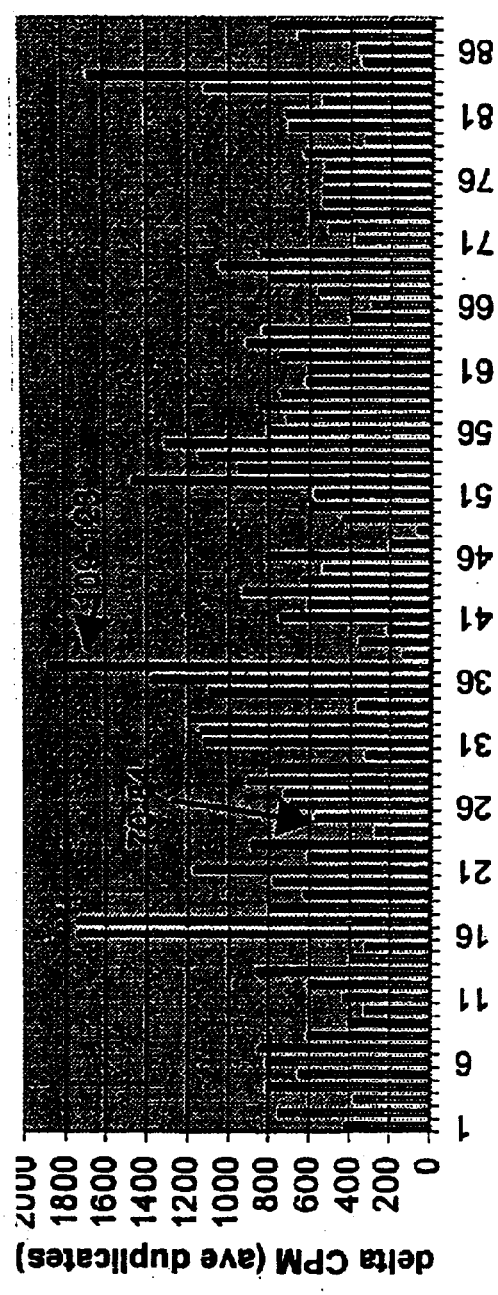
FIG. 7b illustrates the responses of female HLA-DR3/DQ2 P1 in alum.
Figure 7C:
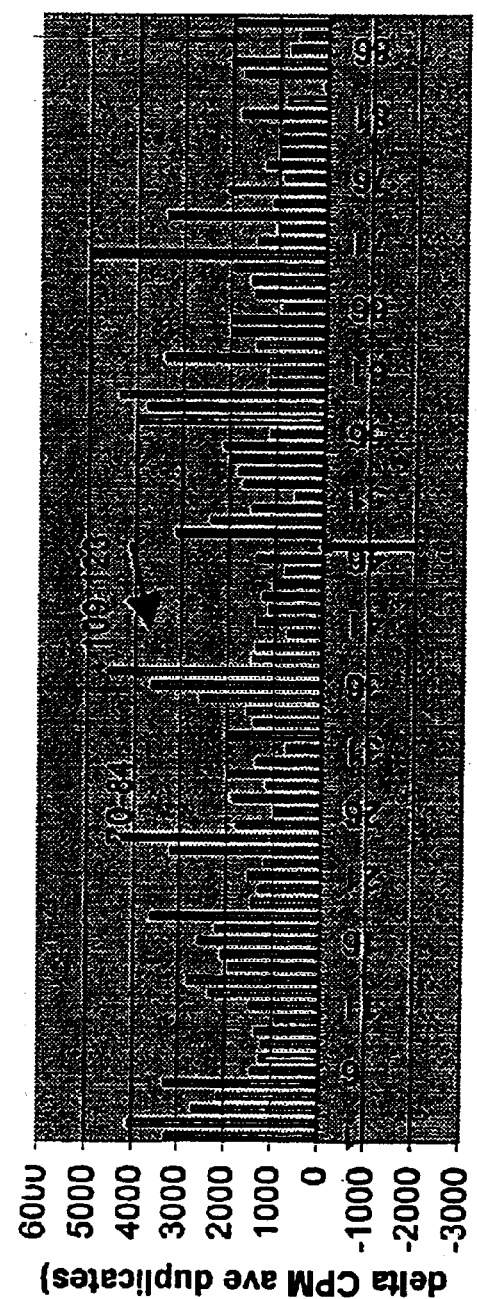
FIG. 7c illustrates the responses of male HLA-DR3/DQ2 P1 in alum.
Figure 8:
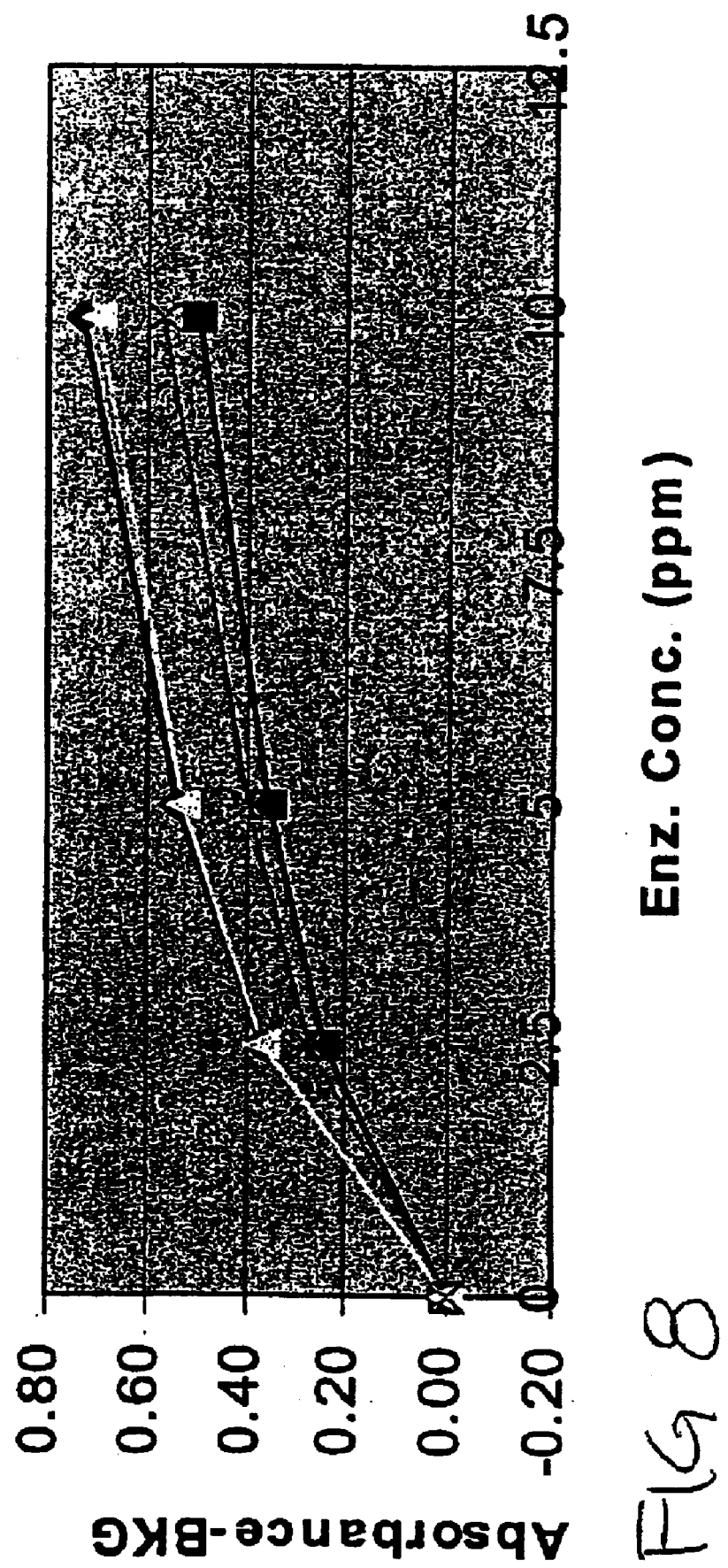
FIG. 8 illustrates the hydrolysis of a 5 mg/ml dimethyl casein substrate solution at pH 5.5 as indicated by the change in substrate absorbance by different concentrations of the subtilisin variants (P1-◇-; -□-LAP2; -Δ-LAP3; and -x-LAP4).
Figure 9:
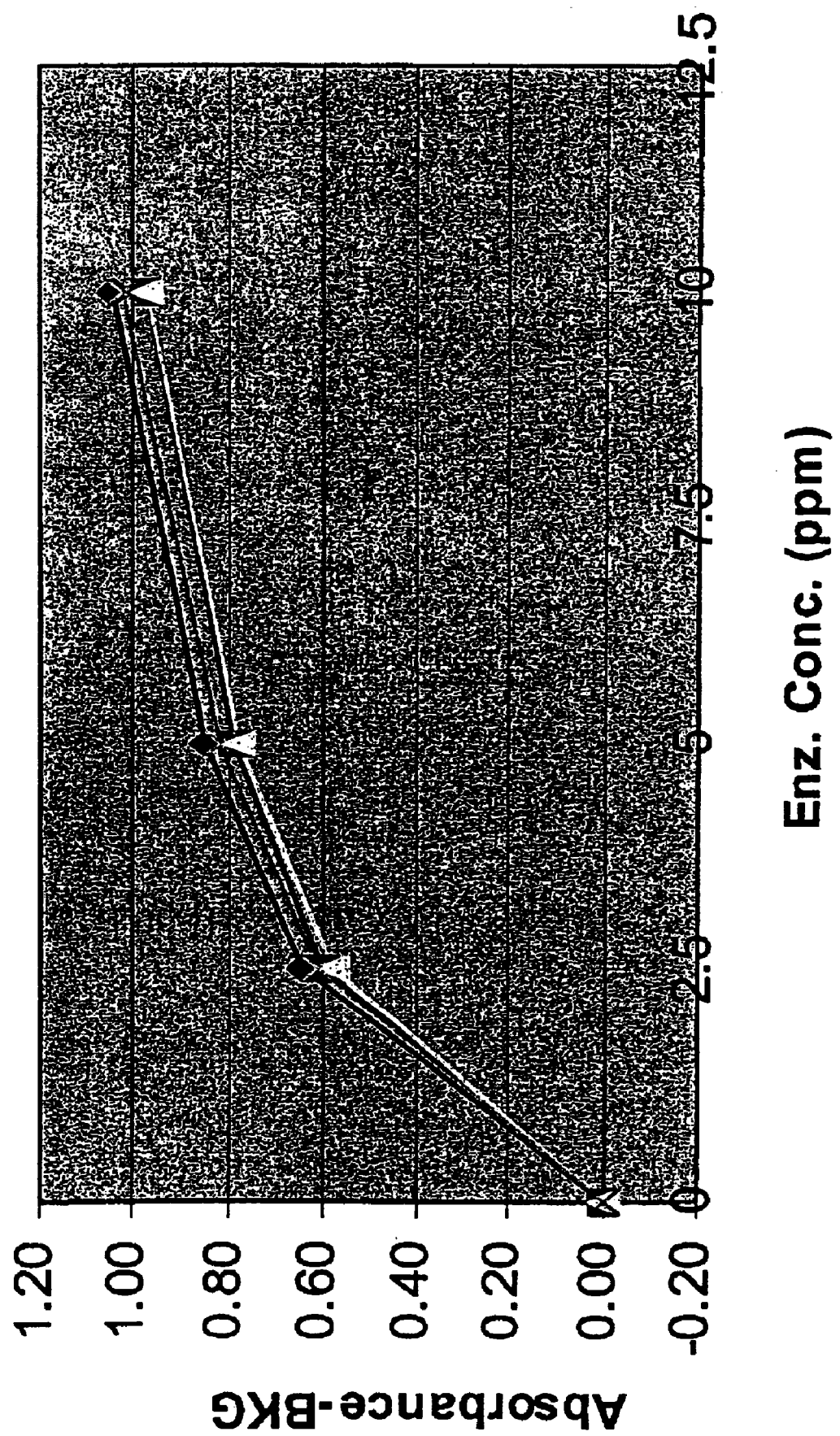
FIG. 9 illustrates the hydrolysis of a 5 mg/ml dimethyl casein substrate solution at pH 6.5 as indicated by the change in substrate absorbance by different concentrations of the subtilisin variants (P1-◇-; -□-LAP2; -Δ-LAP3; and -x-LAP4).
Figure 19:
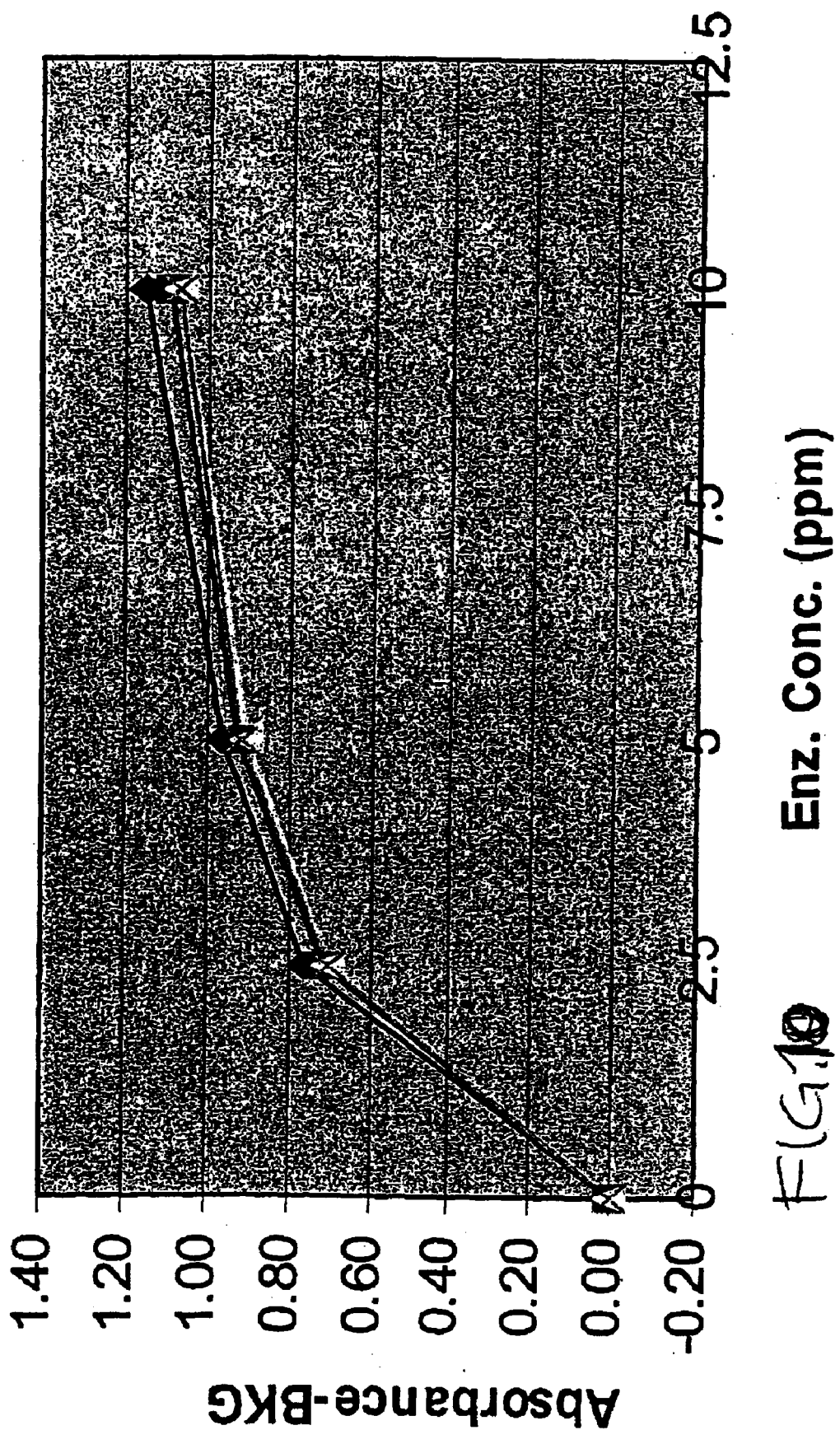

Results:

To verify that the HLA-DR3/DQ2 mice are processing and presenting the 70–84 and/or the 109–123 epitopes from intact P1 enzyme, the splenocyte responses were epitope mapped in P1 immunized mice. Female and male mice were immunized three times with 10 ug of P1 in alum, on days 1, 3 and 10. The spleens were removed on day 15. Splenocytes from the female mice were placed in vitro at $10^6$ cells per well with 50 ug/ml of P1 peptides. Splenocytes from the 5 male mice were pooled, and duplicate cultures were set up as described for the female mouse splenocytes. The cultures were pulsed with 0.5 uCi tritiated thymidine at 24 hours, and harvested at 48 hours. The counts for replicate cultures were averaged, and the background was subtracted. The background counts for each culture were 2486±218 cpm for the Female HLA-Dr3/DQ2 P1 in alum (FIG. 7a) and 5314±529 cpm for the Male HLA-DR3/DQ2 P1 in alum (FIG. 7B). The female mice responded to 20 ug/ml of PMSF inactivated P1 in culture with an SI of 2.2, the male splenocytes with an SI of 1.7. Responses to 10 ug/ml PHA were robust, with the females showing an SI of 18 and the males an SI of 10.

Both groups of mice (male and female described above) mounted a noticeable response to the 109–123 peptide. A response to 70–84 was missing in female mice immunized by this route. However, the male mice exhibited a response to this peptide.

Example 7

Construction of Low Allergenic Stable Protease Variants

After determining the location of a T-cell epitope, protease variants were constructed using established protein engineering techniques. The variants were constructed so that a highly allergenic amino acid sequence of a protein was replaced with a corresponding sequence from a less allergenic homolog. In this instance, various residues were substituted in a B. amyloliquefaciens mutant subtilisin (P1). The manufacture of protease P1 is disclosed in U.S. Pat. No. RE 34,606, European patent 130,756 and U.S. Pat. No. 5,441,882. The variant P1 gene and chloramphenicol marker gene are flanked by a repeated sequence corresponding to sequence 5' to the apre E loci for amplifying copy number by using chloramphenicol selection.

Three protease mutants were constructed.

LAP 2

A protease variant LAP 2 was introduced into P1 (BPN'-Y217L) by converting I79 to an alanine and I122 to an alanine by site-directed mutagenesis in a pBluescript based vector.

In the resulting LAP 2 plasmid, a sequence 5' to the aprE locus was repeated after the chlorophenicol gene for amplifying gene copy number by using increasing chloramphenicol concentrations. The LAP2 plasmid was transformed into a Bacillus production stain using a standard transformation procedure. Transformants were selected on LA plates containing 5 µg/ml chloramphenicol. The transformants were grown and subcultured in LB media with increasing levels of chloramphenicol to amplify the copy number of LAP2 on the chromosome. After amplification of the LAP2 strains to 25 µg/mi chloramphenicol, the LAP2 transformants were plated on LA+25 µg/ml chloramphenicol containing 1% skim milk and assayed for the presence of halos which indicated protease activity. LAP2 amplified strains made halos in the skim milk plate assay.

LAP 3

A protease variant LAP 3 was introduced into P1 by replacing N76 with an aspartic acid residue and replacing the I122 with an alanine by site-directed mutagenesis in a pBluescript based vector to create LAP3. LAP3 was transformed into the Bacillus production strain and amplified as described above and plated on skim milk plates. LAP3 transformants made halos in the skim milk plate assays.

LAP 4

A protease variant LAP 4 was introduced into P1 by replacing N76 with an aspartic acid residue, I79 with an alanine residue and I122 with an alanine by site-directed mutagenesis in a pBluescript based vector to create LAP4. LAP4 was transformed into the Bacillus production strain and amplified as described above and plated on skim milk plates. LAP4 transformants made halos in the skim milk plate assays.

Example 8

Lower Allergenicity Protease Stabilizing Mutations (N76D, I79A, I122A, N218S, Q206L, P40Q, D41A, H238Y)

Variants made to increase stability by site-directed mutations are listed below:

P1-N76D/I79A/I122A/N218S;
P1-N76D/I79A/I122A/Q206L;
P1-N76D/I79A/I122A/Q206L/N218S;
P1-I79A/I122A/Q206L;
P1-I79A/I122A/N218S;
P1-I79A/I122A/P40Q;
P1-I79A/I122A/D41A; and
P1-I79A/I122A/H238Y Each protease variant was introduced into P1 by replacing the respective residues as desired (e.g. N76 with an aspartic acid residue, I79 with an alanine residue, I122 with an alanine residue, Q206 with a lysine residue, N218 with a serine residue, P40 with a glutamine residue, D41 with an alanine residue, and H238 with a tyrosine residue) by site-directed mutagenesis in a pBluescript based vector to create the respective stabilized LAP variant. Each stabilized LAP variant was transformed into the *Bacillus* production strain and amplified as described above and plated on skim milk plates. LAP transformants made halos in the skim milk plate assays.

Example 9

Lower Allergenicity Protease Stabilizing Mutations (A216K, D181G, S101V, G215A, A216E, L217S, R247Y, R247S, R247Q, G48S, S101Q/S154G, G128S, S182T, S101R, Y104W/I107V, L250G, T254G, T254A, G258S, M50A, G47S, A48G, S182R, S183R, Q185A, S101R/I107V, S248G, Y262F)

Variants made to increase stability by site-directed mutations are listed below:

P1-N76D/I79A/I122A/A216K;
P1-N76D/I79A/I122A/D181G;
P1-N76D/I79A/I122A/S101V;
P1-N76D/I79A/I122A/G215A;
P1-N76D/I79A/I122A/A216E;
P1-N76D/I79A/I122A/L217S;
P1-N76D/I79A/I122A/R247Y;
P1-N76D/I79A/I122N/R247S;
P1-N76D/I79A/I122A/R247Q;
P1-N76D/I79A/I122A/G46S;
P1-N76D/I79A/I122A/S101Q/S154G;
P1-N76D/I79A/I122A/G128S;
P1-N76D/I79A/l122A/S182T;
P1-N76D/I79A/I122A/S101R;
P1-N76D/I79A/I122A/Y104W/I107V;
P1-N76D/I79A/I122A/L250G;
P1-N76D/I79A/I122A/T254G;
P1-N76D/I79A/I122A/T254A;
P1-N76D/I79A/I122A/G258S;
P1-N76D/I79A/I122A/M50A;
P1-N76D/I79A/I122A/G47S;
P1-N76D/I79A/I122A/A48G;
P1-N76D/I79A/I122A/S182R;
P1-N76D/I79A/I122A/S183R;
P1-N76D/I79A/I122A/Q185A;
P1-N76D/I79A/I122A/S101R/I107V;
P1-N76D/I79A/I122A/S248G; and
P1-N76D/I79A/I122A/Y262F;

Each protease variant was introduced into P1by replacing the respective residues as desired (e.g. N76 with an aspartic acid residue, I79 with an alanine residue, I122 with an alanine residue, A216 with a lysine residue, D181 with a glycine residue, S101 with a valine residue, G215 with an alanine residue, etc.) by site-directed mutagenesis in a pBluescript based vector to create the respective stabilized LAP variant. Each stabilized LAP variant was transformed into the *Bacillus* production strain and amplified as described above and plated on skim milk plates. LAP transformants made halos in the skim milk plate assays.

Example 10

Hydrolysis of Dimethyl Casein ("DMC") by Mutant Variant Subtilisin

Mutant variant subtilisin (P1, LAP2, LAP3, and LAP4), isolated and purified by the methods described herein, were analyzed for their ability to hydrolyze a commercial synthetic substrate, di-methyl casein (Sigma C-9801). A 5 mg/ml DMC substrate solution was prepared in the appropriate buffer (5 mg/ml DMC, 0.005% (w/w) Tween 80® (polyoxyethylene sorbitan mono-oleate, Sigma P-1754)). The appropriate DMC substrate buffers were as follows: 50 mM Sodium acetate for pH 5.5; 50 mM N-tris (hydroxymethyl)methyl-2-aminoethane sulfonic acid ("TES") for pH 6.5; 50 mM piperazine-N-N'-bis-2-ethane sulfonic acid ("PIPES") for pH 7.5; and 50 mM Tris for pH 8.5. 200 µl of the desired pH substrate was transferred into 96 well microtiter plate and were pre-incubated at 37° C. for twenty minutes prior to enzyme addition. A 2,4,6-trinitrobenzene sulfonate salt ("TNBS") color reaction method was determined on a Spectra Max 250 spectrophotometer. This assay measure the enzymatic hydrolysis of DMC into peptides containing free amino groups. These amino groups react with 2,4,6-trinitro-benzene sulfonic acid to form a yellow colored complex, as depicted in the following reaction:

Thus the more deeply colored the reaction, the more activity is measured. The TNBS detection assay was performed on the supernatent after two hours of incubation at 37° C. A 1 mg/ml solution of TNBS was prepared in a reagent (2.4 g NaOH, 45.4 g $Na_2B_4)_7 \cdot 10H_2O$ dissolved by heating in 1000ml). 60 µl were aliquoted into a 96-well microtiter plate. 10 µl of the incubated enzyme solution described above were added to each well and mixed for 20 minutes at room temperature. 20 µl of $NaH_2PO_4$ solution (70.4 g $NaH_2PO_4$ $H_2O$ and 1.2 g $Na_2SO_3$ in 2000 ml) were for 1 minute in the wells to stop the reaction and the absorbance at 405 nm in a SpectraMax 250 spectrophotometer was determined. A blank (same TNBS solution sans enzyme) was also prepared. The hydrolysis was measured by the following formula:

$Absorbance_{405}$(Enzyme solution)−$Absorbance_{405}$(without enzyme)

at varying enzyme concentrations (0, 2.5, 5, 7.5, and 10 ppm). The data in FIGS. 8a–10 show the comparative ability of the mutant variants to hydrolyze such substrate versus proteases from a known mutant variant (P1).

As can be seen in the figures, all three enzymes showed significant hydrolysis of DMC substrates at different pH's and different enzyme concentrations.

Example 11

Hydrolysis of Collagen, Elastin, and Keratin by Variant Proteases

Mutant variant subtilisin (P1, LAP2, LAP3, and LAP4), isolated and purified by the methods described above, were analyzed for their ability to hydrolyze commercial substrates, bovine collagen (Sigma C-9879), bovine elastin (Sigma E-1625), and bovine keratin (ICN Biomedical 902111). A 5 mg/ml substrate solution was prepared (0.005% Tween 80®). Each substrate was prepared in the appropriate pH as described (e.g. pH 5.5, 6.5, 7.5, and 8.5).

1.5 ml of the each substrate was transferred into 24-well Costar plate at 37° C. The plates were pre-incubated at 37° C. for twenty minutes prior to enzyme addition. A TNBS detection assay as described above was performed on the supernatent after two hours of incubation at 37° C.

Figure 11:
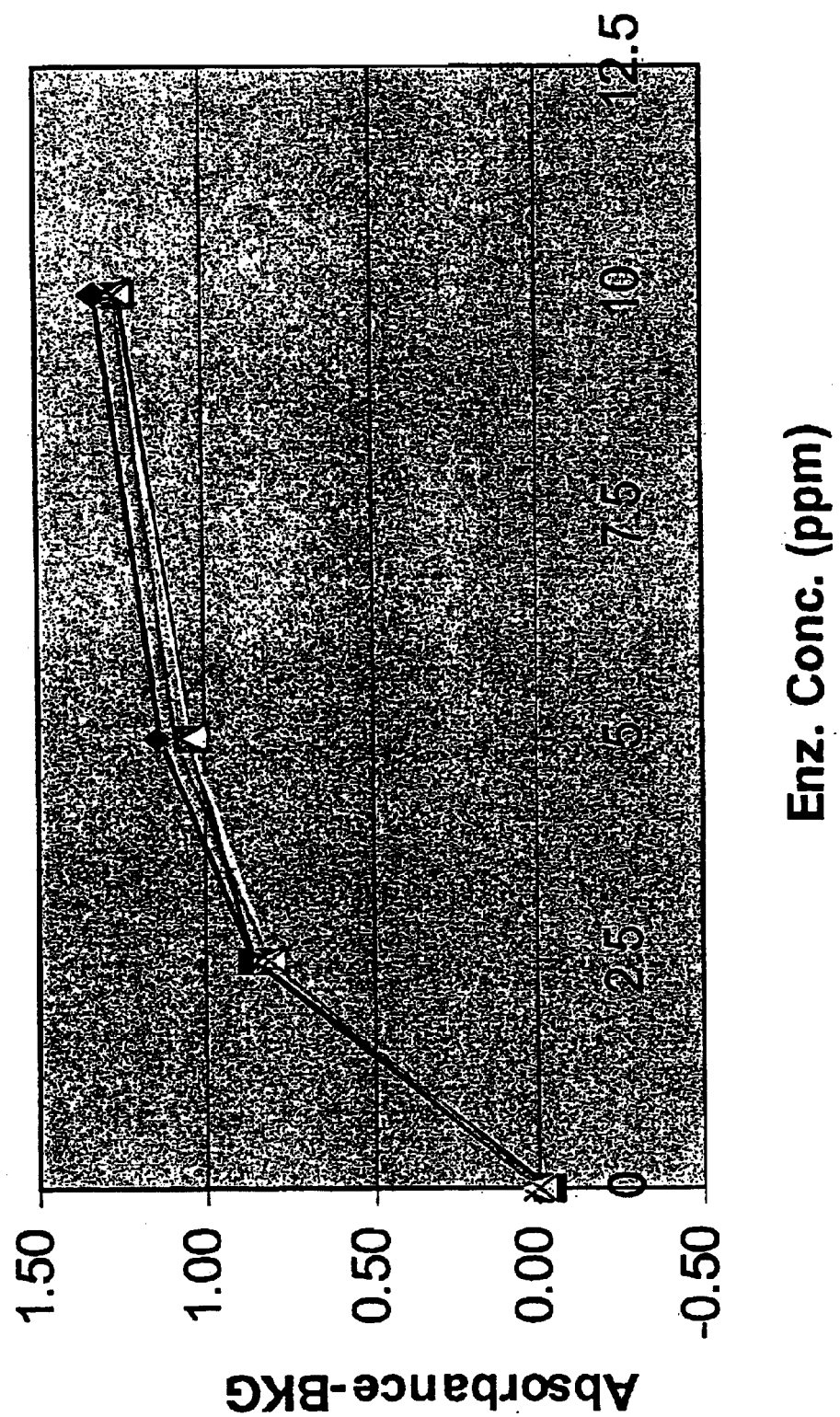
FIG. 11 illustrates the hydrolysis of a 5 mg/ml dimethyl casein substrate solution at pH 8.5 by the change in substrate absorbance by different concentrations of the subtilisin variants (P1-◇-; -□-LAP2; -Δ-LAP3; and -x-LAP4).
Figure 12:
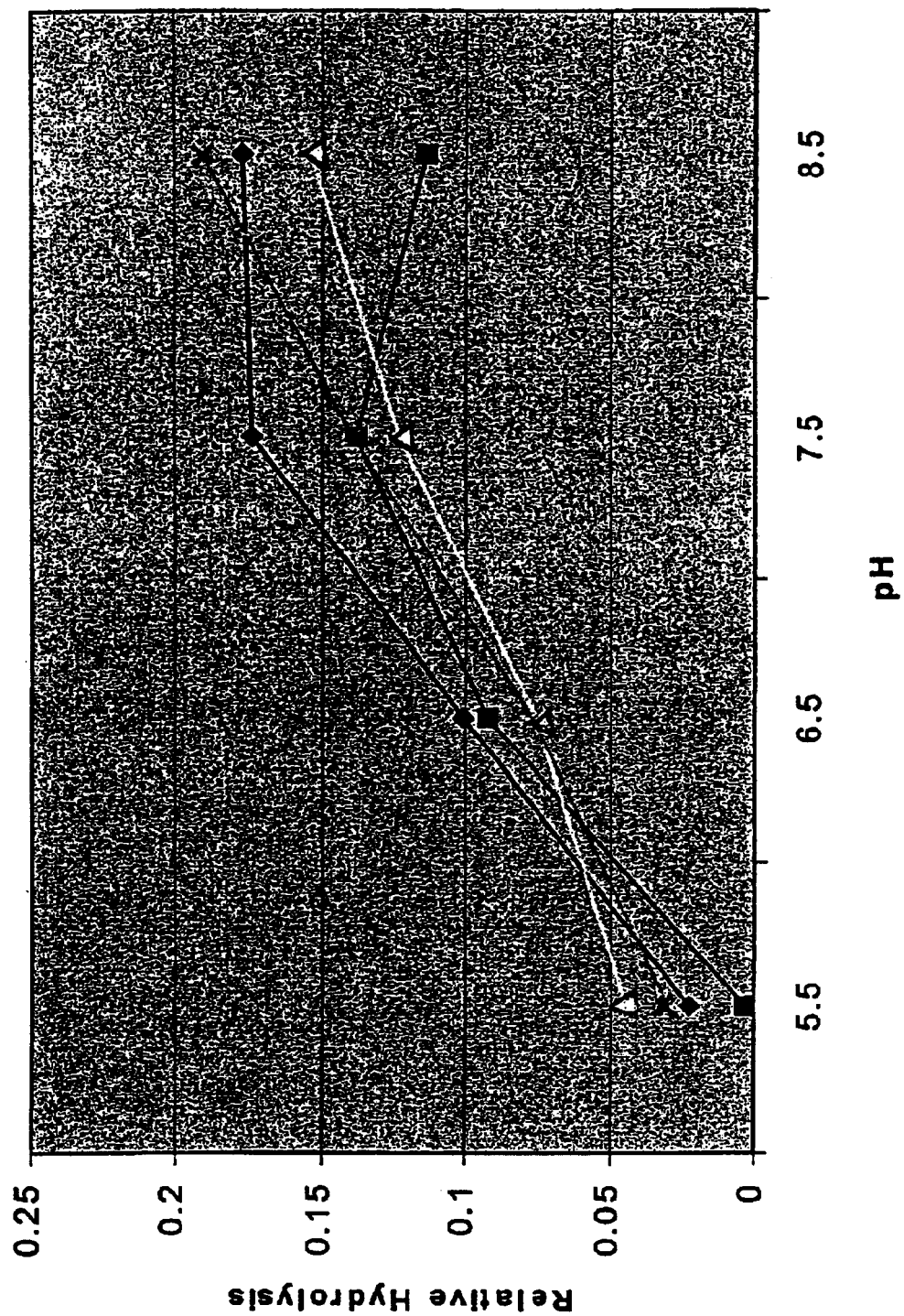
FIG. 12 illustrates the hydrolysis of a 5 mg/ml bovine collagen substrate solution by the change in substrate absorbance at various pH's (5.5–8.5) by different subtilisin variants (P1-◇-; -□-LAP2; -Δ-LAP3; and -x-LAP4).
Figure 13:
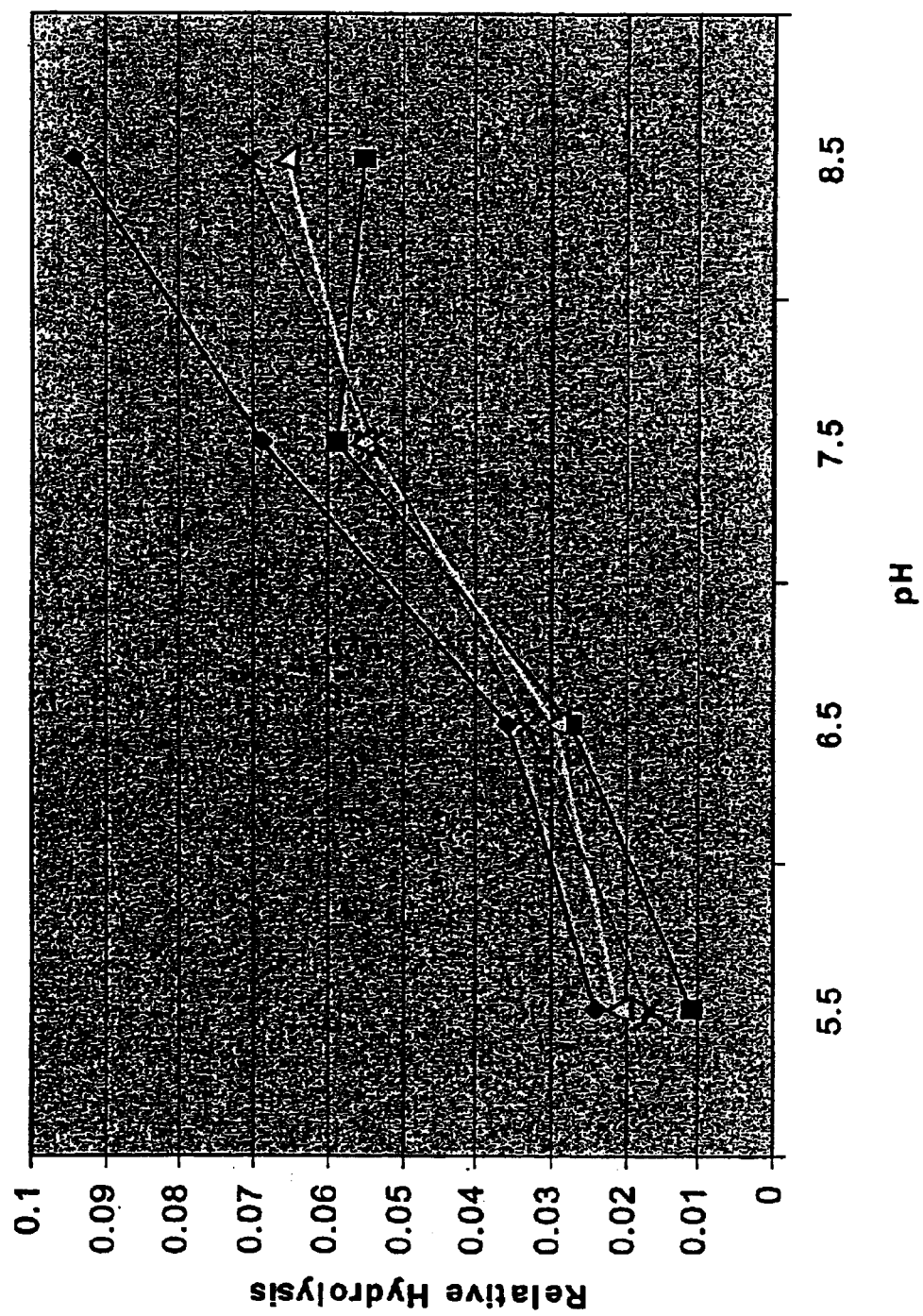
FIG. 13 illustrates the hydrolysis of a 5 mg/ml bovine elastin substrate solution by the change in substrate absorbance at various pH's (5.5–8.5) by different subtilisin variants (P1-◇-; -□-LAP2; -Δ-LAP3; and -x-LAP4).

The data in FIGS. 11–13 show the comparative ability of the mutant variants to hydrolyze such substrates versus proteases from a known mutant variant (P1). Activities are relatively close. Variant LAP 3 hydrolyzed collagen better than the known P1variant and better than the previously described hybrid proteases.

As can be seen in the figures, all three enzymes showed significant hydrolysis of collagen, elastin and keratin substrates at different pH's and different enzyme concentrations.

Example 12

Thermal Stability of Protease Variants in Piperazine-N-N'-bis-2-ethane Sulfonic Acid ("PIPES") Buffer Parameters: Determined in a PCR thermocycler of the type Stratagene Robocycler5.0 ppm enzyme (use one of P1, LAP 2, LAP 3, LAP 4), taken at five timepoints (5, 10, 20, 40 and 60 minutes) at pH 6.5 at each temperature (ranging from 42–56° C. at two degree intervals in the above described PCR thermocycler), measured the stability at every other degree C. from 42–56.

A 50 mM PIPES Buffer was prepared (50 mM PIPES, 0.005% Tween 80®). The pH was adjusted to 6.5.

Samples were assayed using standard succinyl-ala-ala-pro-phe-para-nitro anilide ("SAAPFpNA") assay (Delmar, E. G., et al, *Anal. Biochem.* 94 (1979) 316–320; Achtstetter, *Arch. Biochem. Biophys* 207:445–54 (1981)) (pH 6.5, 25° C.). The samples were diluted to about 300 milliOD/minute. The thermal stability was expressed as enzyme half-life (min) as determined by:

H.L.=ln 2/slope, wherein the slope is the slope of curve of rate v. time for each temperature.

Figure 14:
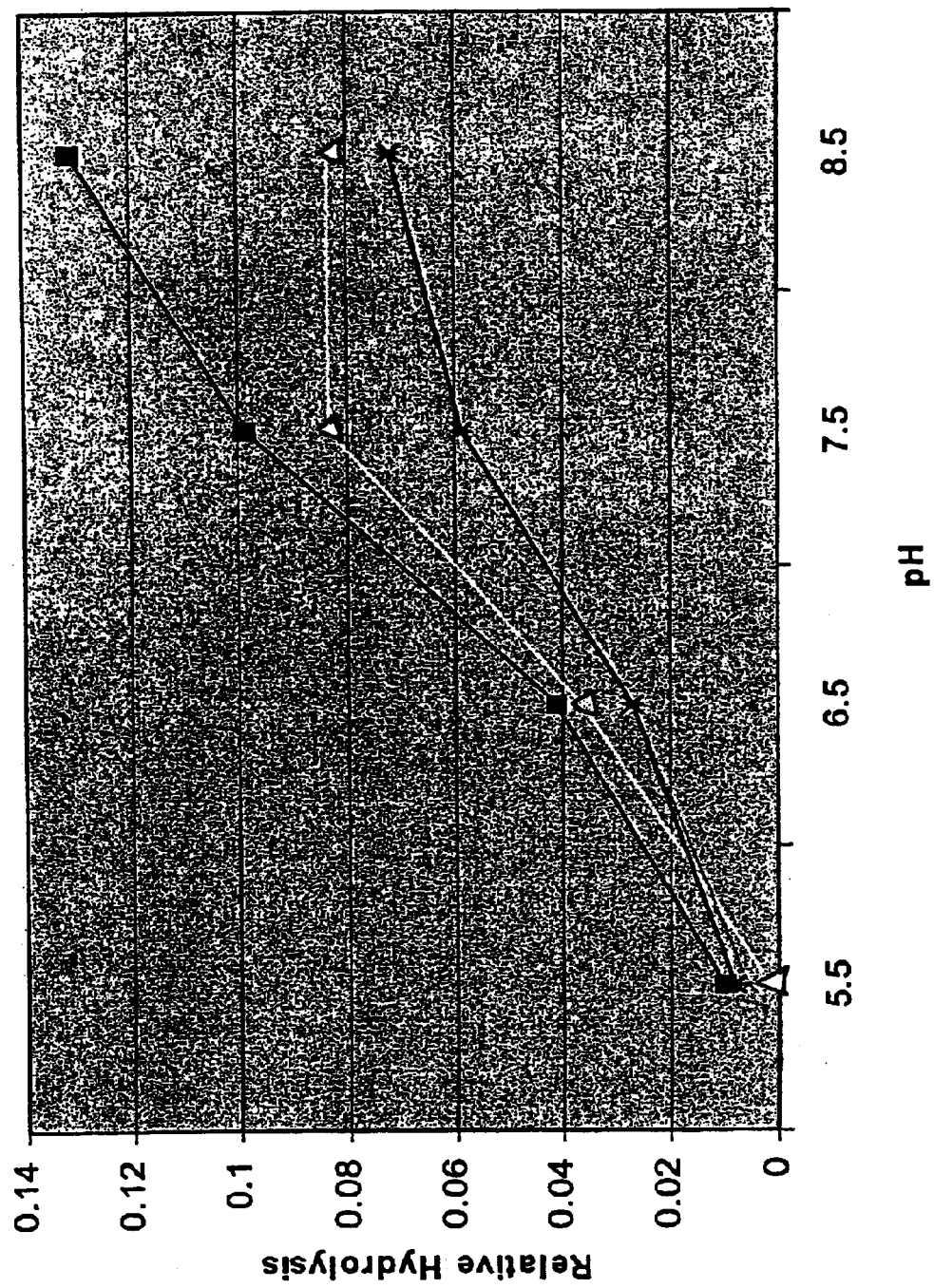
FIG. 14 illustrates the hydrolysis of a 5 mg/ml bovine keratin substrate solution by the change in substrate absorbance at various pH's (5.5–8.5) by different subtilisin variants (P1-◇-; -□-LAP2; -Δ-LAP3; and -x-LAP4).
Figure 5:
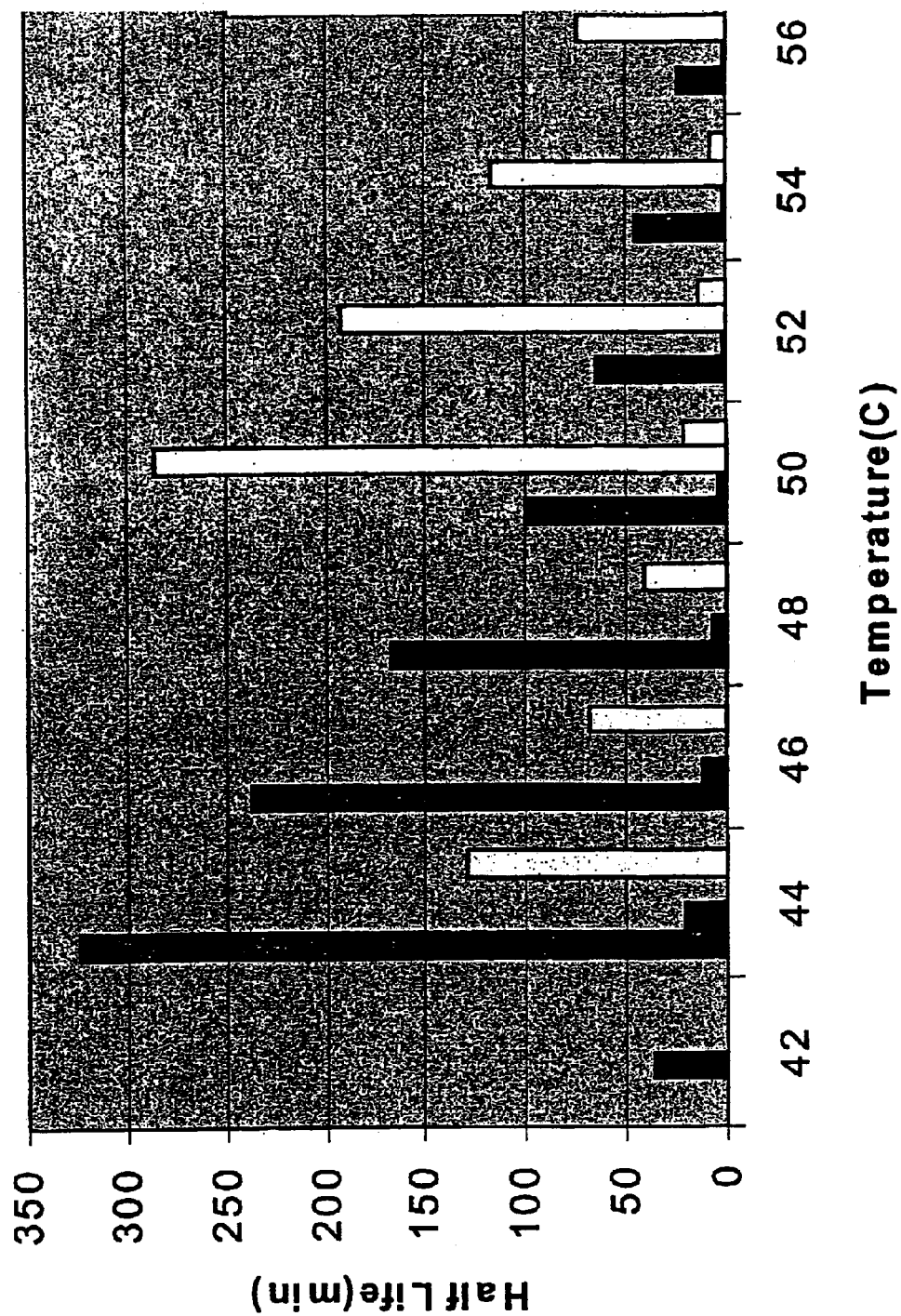
Figure 16:
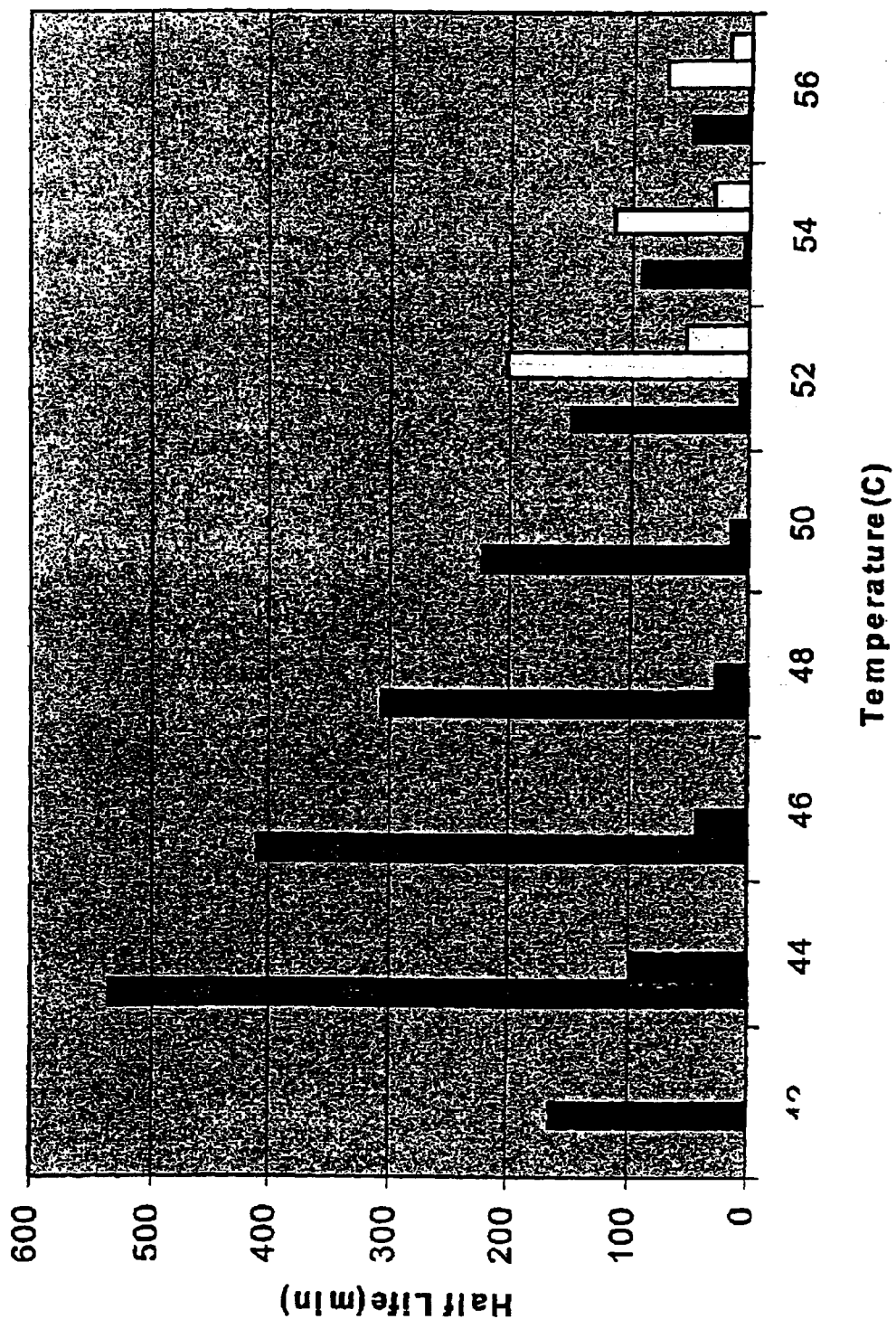
FIG. 16 illustrates the change in enzyme half-life over the temperature range of 42–56° C. as a measure of the thermal stability of the various protease variants in 50mM TES (pH 7.5)(P1-◇-; -□-LAP2; -Δ-LAP3; and -x-LAP4).

As can be seen from FIG. 14 mutant variant LAP 4 had the best stability, better than that of the control P1at greater than 52° C.

Example 13

Thermal Stability of Protease Variants in N-tris (Hydroxymethyl)methyl-2-aminoethanesulfonic acid ("TES")

Parameters: 5.0 ppm enzyme [P1, LAP 2, LAP 3, LAP 4, taken at five timepoints (5, 10, 20, 40, and 60 minutes) at pH 6.5 at each temperature (ranging from 42–56° C. at two degree intervals using the PCR thermocycler temperature gradient described above), measured the stability at every other degree C. from 42–56.

A TES Buffer was prepared by mixing 50 mM TES (Sigma T 1375), 0.005% Tween 80®. The pH was adjusted to 6.5.

Thermal stability of the variants was determined as activity of the residual variant as measured using a succinyl-ala-ala-pro-phe-para-nitroanilide ("AAPFpNA") (Sigma no. S-7388, Mol. Wt. 624.6 g/mole) assay (E. G. Delmar et al., Anal. Biochem. 94 (1979) 316–320, Achtstetter Arch. Biochem. Biophys 207:445–454 (1981)) pH 6.5, 25° C.). The (yellow) p-nitronanilide (pNA) formed was measured spectrophotometrically at 410 nm: $.\epsilon_M = 8{,}480\ M_{-1}.cm_{-1}$, ( ) with a SpectraMax 250 spectrophotometer, the samples being diluted to about 300 mOD/min. The thermal stability was expressed as enzyme half-life (min) as described above.

As can be seen from FIG. 15 mutant variant LAP 4 had the best stability, better than that of the control P1at greater than 50 degrees C.

Example 14

Hydrolysis of Dimethyl Casein ("DMC") and Keratin by Mutant Variant Subtilisin

The enzyme activity of variants prepared as described in Example 9 was compared against that of LAP2 enzymatic activity using DMC and keratin substrates as described by the methods set forth in Examples 10 and 11. The results are summarized in Table 2.

TABLE 2

| | Enzyme activity compared to LAP2 | |
|---|---|---|
| Mutation | DMC | Keratin |
| LAP2-A216K | | > |
| LAP2-D181G | > | > |
| LAP2-S101V | > | > |
| LAP2-G215A | > | > |
| LAP2-A216E | > | > |
| LAP2-L217LS | > | > |
| LAP2-R247Y | > | > |
| LAP2-R247S | > | > |
| LAP2-R247Q | > | > |
| LAP2-G46S | > | > |
| LAP2-S101G-S154G | > | > |
| LAP2-G128S | > | > |
| LAP2-S182T | > | > |
| LAP2-S101R | > | > |
| LAP2-Y104W-I107V | > | > |
| LAP2-L250G | > | > |
| LAP2-T254G | > | > |
| LAP2-T254A | > | > |
| LAP2-G258S | > | > |
| LAP2-M50A | > | > |
| LAP2-G47S | > | > |
| LAP2-A48G | > | |
| LAP2-S182R | | > |
| LAP2-S183R | > | > |
| LAP2-Q185A | > | |
| LAP2-S101R-I107V | > | |
| LAP2-S248G | > | > |
| LAP2-Y262F | > | > |

Example 15

Stability of Protease Variants in Bodywash Solution

Using the cloned enzymes (as described in Example 1), stability of various protease variants were measured using the following protocol. The results are summarized in the Table below.

Method to Measure Bodywash Solution Stability

Parameters: (P1, LAP2, LAP3, LAP4), 30 minutes at 45° C. in one study and 30 minutes at 50° C. in a second study.

50/50 (w/w) Bodywash solution was prepared by mixing a bodywash sold under the trademark ZEST® (Procter & Gamble, Cincinnati, Ohio), with deionized water. The pH of the buffer blend was around 6.8.

The enzymes to be tested were diluted such that their final enzyme concentration in a 50 w/w % BodyWash:deionized water solution would produce a change in $OD_{405}$ of 0.5 to 1.0 when 10 μl of the enzyme/body wash solution was assayed using SAAPFpNA assay endpoint method (Delmar, et al 1979). Once the amount of dilution was ascertained, 200 μl of the diluted mixture was placed into 96 well microtiter plate wells. The plate was sealed and placed in a water bath at 40° C., in one study, and at 50° C., in another study. The plates were removed from the water bath after 45 minutes and 10 μl samples were assayed by the endpoint method. The % remaining was calculated as 100 times the final activity divided by the initial activity.

TABLE 3

| VARIANT | % Remaining Activity 40° and 50° C. | |
|---|---|---|
| | 40° | 50° |
| Y217L* | 84 | 11 |
| Y217L, N76D, I122A | — | 71 |
| Y217L, N79A, I122A | 56 | 11 |
| Y217L, N76D, N79A, I122A | 75 | 29 |
| Y217L, N76D, N79A, I122A, N218S | 94 | 64 |
| Y217L, N76D, N79A, I122A, Q206L | 90 | 58 |
| Y217L, N76D, N79A, I122A, Q206L, N218S | 105 | 84 |
| Y217L, N79D, I122A4, Q206L | 76 | |
| Y217L, N79D, I122A4, N218S | 85 | |
| Y217L, N79D, I122A4, P40Q | 72 | |

TABLE 3-continued

| VARIANT | % Remaining Activity 40° and 50° C. | |
|---|---|---|
| | 40° | 50° |
| Y217L, N79D, I122A4, D41A | 77 | |
| Y217L, N79D, I122A4, H238Y | 73 | |

*BPN' = *B. amyloliquefaciens* (Y217 L)

As can be seen from Table 3, The variants including N76D have an increased amount of enzymatic activity remaining and thus has a broader thermal stability than P1. For example, at 50° C., N76D compounds had 71%, 29%, 64%, 58% and 84% activity remaining whereas P1, without the stabilizing residue variants, had only 11% activity remaining. In addition, whereas Q206L; N218S, P40Q, D41A, AND H238Y had 76%, 85%, 72%, 77%, and 73% activity remaining whereas LAP 2 had 56% activity remaining without the additional stabilizing residues. All enzymes had enhanced stability in the presence of bodywash at 50°, but P1- N76D, N79A, I122A, Q206L, N218S had the best stability.

Having described the preferred embodiments of the present invention, it will appear to those ordinarily skilled in the art that various modifications may be made to the disclosed embodiments, and that such modifications are intended to be within the scope of the present invention.

We claim:

1. A subtilisin variant comprising three or more amino acid substitutions selected from the group of substitution sets consisting of:
   (a) the replacement isoleucine at position 122 with alanine, the replacement of isoleucine at position 79 with alanine, and the replacement of tyrosine at position 217 with any of leucine, methionine or serine; and
   (b) the replacement of isoleucine at position 122 with alanine, the replacement of asparagine at position 76 with aspartic acid, the replacement of isoleucine at position 79 with alanine, and the replacement of tyrosine at position 217 with any of leucine, methionine or serine;
   wherein, (i) said positions 76, 79, 122, and 217 correspond to positions 76, 79, 122, and 217 in the amino acid sequence of *Bacillus amyloliquefaciens* subtilisin set forth in SEQ ID NO:3, and (ii) the subtilisin variant produces a lesser immunogenic response by comparison with a subtilisin not comprising a substitution set of (a) or (b) measured by an in vitro reduction in allergenicity.

2. The subtilisin variant of claim 1, comprising a further substitution at one or more positions selected from the group consisting of positions corresponding to positions 46, 47, 48, 50, 101, 104, 107, 128, 154, 181, 182, 183, 185, 215, 216, 247, 248, 250, 254, 258, and 262 in the amino acid sequence of *Bacillus amyloliquefaciens* subtilisin set forth in SEQ ID NO:3.

3. The variant of claim 2, wherein said substitutions are selected from the group consisting of the replacement of the glycine at position 46 with serine, the replacement of the glycine at position 47 with serine, the replacement of the alanine at position 48 with glycine, the replacement of the methionine at position 50 with alanine, the replacement of the serine at position 101 with valine, glutamine, or arginine, the replacement of a tyrosine at position 104 with tryptophan, the replacement of the isoleucine at position 107 with valine, the replacement of the glycine at position 128 with serine, the replacement of the serine at position 154 with glycine, the replacement of the aspartic acid at position 181 with glycine, the replacement of the serine at position 182 with threonine or arginine, the replacement of the serine at position 183 with arginine, the replacement of the glutamine at position 185 with alanine, the replacement of the glycine at position 215 with alanine, the replacement of the alanine at position 216 with glutamic acid or histidine, the replacement of the tyrosine at position 217 with serine, the replacement of the arginine at position 247 with tyrosine, serine or glutamine, the replacement of the serine at position 248 with glycine, the replacement of leucine at position 250 with glycine, the replacement of threonine at position 254 with glycine or alanine, the replacement of the glycine at position 258 with serine, and the replacement of the tyrosine at position 262 with phenylalanine.

4. The subtilisin variant of claim 1, comprising a further substitution at one or more positions selected from the group consisting of positions corresponding to positions 3, 31, 40, 41, 76, 111, 147, 206, and 218 in the amino acid sequence of *Bacillus amyloliquefaciens* subtilisin set forth in SEQ ID NO:3.

5. The variant of claim 4, wherein said substitution is selected from the group consisting of the replacement of the serine at position 3 with threonine, the replacement of the isoleucine at position 31 with leucine, the replacement of the proline at position 40 with glutamine, the replacement of the aspartic acid at position 41 with alanine, the replacement of the asparagine at position 76 with arginine, the replacement of the isoleucine at position 111 with valine, the replacement of the valine at position 147 with proline, the replacement of the glutamine at position 206 with leucine, the replacement of the tyrosine at position 217 with methlonine, and the replacement of the aspargine at position 218 with serine.

6. A personal care product, a shampoo, a body lotion, or an oral cleaning composition comprising the variant of claim 1.

7. A skin care composition comprising the subtilisin variant of claim 1.

8. The skin care composition of claim 7, further comprising a cosmetically acceptable carrier.

9. The skin care composition of claim 7 wherein said carrier comprises a hydrophilic diluent selected from the group consisting of water, propylene glycol, ethanol, propanol, glycerol, butylene glycol, polyethylene glycol having a molecular weight from about 200 to about 600, polypropylene glycol having a molecular weight from about 425 to about 2025, and mixtures thereof.

10. The skin care composition of claim 7, further comprising a skin care active.

11. The skin care composition of claim 10, wherein said skin care active is selected from the group consisting of Vitamin B3 component, panthenol, Vitamin E, Vitamin E acetate, retinol, retinyl proplonate, retinyl palmitate, retinoic acid, Vitamin C, theobromine, alpha-hydroxyacid, famesol, phytrantriol, salicylic acid, palmityl peptapeptide-3 and mixtures thereof.

12. The skin care composition of claim 11, wherein said Vitamin B3 component is niacinamide.

13. The skin care composition of claim 11, further comprising glycerine.

14. A skin care composition comprising:
   a) from about 0.00001% to about 1%, by weight, of a subtilisin variant of claim 1;

b) from about 0.01% to about 20%, by weight, of a humectant;

c) from about 0.1% to about 20%, by weight, of a skin care active;

d) from about 0.05% to about 15%, by weight, of a surfactant; and e) from about 0.1% to about 20%, by weight, of silicone.

15. A nucleic acid encoding the subtilisin variant of claim 1.

16. An expression vector comprising the nucleic acid of claim 15.

17. A host cell transformed with the expression vector of claim 16.

* * * * *